(12) United States Patent
Kimura et al.

(10) Patent No.: US 8,133,859 B2
(45) Date of Patent: Mar. 13, 2012

(54) SCGB3A2 AS A GROWTH FACTOR AND ANTI-APOPTOTIC AGENT

(75) Inventors: Shioko Kimura, Bethesda, MD (US); Reiko Kurotani, Kanagawa (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 156 days.

(21) Appl. No.: 12/442,927

(22) PCT Filed: Sep. 27, 2007

(86) PCT No.: PCT/US2007/079771
§ 371 (c)(1),
(2), (4) Date: Mar. 25, 2009

(87) PCT Pub. No.: WO2008/039941
PCT Pub. Date: Apr. 3, 2008

(65) Prior Publication Data
US 2010/0093621 A1 Apr. 15, 2010

Related U.S. Application Data

(60) Provisional application No. 60/847,747, filed on Sep. 27, 2006, provisional application No. 60/880,134, filed on Jan. 12, 2007.

(51) Int. Cl.
*A61K 38/18* (2006.01)
(52) U.S. Cl. .................................. 514/7.6; 514/21.3
(58) Field of Classification Search .................. None
See application file for complete search history.

(56) References Cited

U.S. PATENT DOCUMENTS

| | | | |
|---|---|---|---|
| 5,939,265 A | 8/1999 | Cohen et al. | |
| 5,976,873 A | 11/1999 | Bohinski et al. | |
| 6,037,149 A | 3/2000 | Levitt et al. | |
| 6,087,485 A | 7/2000 | Brooks-Wilson et al. | |
| 2004/0234982 A1 | 11/2004 | Kimura et al. | |
| 2005/0054822 A1 | 3/2005 | Shu et al. | |
| 2005/0261180 A1 | 11/2005 | Pilon et al. | |
| 2006/0035852 A1 | 2/2006 | Sahin et al. | |

FOREIGN PATENT DOCUMENTS

| | | |
|---|---|---|
| CA | 2 331 934 | 6/2002 |
| WO | WO 9708321 | 3/1997 |
| WO | WO 9820143 | 5/1998 |
| WO | WO 9853846 | 12/1998 |
| WO | WO 9910529 | 3/1999 |
| WO | WO 9937809 | 7/1999 |
| WO | WO 0006767 | 2/2000 |
| WO | WO 0006768 | 2/2000 |
| WO | WO 0017392 | 3/2000 |
| WO | WO 0017393 | 3/2000 |
| WO | WO 0017394 | 3/2000 |
| WO | WO 03/003979 | 1/2003 |
| WO | WO 03000111 | 1/2003 |
| WO | WO 03046125 | 6/2003 |

OTHER PUBLICATIONS

Anderson and Shive, "Biodegradation and biocompatibility of PLA and PLGA microspheres," *Adv. Drug Del. Rev.*, 28:5-24, 1997.
Ang and Rossant, "HNF-3beta is essential for node and notochord formation in mouse development," *cell*, 78:561-574, 1994.
Avril-Delplanque et al., "Aquaporin-3 Expression in Human Fetal Airway Epithelial Progenitor Cells," *Stem Cells*, 23:992-1001, 2005.
Batra et al., "Uteroglobin-related protein 1(UGRP1) gene polymorphisms and atopic asthma in the Indian population," *Int. Arch. Allergy Immunol.*, 136:1-6, 2005.
Bellusci et al., "Evidence from normal expression and targeted misexpression that bone morphogenic protein (Bmp-4) plays a role in mouse embryonic lung morphogenesis," *Development*, 122:1693-1702, 1996.
Bin et al., "Identification of uteroglobin-related protein 1 and macrophage scavenger receptor with collagenous structure as a lung-specific ligand-receptor pair," *J. Immunol.*, 171:924-930, 2003.
Blaker et al., "In vitro evaluation of novel bioactive composites based on Bioglass-filled polylactide foams for bone tissue engineering scaffolds," *J. Biomed. Mater. Res.*, 67A:1401-1411, 2003.
Bosquillon et al., "Influence of formulation excipients and physical characteristics of inhalation dry powders on their aerosolization performance," *J. Control. Release*, 70:329-339, 2001.
Brown and Duck-Chong, "Methods of evaluating fetal lung maturity," *Crit. Rev. Clin. Lab. Sci.*, 16:85-159, 1982.
Budinger et al., "Proapoptotic Bid is required for pulmonary fibrosis," *Proc. Natl. Acad. Sci.*, 103:4604-4609, 2006.
Cardoso, "Molecular regulation of lung development," *Ann. Rev. Physiol.*, 63:471-494, 2001.
Chiba et al., "Decreased expression of uteroglobin-related protein 1 in inflamed mouse airways is mediated by IL-9," *Am. J. Physiol. Lung Cell Mol. Physiol.*, 287:L1193-1198, 2004.
Chiba et al., "Interleukin-5 reduces the expression of uteroglobin-related protein (UGRP) 1 gene in allergic airway inflammation," *Immunol. Lett.*, 97:123-129, 2005.
Chiba et al., "Uteroglobin-related protein 1 expression suppresses allergic airway inflammation in mice," *Am. J. Respir. Crit. Care Med.*, 173:958-964, 2006.
Coester et al., "Gelatin nanoparticles by two step desolvation—a new preparation method, surface modifications and cell uptake," *J. Microencapsul.*, 17:187-193, 2000.
Cohen et al., "Induction of leptin receptor expression in the liver by leptin and food deprivation," *J. Biol. Chem.*, 280:10034-10039, 2005.
Collaborative Study on the Genetics of Asthma, "A genome-wide search for asthma susceptibility loci in ethnically diverse populations. The Collaborative Study on the Genetics of Asthma (CSGA)," *Nature Genet.*, 15:389-392, 1997.
Cookson and Moffatt, "Genetics of asthma and allergic disease," *Human Molec. Genet.*, 9:2359-2364, 2000.
Dailey et al., "Nebulization of biodegradable nanoparticles: impact of nebulizer technology and nanoparticle characteristics on aerosol features," *J. Control Release*, 86:131-144, 2003.
Daniels et al., "A genome-wide search for quantitative trait loci underlying asthma," *Nature*, 383:247-250, 1996.
Elomaa et al., "Cloning of a novel bacteria-binding receptor structurally related to scavenger receptors and expressed in a subset of macrophages," *Cell*, 80:603-609, 1995.

(Continued)

Primary Examiner — Marianne P Allen
(74) Attorney, Agent, or Firm — Klarquist Sparkman, LLP

(57) ABSTRACT

The present disclosure is generally related to methods of using the secretory protein SCGB3A2 for promoting lung development and treating lung disease. Some embodiments are, for example, methods for treating and inhibiting the development of neonatal respiratory distress. Other embodiments are methods of promoting lung development in damaged or diseased lungs. Also disclosed are methods for inhibiting lung damage due to anti-cancer agents.

7 Claims, 22 Drawing Sheets

OTHER PUBLICATIONS

Evans et al., "Role of Nonciliated Cells in Renewal of the Bronchial Epithelium of Rats Exposed to NO$_2$," *Am. J. Pathol.*, 123:126-133, 1986.

Gharaee-Kermani et al., "Animal models of pulmonary fibrosis," *Methods Mol Med.*, 117:251-9, 2005.

Giangreco et al., "Lung cancer and lung stem cells," *Am. J. Respir. Crit. Care. Med.*, 175:547-553, 2007.

Goodman et al., "Inflammatory cytokines in patients with persistence of the acute respiratory distress syndrome," *Am. J. Respir. Crit. Care Med.*, 154:602-611, 1996.

Grande et al., "Lung fibrosis induced by bleomycin: structural changes and overview of recent advances," *Scanning Microscopy*, 12: 487-494, 1998.

Grenache and Gronowski, "Fetal lung maturity," *Clin. Biochem.*, 39:1-10, 2006.

Griffin and Nicholls, "Metabolomics as a functional genomic tool for understanding lipid dysfunction in diabetes, obesity and related disorders," *Pharmacogenomics*, 7:1095-1107, 2006.

Henson et al., "Leptin receptor expression in fetal lung increases in late gestation in the baboon: a model for human pregnancy," *Reproduction*, 127:87-94, 2004.

Hogan, "Building organs from buds, branches and tubes," *Differentiation*, 74:323-325, 2006.

Hong et al., "In vivo differentiation potential of tracheal basal cells: evidence for multipotent and unipotent subpopulations," *Am. J. Physiol. Lung Cell. Mol. Physiol.*, 286:L643-L649, 2004.

Horster, "Embryonic epithelial membrane transporters," *Am. J. Physiol. Renal Physiol.*, 279:F982-986, 2000.

Hui et al., "Expression of three mouse homologues of the *Drosophila* segment polarity gene cubitus interruptus, Gli, Gli-2 and Gli-3, in ectoderm- and mesoderm-derived tissues suggests multiple roles during post-implementation development," *Dev. Biol.*, 162:402-413, 1994.

Jacobs and Muller, "Production and characterization of a budesonide nanosuspension for pulmonary administration," *Pharmaceutical Research*, 19:189-194, 2002.

Jian et al., "No evidence for association between the -112G/A polymorphism of UGRP1 and childhood atopic asthma," *Clin. Exp. Allergy*, 33:902-904, 2003.

Kaplan, "Molecular determinants of fetal lung organogenesis," *Mol. Genet. Metab.*, 71:321-341, 2000.

Katiyar et al., "Studies on the intracellular localization of hHR23B," *Biochem. Biophys. Res. Commun.*, 337:1296-1300, 2005.

Kimura et al., "The T/ebp null mouse: thyroid-specific enhancer-binding protein is essential for the organogenesis of the thyroid, lung, ventral forebrain, and pituitary," *Genes Dev.*, 10:60-69, 1996.

Klug et al., "Uteroglobin/Clara cell 10-kDa family of proteins: nomenclature committee report," *Ann. N.Y. Acad. Sci.*, 923:348-354, 2000.

Kurotani et al., "Role of Secretoglobin 3A2 in Lung Development," *Am. J. Respir. Crit. Care Med.*, 178: 389-398, 2008.

Lamprecht et al., "Biodegradable monodispersed nanoparticles prepared by pressure homogenization-emulsification," *Int. J. Pharma.*, 184:97-105, 1999.

Lazzaro et al., "The transcription factor TTF-1 is expressed at the onset of thyroid and lung morphogenesis and in restricted regions of the fetal brain," *Development*, 113:1093-1104, 1991.

Lebeche et al., "Fibroblast growth factor interactions in the developing lung," *Mech. Dev.*, 86:125-136, 1999.

Lee and Gardella, "Surface perspectives in the biomedical applications of poly(alpha-hydroxy acid)s and their associated copolymers," *Analytical and Bioanalytical Chem.*, 373:526-537, 2002.

Lee et al., "Bleomycin induces alveolar epithelial cell death through JNK-dependent activation of the mitochondrial death pathway," *Am. J. Physiol. Lung Cell Mol. Physiol.*, 289:L521-L528, 2005.

Genbank Accession No. AA096507, Feb. 17, 1997.
Genbank Accession No. AC011352, Oct. 12, 2002.
Genbank Accession No. AC011402, Mar. 7, 2002.
Genbank Accession No. AF274959, Oct. 31, 2001.
Genbank Accession No. AF274960, Oct. 31, 2001.
Genbank Accession No. AF274961, Oct. 31, 2001.
Genbank Accession No. AF313456, Nov. 19, 2002.
Genbank Accession No. AF313455, Nov. 1, 2001.
Genbank Accession No. AF313458, Nov. 19, 2002.
Genbank Accession No. AF313459, Nov. 23, 2000.
Genbank Accession No. AI391046, Mar. 15, 2000.
Genbank Accession No. AI355612, Feb. 15, 1999.
Genbank Accession No. AI355302, Jan. 4, 1999.
Genbank Accession No. AW974727, Jun. 2, 2000.
Genbank Accession No. AZ403509, Oct. 3, 2000.

Lin et al., "Biocompatibility of poly-DL-lactic acid (PDLLA) for lung tissue engineering," *J. Biomaterials Application*, 21:109-118, 2006.

Litingtung, et al., "Sonic hedgehog is essential to foregut development," *Nat. Genet.*, 20:58-61, 1998.

Liu et al., "Growth and differentiation of tracheal epithelial progenitor cells," *Am. J. Physiol.*, 266 (Lung Cell. Mol. Physiol. 10): L296-L307, 1994.

Liu et al., "GATA-6 is required for maturation of the lung in late gestation," *Am. J. Physiol. Lung Cell. Mol. Physiol.*, 283:L468-L475, 2002.

Maquet et al., "Porous poly($\alpha$-hydroxyacid)/Bioglass® composite scaffolds for bone tissue engineering. I: preparation and in vitro characterization," *Biomaterials*, 25:4185-4194, 2004.

Minoo et al., "Defects in tracheoesophageal and lung morphogenesis in Nkx2.1(-/-) mouse embryos," *Dev. Biol.*, 209:60-71, 1999.

Moffatt and Cookson, "Gene identification in asthma and allergy," *Int. Arch. Immunol.*, 116:247-252, 1998.

Motoyama et al., "Essential function of Gli2 and Gli3 in the formation of lung, trachea and oespohagus," *Nat. Genet.*, 20:54-57, 1998.

Mukherjee et al., "Uteroglobin: a novel cytokine?," *Cell Mol. Life*, 55:771-787, 1999.

Neuringer and Randell, "Lung stem cell update: promise and controversy," *Monaldi Arch Cehst Dis.*, 65:47-51, 2006.

Neuringer and Randell, "Stem cells and repair of lung injuries," *Respir. Res.*, 5:6, 2004.

Ng et al., "A novel regulation mechanism of DNA repair by damage-induced and RAD23-dependent stabilization of xeroderma pigmentosum group C protein," *Genes Dev.*, 17:1630-1645, 2003.

Ng et al., "Developmental defects and male sterility in mice lacking the ubiquitin-like DNA repair gene mHR23B," *Mol. Cell. Biol.*, 22:1233-1245, 2002.

Niimi et al., "A Polymorphism in the Human UGRP1 Gene Promoter That Regulates Transcription is Associated with and Increased Risk of Asthma," *Am. J. Hum. Genet.* 70:718-725, 2002.

Niimi et al., "Cloning, expression, and chromosomal localization of the mouse gene (Scgb3a1, alias Ugrp2) that encodes a member of the novel uteroglobin-related protein gene family," *Cytogenet. Genomic Res.*, 97:120-127, 2002.

Niimi et al., "Ugrp1, a uteroglobin/ccsp-related protein, is a novel lung-enriched target gene for the t/ebp/nkx2.1 homeodomain transcription factor," *Mol. Endocrinol.*, 15:2021-2036, 2001.

Nord et al., "Regulation of the Clara cell secretory protein/ uteroglobin promoter in lung," *Ann. N.Y. Acad. Sci.*, 923:154-165, 2000.

Ober et al., "Genome-wide search for asthma susceptibility loci in a founder population. The Collaborative Study on the Genetics of Asthma," *Human Molec. Genet.*, 7:1393-1398, 1998.

Ogasawara et al., "Ontogeny of surfactant apoprotein D, SP-D, in the rat lung," *Biochim. Biophys. Acta*, 1083:252-256, 1991.

Ozdemir et al., "A placebo-controlled comparison of effects of repetitive doses of betamethasone and dexamethasone on lung maturation and lung, liver, and body weights of mouse pups," *Pediatr.*, 53:98-103, 2003.

Palecanda and Kobzik, "Receptors for unopsonized particles: the role of alveolar macrophage scavenger receptors," *Curr. Mol. Med.*, 1:589-595, 2001.

Pandey et al., "Poly (DL-lactide-co-glycolide) nanoparticle-based inhalable sustained drug delivery system for experimental tuberculosis," *J. Antimicrobial Chemotherapy*, 52: 981-986, 2003.

Peri et al., "Uteroglobin gene expression in the rabbit uterus throughout gestation and in the fetal lung. Relationship between uteroglobin and eicosanoid levels in the developing fetal lung," *J. Clin. Invest.*, 96: 343-353, 1995.

Perl and Whitsett, "Molecular mechanisms controlling lung morphogenesis," *Clin. Genet.*, 56:14-27, 1999.

Polosukhin et al., "Variability of interalveolar septal remodeling after bleomycin treatment in mice," *Ultrastruct. Pathol.*, 29:53-64, 2005.

Postma et al., "Genetic susceptibility to asthma—bronchial hyper-responsiveness coinherited with a major gene for atopy," *New Engl. J. Med.*, 333:894-900, 1995.

Povirk, "DNA damage and mutagenesis by radiomimetic DNA-cleaving agents: bleomycin, neocarzinostatin and other enediynes," *Mutat. Res.*, 355:71-89, 1996.

Randell, "Airway epithelial stem cells and the pathophysiology of chronic obstructionary pulmonary disease," *Proc. Am Thorac. Soc.*, 3:718-725, 2006.

Rawlins, "Epithelial stem cells of the lung: privileged few or opportunities for many?," *Development*, 133:2455-2465, 2006.

Roether et al., "Development and in vitro characterisation of novel bioresorbable and bioactive composite materials based on polylactide foams and Bioglass® for tissue engineering applications," *Biomaterials*, 23:3871-3878, 2002.

Scherer et al., "In vitro permeability of PBCA nanoparticles through porcine small intestine," *J. Drug Target*, 1:21-27, 1993.

Schoch et al., "A subset of mouse tracheal epithelial basal cells generates large colonies in vitro," *Am. J. Physiol. Lung Cell. Mol. Physiol.*, 286:631-642, 2004.

Sekine et al., "Fgf10 is essential for limb and lung formation," *Nat. Genet.*, 21:138-141, 1999.

Sham et al., "Formulation and characterization of spray-dried powders containing nanoparticles for aerosol delivery to the lung," *Int. J. Pharm.*, 269:457-467, 2004.

Singh and Katyal, "Clara cell proteins," *Ann. N.Y. Acad. Sci.*, 923:43-58, 2000.

Srisodsai et al., "Interleukin-10 Induces Uteroglobin-related Protein (UGRP) 1 Gene Expression in Lung Epithelial Cells through Homeodomain Transcription Factor T/EBP/NKX2.1," *J. Biol. Chem.*, 279:54358-54368, 2004.

Stöhr et al., "cDNA cloning and genomic structure of a novel gene (C11orf9) localized to chromosome 11q12—>q13.1 which encodes a highly conserved, potential membrane-associated protein," *Cytogenet. Cell Genet.*, 88:211-216, 2000.

Sugasawa et al., "Xeroderma pigmentosum group C protein complex is the initiator of global genome nucleotide excision repair," *Mol. Cell*, 2:223-232, 1998.

Szelestei et al., "Association of a uteroglobin polymorphism with rate of progression in patients with IgA nephropathy," *Am. J. Kidney Dis.*, 36(3):468-473, 2000 (abstract only).

Tollin et al., "Vernix caseosa as a multi-component defense system based on polypeptides, lipids and other interactions," *Cell. Mol. Life Sci.*, 62:2390-2399, 2005.

Tomita et al., "CAATT/Enhancer-binding Proteins a and d Interact with NKX2-1 to Synergistically Activate Mouse Secretoglobin 3A2 Gene Expression," *J. Biol. Chem.*, 283:25617-25627, 2008.

Tomita et al., "Oncostatin M Regulates Secretoglobin 3A1 and 3A2 Expression in a Bidirectional Manner," *Am. J. Respir. Cell Mol. Biol.*, 40:620-630, 2009.

Vanbever et al., "Formulation and physical characterization of large porous particles for inhalation," *Pharm. Res.*, 16:1735-1742, 1999.

Verrier et al., "PDLLA/Bioglass® composites for soft-tissue and hard-tissue engineering: an in vitro cell biology assessment." *Biomaterials*, 25:3013-3021, 2004.

Wallach-Dayan et al., "Bleomycin initiates apoptosis of lung epithelial cells by ROS but not by Fas/FasL pathway," *Am. J. Physiol. Lung Cell. Mol. Physiol.*, 290:L790-L796, 2006.

Wang et al., "Abrogation of bleomycin-induced epithelial apoptosis and lung fibrosis by captopril or by a caspase inhibitor," *Am. J. Physiol. Lung Cell Mol. Physiol.*, 279:L143-L151, 2000.

Warburton et al., "The molecular basis of lung morphogenesis," *Mech. Dev.*, 92:55-81, 2000.

Weaver et al., "Bmp4 and Fgf10 play opposing roles during lung bug morphogenesis," *Development*, 127:2695-2704, 2000.

Yamada et al., "Induction of uteroglobin-related protein 2 (UGRP2) gene expression by the Th2 cytokines IL-4 and IL-13," *J. Immunol.*, 175(9):5708-5715, 2005.

Ye et al., "Serum CC-10 in inflammatory lung diseases," *Respiration*, 71:505-510, 2004.

Yuan et al., "Inhibition of distal lung morphogenesis in Nkx2.1(-/-) embryos," *Dev. Dyn.*, 217:180-190, 2000.

Zhang et al., "Human uteroglobin gene: structure, subchromosomal localization, and polymorphism," *DNA and Cell Biology*, 16:73-83, 1997.

Zhang et al., "Severe fibronectin-deposit renal glomerular disease in mice lacking uteroglobin," *Science*, 276:1408-1412, 1997.

Bin et al., "Identification of uteroglobin-related protein 1 and macrophage scavenger receptor with collagenous structure, as a lung-specific ligand-receptor pair," *J of Immunology*, 171(2):924-930, 2003.

Chiba et al., "Uteroglobin-related protein 1 expression suppresses allergic airway inflammation in mice," *American J of Respiratory and Critical Care Medicine*, 173(9):958-964, 2006.

Demayo et al., "Mesenchymal-epithelial interactions in lung development and repair: Are modeling and remodeling the same process?" *American Journal of Physiology—Lung Cellular and Molecular Physiology*, 283(3):L510-L517, 2002.

Niimi et al., "UGRP1, a uteroglobin/clara cell secretory protein-related protein, is a novel lung-enriched downstream target gene for the T/EBP/NKX2.1 homeodomain transcription factor," *Molecular Endocrinology*, 15:2021-2036, 2001.

Reynolds et al., "Secretoglobins SCGB3A1 and SCGB3A2 define secretory cell subsets in mouse and human airways," *Amer J of Respiratory and Critical Care Medicine*, 166(11):1498-1509, 2002.

Srisodsai et al., "Interleukin-10 induces uteroglobin-related protein (UGRP) 1 gene expression in lung epithelial cells through homeodomain transcription factor T/EBP/NKX2.1,"*J of Biological Chemistry*, 279(52):54358-54368, 2004.

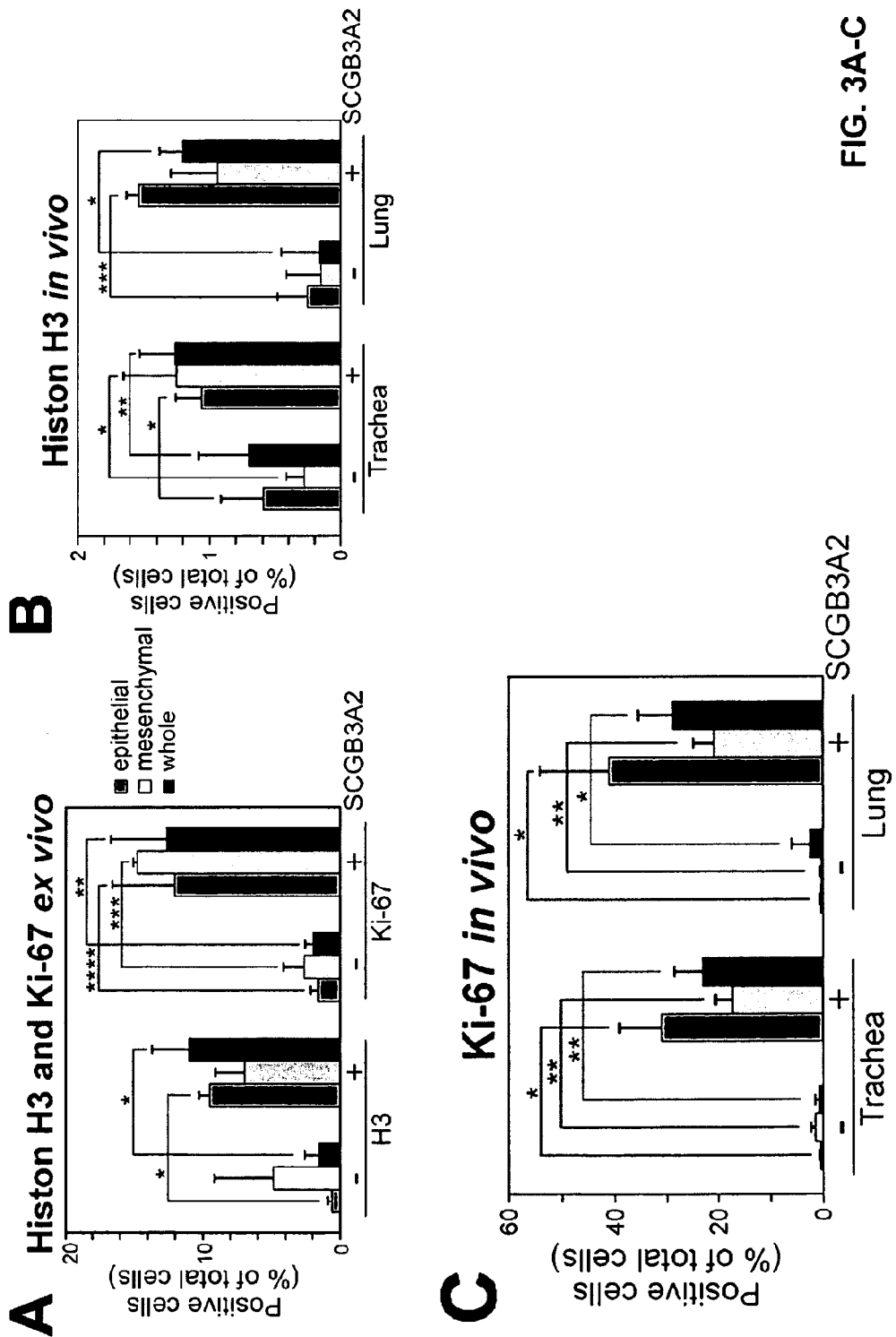
FIG. 3A-C

B PBS 3W
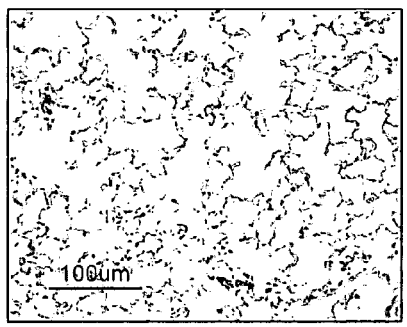
C Bleo 3W
D Bleo 3W-MT
E Bleo+UGRP1
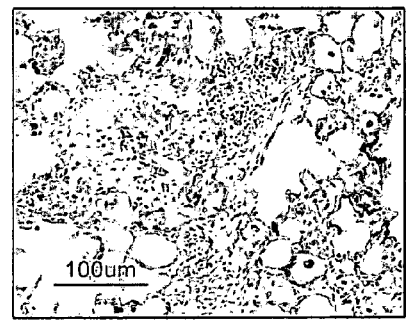
F Bleo+UGRP1
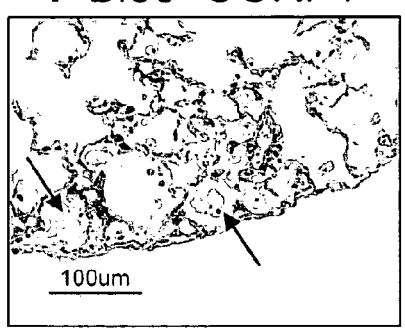
FIG. 9B-F B WT UGRP1
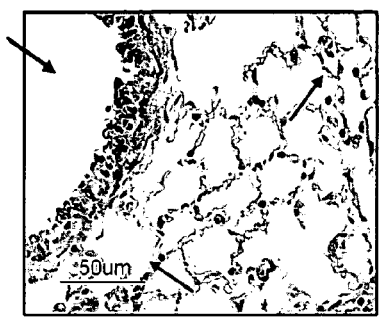
C UGRP1Tg UGRP1
D WT PBS 3W
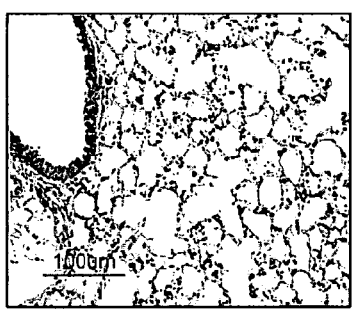
E UGRP1Tg PBS 3W
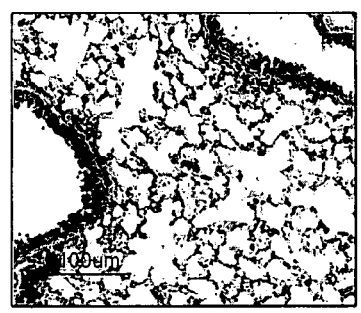
F WT Bleo 3W
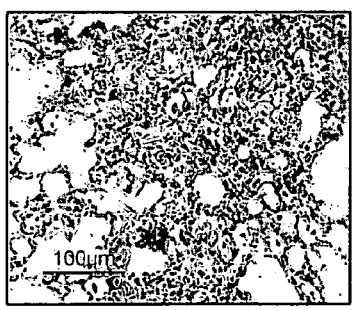
G UGRP1Tg Bleo 3W
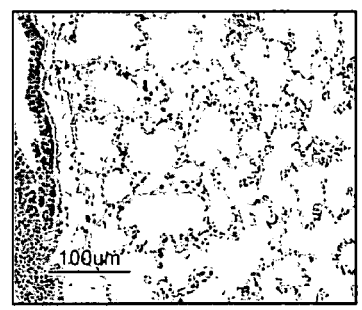
H WT Bleo 3W MT
I UGRP1Tg Bleo 3W
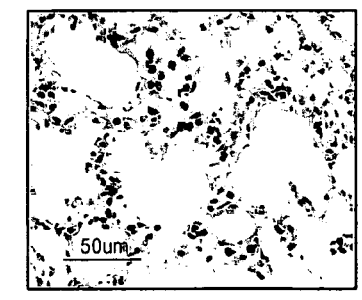
FIG. 10B-I

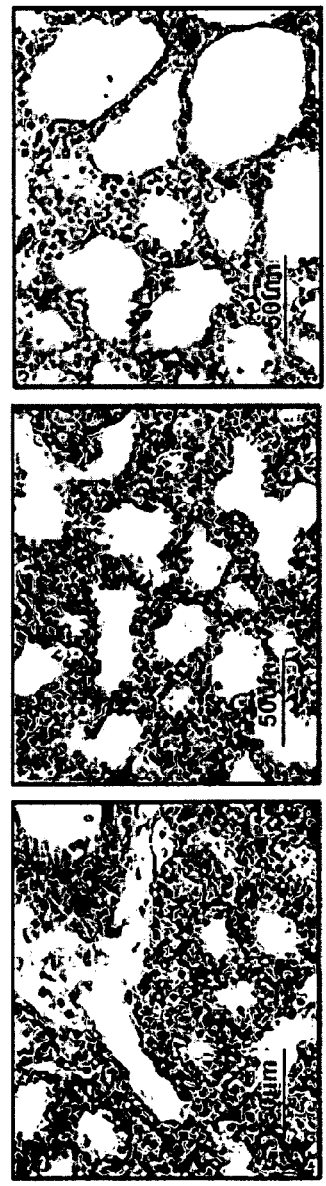
FIG. 15B-C

SEQUENCE LISTING

<160> NUMBER OF SEQ ID NOS: 30

<210> SEQ ID NO 1
<211> LENGTH: 19
<212> TYPE: RNA
<213> ORGANISM: Artificial sequence
<220> FEATURE:
<223> OTHER INFORMATION: Sense Rad23b siRNA probe 1.

<400> SEQUENCE: 1
guagcagguc agaaguuaa                                                    19

<210> SEQ ID NO 2
<211> LENGTH: 19
<212> TYPE: RNA
<213> ORGANISM: Artificial sequence
<220> FEATURE:
<223> OTHER INFORMATION: Antisense Rad23b siRNA probe 1.

<400> SEQUENCE: 2
uuaacuucug accugcuac                                                    19

<210> SEQ ID NO 3
<211> LENGTH: 19
<212> TYPE: RNA
<213> ORGANISM: Artificial sequence
<220> FEATURE:
<223> OTHER INFORMATION: Sense Rad23b siRNA probe 2.

<400> SEQUENCE: 3
gcuucacauu aguaugaga                                                    19

<210> SEQ ID NO 4
<211> LENGTH: 19
<212> TYPE: RNA
<213> ORGANISM: Artificial sequence
<220> FEATURE:
<223> OTHER INFORMATION: Antisense Rad23b siRNA probe 2.

<400> SEQUENCE: 4
ucucauacua augugaagc                                                    19

<210> SEQ ID NO 5
<211> LENGTH: 19
<212> TYPE: RNA
<213> ORGANISM: Artificial sequence
<220> FEATURE:
<223> OTHER INFORMATION: Negative sense siRNA.

<400> SEQUENCE: 5

```
uucuccgaac gugucacgu                                                  19

<210> SEQ ID NO 6
<211> LENGTH: 19
<212> TYPE: RNA
<213> ORGANISM: Artificial sequence
<220> FEATURE:
<223> OTHER INFORMATION: Negative sense siRNA.

<400> SEQUENCE: 6
acgugacacg uucggagaa                                                  19

<210> SEQ ID NO 7
<211> LENGTH: 22
<212> TYPE: DNA
<213> ORGANISM: Artificial sequence
<220> FEATURE:
<223> OTHER INFORMATION: Primer.

<400> SEQUENCE: 7
ggaggagacg gtaaaggcat tg                                              22

<210> SEQ ID NO 8
<211> LENGTH: 24
<212> TYPE: DNA
<213> ORGANISM: Artificial sequence
<220> FEATURE:
<223> OTHER INFORMATION: Primer.

<400> SEQUENCE: 8
tggggaagaa ctgactgtag tggg                                            24

<210> SEQ ID NO 9
<211> LENGTH: 21
<212> TYPE: DNA
<213> ORGANISM: Artificial sequence
<220> FEATURE:
<223> OTHER INFORMATION: Primer.

<400> SEQUENCE: 9
atgaaggaag atggacggct g                                               21

<210> SEQ ID NO 10
<211> LENGTH: 21
<212> TYPE: DNA
<213> ORGANISM: Artificial sequence
<220> FEATURE:
<223> OTHER INFORMATION: Primer.

<400> SEQUENCE: 10
ccagttcgtt tcagtgccac a                                               21

<210> SEQ ID NO 11
<211> LENGTH: 21
<212> TYPE: DNA
<213> ORGANISM: Artificial sequence
<220> FEATURE:
<223> OTHER INFORMATION: Primer.

<400> SEQUENCE: 11
aagactgttc tgtcgcaccc a                                               21

<210> SEQ ID NO 12
<211> LENGTH: 19
<212> TYPE: DNA
<213> ORGANISM: Artificial sequence
<220> FEATURE:
```

```
<223> OTHER INFORMATION: Primer.

<400> SEQUENCE: 12
gccacaattc caactgcca                                                  19

<210> SEQ ID NO 13
<211> LENGTH: 21
<212> TYPE: DNA
<213> ORGANISM: Artificial sequence
<220> FEATURE:
<223> OTHER INFORMATION: Primer.

<400> SEQUENCE: 13
ctacctcggc atgaacgaga a                                               21

<210> SEQ ID NO 14
<211> LENGTH: 21
<212> TYPE: DNA
<213> ORGANISM: Artificial sequence
<220> FEATURE:
<223> OTHER INFORMATION: Primer.

<400> SEQUENCE: 14
atctccttcc ggtgtccaca t                                               21

<210> SEQ ID NO 15
<211> LENGTH: 21
<212> TYPE: DNA
<213> ORGANISM: Artificial sequence
<220> FEATURE:
<223> OTHER INFORMATION: Primer.

<400> SEQUENCE: 15
tttggtgtct tcgttccctg t                                               21

<210> SEQ ID NO 16
<211> LENGTH: 21
<212> TYPE: DNA
<213> ORGANISM: Artificial sequence
<220> FEATURE:
<223> OTHER INFORMATION: Primer.

<400> SEQUENCE: 16
aggtgattgt agctccgcac a                                               21

<210> SEQ ID NO 17
<211> LENGTH: 20
<212> TYPE: DNA
<213> ORGANISM: Artificial sequence
<220> FEATURE:
<223> OTHER INFORMATION: Primer.

<400> SEQUENCE: 17
cggctaccac atccaaggaa                                                 20

<210> SEQ ID NO 18
<211> LENGTH: 20
<212> TYPE: DNA
<213> ORGANISM: Artificial sequence
<220> FEATURE:
<223> OTHER INFORMATION: Primer.

<400> SEQUENCE: 18
attggagctg gaattaccgc                                                 20

<210> SEQ ID NO 19
```

```
<211> LENGTH: 57
<212> TYPE: DNA
<213> ORGANISM: Artificial sequence
<220> FEATURE:
<223> OTHER INFORMATION: oligonucleotide

<400> SEQUENCE: 19
ggcgaaaacc tgtacttcca aggcatgctt ctcatcaacc gtctccctgt tgttgac        57

<210> SEQ ID NO 20
<211> LENGTH: 52
<212> TYPE: DNA
<213> ORGANISM: Artificial sequence
<220> FEATURE:
<223> OTHER INFORMATION: oligonucleotide

<400> SEQUENCE: 20
ggggacaact ttgtacaaga aagttggcta taccaggtgt gaaagagcct cc             52

<210> SEQ ID NO 21
<211> LENGTH: 49
<212> TYPE: DNA
<213> ORGANISM: Artificial sequence
<220> FEATURE:
<223> OTHER INFORMATION: oligonucleotide

<400> SEQUENCE: 21
ggggacaact ttgtacaaaa aagttggcga aaacctgtac ttccaaggc                 49

<210> SEQ ID NO 22
<211> LENGTH: 7
<212> TYPE: PRT
<213> ORGANISM: Artificial sequence
<220> FEATURE:
<223> OTHER INFORMATION: linker amino acid sequence

<400> SEQUENCE: 22

Glu Asn Leu Tyr Phe Gln Gly
1               5

<210> SEQ ID NO 23
<211> LENGTH: 24
<212> TYPE: DNA
<213> ORGANISM: Artificial sequence
<220> FEATURE:
<223> OTHER INFORMATION: primer

<400> SEQUENCE: 23
taagaagcca gagaaccagg tagg                                            24

<210> SEQ ID NO 24
<211> LENGTH: 25
<212> TYPE: DNA
<213> ORGANISM: Artificial sequence
<220> FEATURE:
<223> OTHER INFORMATION: primer

<400> SEQUENCE: 24
ctcagtgatg taaagtggac gaagg                                           25

<210> SEQ ID NO 25
<211> LENGTH: 24
<212> TYPE: DNA
<213> ORGANISM: Artificial sequence
<220> FEATURE:
<223> OTHER INFORMATION: primer

<400> SEQUENCE: 25
```

-continued

```
tttgaggatg cccaggagat gtgc                                          24

<210> SEQ ID NO 26
<211> LENGTH: 21
<212> TYPE: DNA
<213> ORGANISM: Artificial sequence
<220> FEATURE:
<223> OTHER INFORMATION: primer

<400> SEQUENCE: 26
aggaaagcag ccttgttgtg g                                             21

<210> SEQ ID NO 27
<211> LENGTH: 22
<212> TYPE: DNA
<213> ORGANISM: Artificial sequence
<220> FEATURE:
<223> OTHER INFORMATION: primer

<400> SEQUENCE: 27
gctcacccgc aacttctcaa ac                                            22

<210> SEQ ID NO 28
<211> LENGTH: 24
<212> TYPE: DNA
<213> ORGANISM: Artificial sequence
<220> FEATURE:
<223> OTHER INFORMATION: primer

<400> SEQUENCE: 28
tcagcatcca ggtcatactc ctcc                                          24

<210> SEQ ID NO 29
<211> LENGTH: 21
<212> TYPE: DNA
<213> ORGANISM: Artificial sequence
<220> FEATURE:
<223> OTHER INFORMATION: primer

<400> SEQUENCE: 29
aggaatcgtt ctgcaaatcc a                                             21

<210> SEQ ID NO 30
<211> LENGTH: 24
<212> TYPE: DNA
<213> ORGANISM: Artificial sequence
<220> FEATURE:
<223> OTHER INFORMATION: primer

<400> SEQUENCE: 30
tatgccaggt taagtgcagc tatc                                          24
```

SCGB3A2 AS A GROWTH FACTOR AND ANTI-APOPTOTIC AGENT

PRIORITY CLAIM

This is the U.S. National Stage of International Application No. PCT/US2007/079771, filed Sep. 27, 2007, which was published in English under PCT Article 21(2), which in turn claims the benefit of U.S. Provisional Patent Application No. 60/847,747, filed Sep. 27, 2006, and U.S. Provisional Patent Application No. 60/880,134, filed Jan. 12, 2007. Each of these applications is incorporated by reference herein in its entirety.

FIELD

The present disclosure is generally related to methods of promoting lung development and treating lung disease, for example, methods for treating and inhibiting the development of neonatal respiratory distress, methods of promoting lung development, and methods for inhibiting lung damage due to anti-cancer agents.

BACKGROUND

Neonatal respiratory distress syndrome (RDS), also called respiratory distress syndrome of prematurity, is a syndrome caused by developmental lack of surfactant and structural immaturity in the lungs of premature infants. RDS affects about 1% of newborn infants. The incidence decreases with advancing gestational age, from about 50% in babies born at 26-28 weeks, to about 25% at 30-31 weeks. The syndrome is more frequent in infants of diabetic mothers and in the second born of premature twins. Despite huge advances in care, RDS remains the most common single cause of death in the first month of life. Complications include metabolic disorders (acidosis, low blood sugar), patent ductus arteriosus, low blood pressure, chronic lung changes, and intracranial hemorrhage.

Pulmonary fibrosis is a disease of inflammation that results in scarring, or fibrosis, of the lungs. In time, this fibrosis can build up to the point where the lungs are unable to provide oxygen to the tissues of the body. The average survival rate for a subject with pulmonary fibrosis is about four to six years after diagnosis. Pulmonary fibrosis is the most common side effect of certain anti-cancer agents, such as cytotoxic antibiotics.

Given the foregoing, it would be desirable to have effective methods for treating or preventing neonatal respiratory distress syndrome, and methods of inhibiting the development of pulmonary fibrosis resulting from exposure to anti-cancer agents such as cytotoxic antibiotics.

SUMMARY

Disclosed herein are methods for treating and inhibiting the development of neonatal respiratory distress, methods of promoting lung development, and methods of inhibiting or reducing lung damage that results from treatment with certain anti-cancer agents. These methods are based on the surprising discovery that the secretory protein SCGB3A2 has both growth factor and anti-apoptotic activities, in addition to its previously-known anti-inflammatory activities. Examples of these methods are provided in the context of a specific example of a SCGB3A2 protein; however, other equivalents are contemplated.

One such method of treatment is a method for using SCGB3A2 to treat or inhibit the development of neonatal respiratory distress in a subject. In some embodiments, the SCGB3A2 is administered prenatally, and in other embodiments the SCGB3A2 is administered postnatally.

Also disclosed herein is a method of promoting lung development. The method includes contacting a lung cell with an effective amount of SCGB3A2. In various embodiments the method is carried out in vitro, whereas in other embodiments the method is carried out in vivo.

Yet another method is disclosed for using SCGB3A2 to inhibit or reduce lung damage in a subject being treated with an anti-cancer agent. In some embodiments, the anticancer agent is a cytotoxic antibiotic, and in particular examples, the anti-cancer agent is bleomycin.

The foregoing and other features will become more apparent from the following detailed description of several embodiments, which proceeds with reference to the accompanying figures.

BRIEF DESCRIPTION OF THE FIGURES

FIGS. 1A and 1B are digital images of immunohistochemistry for SCGB3A2 (FIG. 1A) and TITF1 (FIG. 1B). Arrows indicate representative positive signals. FIGS. 1C-J are digital images showing organ cultures. Fetal lung is shown at E11.5 before culture (FIG. 1C), after 4-days culture in control media (FIG. 1D), in the presence of 50 ng/ml SCGB3A2 (FIG. 1E), in the presence of 250 ng/ml SCGB3A2 (FIG. 1F), in the presence of 50 ng/ml SCGB3A2 and 2% SCGB3A2-specific antiserum (FIG. 1G), in the presence of 250 ng/ml SCGB3A2 and 2% SCGB3A2-specific antiserum (FIG. 1H), in the presence of 2% preimmune serum (FIG. 1I), and in the presence of 2% SCGB3A2-specific antiserum (FIG. 1J). Scale bar: 0.5 mm.

FIGS. 2A-F show ex vivo cultured fetal lungs: dissecting microscopic observation of Titf1-null lung (FIG. 2A), Titf1-null lung cultured with SCGB3A2 for 4 days (FIG. 2B), Titf1-null lung cultured without SCGB3A2 for 4 days (FIG. 2C), hematoxylin and eosin (H&E) staining of tissue shown in FIG. 2C (FIG. 2E) and FIG. 2B (FIGS. 2D and 2F). FIGS. 2G-J show the histology of Titf1-null embryos: H&E staining of trachea without (FIG. 2G) and with SCGB3A2 treatment (FIG. 2H), and lung without (FIG. 2I) and with SCGB3A2 treatment (FIG. 2J). Inserts in FIGS. 2G and 2I show ciliated cells that are infrequently seen in trachea and lung of null fetus. Representative ciliated cells are shown by arrows in FIGS. 2G-J. Scale bar: (FIGS. 2A-C) 0.5 mm, (FIGS. 2D-F) 100 µm, (FIGS. 2G-J) 50 µm.

FIG. 3 is a series of graphs and digital images showing that SCGB3A2 induces proliferation in E16.5 Titf1-null fetal lung. FIGS. 3A-C are graphs showing positive cell numbers for phosphorylated histone H3 and Ki-67 immunostaining, counted in epithelial and mesenchymal cells separately or as a whole from ex vivo cultured Titf1-null fetal lung (FIG. 3A), and Titf1-null fetal lung and trachea (FIGS. 3B and 3C) with and without SCGB3A2 treatment, and are expressed in a bar graph with SD. (For examples of representative immunostaining results, see FIG. 7, below). *P<0.05, P<0.01, *P<0.005, ****P<0.001 by Student's t-test.

In FIG. 5D, positive signals are seen in the basal layers, shown by arrowheads. Br: bronchus, e: epithelia, m: mesenchyme. The insert in FIG. 5F shows the result with sense probe (ss). Scale bar: 100 μm.

FIG. 6A shows the effect of Rad23b siRNA probes on the reduction of Rad23b mRNA levels in fetal lung primary culture cells, examined by quantitative PCR. FIG. 6B shows the RT-PCR analysis for Rad23b expression using primary mesenchymal cells isolated from E16.5 fetal lungs, cultured for 2 days with or without indicated siRNA in the presence or absence of SCGB3A2. FIGS. 6C-H show lung organ culture. E11.5 normal mouse fetal lungs were cultured for two days in control media (FIG. 6C). in the presence of 250 ng/ml SCGB3A2 (FIG. 6D), transfected with 50 nM negative siRNA (FIG. 6E), with 50 nM negative siRNA in the presence of 250 ng/ml SCGB3A2 (FIG. 6F), with 50 nM Rad23b siRNA probe 1 (FIG. 6G), with 50 nM Rad23b siRNA probe 1 in the presence of 250 ng SCGB3A2. Scale bars: 0.5 mm.

FIGS. 7A-D show ex vivo cultured fetal lungs with and without SCGB3A2 for four days. Phosphorylated histone H3 (FIGS. 7A and 7B) and Ki-67 (FIGS. 7C and 7D). FIGS. 7E-L show Titf1-null mouse with and without SCGB3A2 treatment. Trachea (FIGS. 7E, 7F, 7I, and 7J) and lung (FIGS. 7G, 7H, 7K, and 7L) were immunostained for phosphorylated histone H3 (FIGS. 7E-H) and Ki-67 (FIGS. 7I-L). Inserts in FIGS. 7A and 7C show positive cells that are rarely seen. Inserts in FIGS. 7E, 7F, 7H, 7I, 7J, and 7L are magnified images of the small squared areas. Black and red arrows point representative positive signals in epithelia and mesenchymes, respectively. Scale bar: 100 μm.

FIG. 9 is a graph and several digital images showing the effects of SCGB3A2 in a mouse model for bleomycin-induced fibrosis. FIGS. 9B, 9C, 9E, and 9F show the results of H & E staining. FIG. 9D shows the results of Masson staining (MT) for detection of collagen fiber. After three weeks of bleomycin treatment (Bleo 3W), focal interstitial pneumonia and fibrosis developed (FIGS. 9C, 9D) whereas SCGB3A2-treated mouse lungs were mostly normal with small area of fibrosis (FIG. 9E). Distal alveoli presented normal morphology with the presence of occasional macrophages (shown by arrows), suggestive of healed injuries (FIG. 9F). Scale bar: 100 μm.

FIG. 10 is a graph and a series of digital images showing that SCGB3A2 transgenic mice are resistant to bleomycin-induced lung fibrosis. FIGS. 10B and 10C show SCGB3A2 immunostaining of wild-type (FIG. 10B) and SCGB3A2 transgenic mouse lungs (FIG. 10C). In the latter mice, much higher expression of SCGB3A2 was found in alveolar type II cells as compared with control (grey arrow). Black arrow: SCGB3A2 positive epithelial cells. FIGS. 10D-G, 10I show H&E staining. FIG. 10H shows Masson staining. Three weeks after bleomycin treatment (Bleo 3W), fibrosis was produced in wild type mice (WT) as seen in FIGS. 10D, 10F, and 10H, whereas SCGB3A2 transgenic mice (SCGB3A2 Tg) did not develop any fibrosis (FIGS. 10E, 10G, and 10I). Scale bar: FIGS. 10B, 10C, 10I: 50 μm; FIGS. 10D-H 100 μm.

FIG. 15 is a series of graphs and digital images demonstrating that SCGB3A2 promotes lung development and inhibits the development of neonatal respiratory distress in vivo. FIG. 15B is a series of digital gross images of lungs from PBS-treated and 200 μg SCGB3A2-treated E17.5 pups, and PBS-treated Day 0 pups. FIG. 15C is a series of digital images showing histology of lungs from PBS, 100 μg SCGB3A2, and 200 μg SCGB3A2-treated E17.5 and PBS-treated E19.0 pups.

SEQUENCES

Figure 1:
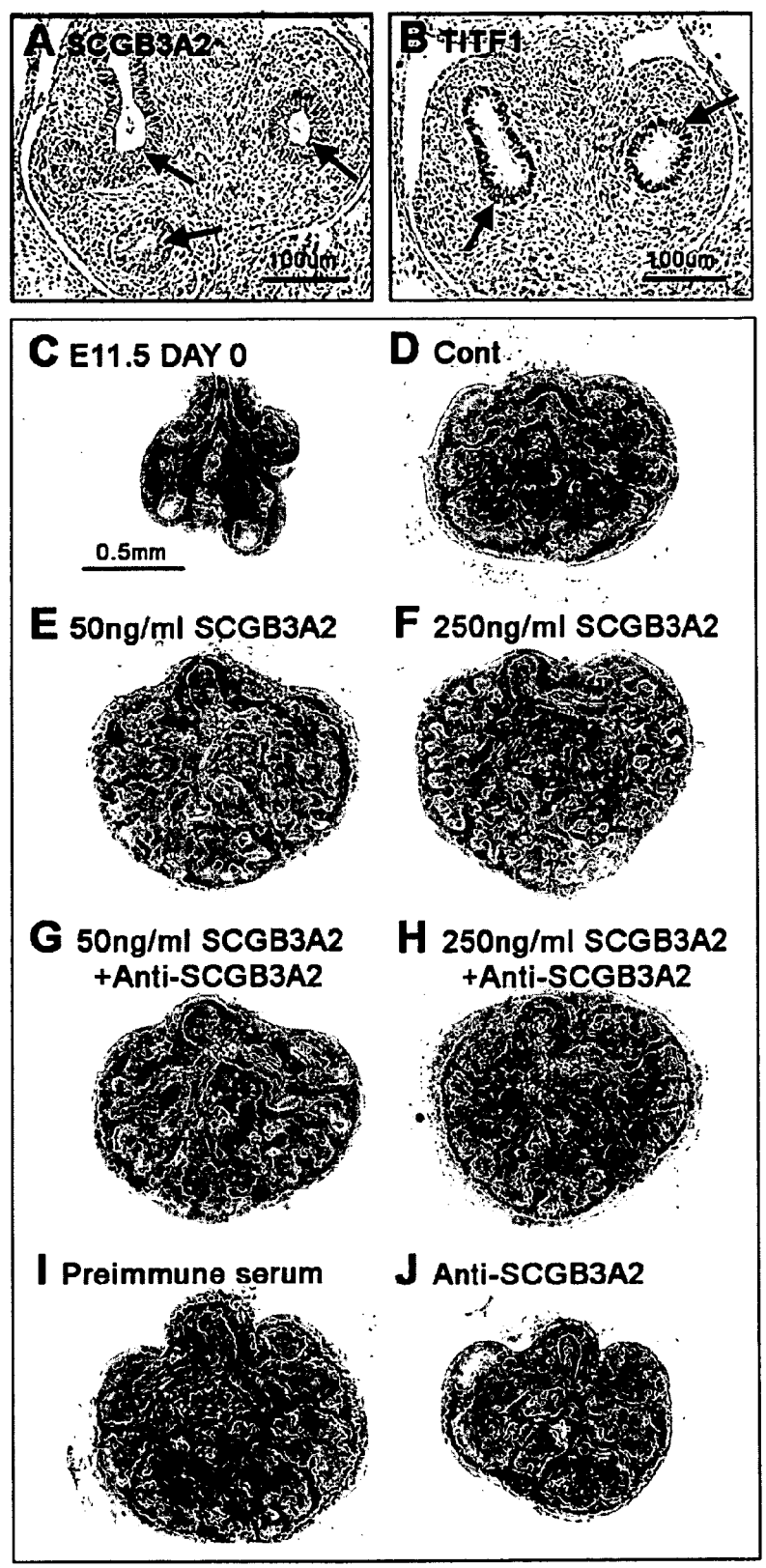
FIG. 1 is a series of digital images showing immunohistochemistry and organ culture of murine fetal lungs at embryonic day 11.5 (E11.5).

SEQ ID NO: 1 is a sense Rad23b siRNA probe 1.
SEQ ID NO: 2 is an antisense Rad23b siRNA probe 1.
SEQ ID NO: 3 is a sense Rad23b siRNA probe 2.
SEQ ID NO: 4 is an antisense Rad23b siRNA probe 2.
SEQ ID NO: 5 is a negative sense siRNA.
SEQ ID NO: 6 is a negative sense siRNA.
SEQ ID NO: 7 is a Rad23b primer (forward).
SEQ ID NO: 8 is a Rad23b primer (reverse).
SEQ ID NO: 9 is an FGF2 primer (forward).
SEQ ID NO: 10 is an FGF2 primer (reverse.
SEQ ID NO: 11 is an FGF7 primer (forward).
SEQ ID NO: 12 is an FGF7 primer (reverse).
SEQ ID NO: 13 is an FGF9 primer (forward).
SEQ ID NO: 14 is an FGF9 primer (reverse).
SEQ ID NO: 15 is an FGF10 primer (forward).
SEQ ID NO: 16 is an FGF10 primer (reverse).
SEQ ID NO: 17 is an 18S primer (forward).
SEQ ID NO: 18 is an 18S primer (reverse).
SEQ ID NO: 19 is oligonucleotide L2575.
SEQ ID NO: 20 is oligonucleotide L2576.
SEQ ID NO: 21 is oligonucleotide L907.
SEQ ID NO: 22 is a linker amino acid sequence.
SEQ ID NO: 23 is an SP-A primer (forward).
SEQ ID NO: 24 is an SP-A primer (reverse).
SEQ ID NO: 25 is an SP-D primer (forward).
SEQ ID NO: 26 is an SP-D primer (reverse).
SEQ ID NO: 27 is an AQP1 primer (forward).
SEQ ID NO: 28 is an AQP1 primer (reverse).
SEQ ID NO: 29 is an OB-R primer (forward).
SEQ ID NO: 30 is an OB-R primer (reverse).

DETAILED DESCRIPTION OF SPECIFIC EMBODIMENTS

I. Overview of Several Embodiments

Disclosed herein are therapeutic methods that make use of the secretory protein SCGB3A2 and equivalents and analogs thereof. These methods are based on the surprising discovery that SCGB3A2 has both growth factor and anti-apoptotic activities, in addition to its previously-known anti-inflammatory activities.

Some embodiments are methods of treating or preventing neonatal respiratory distress in a subject. These methods include administering to the subject an effective amount of SCGB3A2, thereby treating or preventing the neonatal respiratory distress. In certain examples of these methods, the SCGB3A2 is administered prenatally, for instance transplacentally or amniotically. In other embodiments, the SCGB3A2 is administered postnatally, for instance intravenously, intra-arterially, intra-peritoneally, subcutaneously, or by inhalation.

Other methods are methods of promoting lung development. These methods include contacting a lung cell with an effective amount of SCGB3A2, thereby promoting lung development. In some examples of the methods, contacting the lung cell with an effective amount of SCGB3A2 occurs ex vivo, and in particular examples the lung cell is in a component of an explant. Still more particular examples include a further step of transplanting the lung cell (or explant, for instance) into a subject after the cell is contacted with SCBG3A2. In other embodiments of the methods, contacting the lung cell with an effective amount of SCGB3A2 occurs via administering the SCGB3A2 to a subject, for example transplacentally, amniotically, intravenously, intra-arterially, intra-peritoneally, subcutaneously, or by inhalation. In certain examples, the subject has diminished lung capacity, and in more particular examples the subject is a neonate.

Also disclosed are methods of inhibiting or reducing lung damage in a subject being treated with an anti-cancer agent. These methods include administering to the subject an effective amount of SCGB3A2, thereby inhibiting lung damage caused by the anti-cancer agent. In certain embodiments of the method, the SCGB3A2 is administered intravenously, intra-arterially, intra-peritoneally, subcutaneously, or by inhalation, and in particular examples, the SCGB3A2 is administered in conjunction with the anti-cancer agent. In even more particular examples, the anti-cancer agent is a cytotoxic antibiotic, and in some instances, the anti-cancer agent is bleomycin. In certain examples, the lung damage includes pulmonary fibrosis.

The methods disclosed herein are provided in the context of a specific example SCGB3A2 protein, however, other equivalents are contemplated. For instance, animal equivalents of SCGB3A2 would be appropriate for use in veterinary situations, or in animal models of lung development, pulmonary fibrosis, and neonatal respiratory distress, and these and other equivalents also may be used in human therapies.

II. Abbreviations

| | |
|---|---|
| ABVD: | adriamycin, bleomycin, vinblastine, and dacarbazine |
| ALI | acute lung injury |
| AQP1 | aquaporin 1 |
| ARDS | acute respiratory distress syndrome |
| BAL | bronchoalveolar lavage |

| | |
|---|---|
| BrdU: | bromodeoxyuridine |
| COPD | chronic obstructive pulmonary disease |
| CPAP | continuous positive airway pressure |
| FACS: | fluorescent activated cell sorting |
| FBS | fetal bovine serum |
| FEF | forced expiratory flow |
| FEV1 | forced expired volume in one second |
| FGF | Fibroblast growth factor |
| FVC | forced vital capacity |
| H & E | hematoxylin and eosin |
| IMAC | Immobilized Metal Ion Affinity Chromatography |
| IPTG | isopropyl-β-D-thiogalactopyranoside |
| MARCO | macrophage scavenger receptor with collagenous structure |
| MMEFR | maximal midexpiratory rate |
| OB-R | leptin receptor |
| PBS | phosphate-buffered saline |
| PCA | principal components analysis |
| PFA | paraformaldehyde |
| PEFR | peak expiratory flow rate |
| qPCR | quantitative PCR |
| RDS | respiratory distress syndrome |
| SP | surfactant protein |
| TEV | Tobacco Etch Virus |
| TUNEL: | terminal deoxynucleotidyl transferase mediated dUTP Nick End Labeling assay |
| UGRP1 | uteroglobin-related protein 1 |
| XPC | xeroderma pigmentosum group C |

III. Explanation of Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanation of terms is provided:

Acute respiratory distress syndrome (ARDS): An inflammatory lung disease characterized by acute hypoxemia respiratory failure due to pulmonary edema (reviewed in Honing & Ingram, in: *Harrison's Principles of Internal Medicine*, 14th Edition, A. S. Fauci, et al. (eds.), McGraw-Hill, N.Y., pp. 1483-1486, 1998; and Goodman et al., *Am J. Respir. Crit. Care Med.* 154:602-11, 1996). ARDS represents a spectrum of responses to acute lung injury (ALI); these responses occur as complications of a more widespread systemic response to acute inflammation or injury.

ALI develops rapidly after a predisposing condition triggers a systemic inflammatory response, and is most strongly associated with conditions that produce direct alveolar injury or direct injury via the pulmonary capillary bed, such as aspiration, diffuse infection, toxic inhalation, direct injury to the alveolar epithelium, or sepsis syndrome. ALI is the consequence of unregulated over-expression of usual systemic inflammatory responses to infection and/or injury. Injury involves the alveolar epithelium and the pulmonary capillary endothelium, and results in a complex cascade of events. Injury is produced by cellular events associated with neutrophils, macrophages, monocytes, and lymphocytes producing various cytokines, in turn producing cellular activation, chemotaxis, and adhesion.

ARDS can be distinguished from neonatal respiratory distress syndrome, which occurs in newborn infants, and which is a consequence of lung immaturity and lack of sufficient lung surfactant.

Amniotic administration: Administration (to the fetus) via the amniotic fluid. In amniotic administration, an agent is administered maternally, and is absorbed by the fetus from the amniotic fluid. In some examples, an agent is absorbed through fetal skin, and in other examples, it is absorbed through the lungs. Administration to the mother of a compound that is to be delivered to a fetus via amniotic administration includes both oral and parenteral routes of administration, and can include direct injection or infusion into the amniotic sac.

Animal: Living multi-cellular vertebrate organisms, a category that includes, for example, mammals and birds. The term mammal includes both human and non-human mammals. Similarly, the term "subject" includes both human and veterinary subjects. Therefore, the general term "subject" is understood to include all animals, including, but not limited to, humans, or veterinary subjects, such as other primates, dogs, cats, horses, and cows.

Anti-cancer agent: An anti-neoplastic agent. Anti-cancer agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and bbr3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

Apoptosis: A process of cellular suicide. Apoptosis is one of the main types of programmed cell death, and involves an orchestrated series of biochemical events leading to a characteristic cell morphology and death. The apoptotic process is executed in such a way as to safely dispose of cellular debris.

In contrast to necrosis, which is a form of traumatic cell death that results from acute cellular injury, apoptosis is carried out in an orderly process that generally confers advantages during an organism's life cycle. For example, the differentiation of fingers and toes in a developing human embryo requires cells between the fingers to initiate apoptosis so that the digits can separate. Between 50 billion and 70 billion cells die each day due to apoptosis in the average human adult. For an average child between the ages of 8 to 14, approximately 20 billion to 30 billion cells die a day.

Defective apoptotic processes have been implicated in an extensive variety of diseases. Excessive apoptosis causes hypotrophy, such as in ischemic damage, whereas an insufficient amount results in uncontrolled cell proliferation, such as cancer.

Bleomycin: A glycosylated linear nonribosomal peptide antibiotic produced by the bacterium *Streptomyces verticillus*. More generally, the term bleomycin refers to a family of structurally related compounds. When used as an anti-cancer agent, the chemotherapeutical forms are primarily bleomycin A2 and B2. The drug is used in the treatment of Hodgkin's lymphoma (as a component of the adriamycin, bleomycin, vinblastine and dacarbazine (ABVD) regimen), squamous cell carcinomas, and testicular cancer as well as pleurodesis, for instance.

A serious complication of bleomycin treatment is pulmonary fibrosis, which is an inflammatory disease that results in scarring, or fibrosis, of the lungs. In time, this fibrosis can build up to the point where the lungs are unable to provide sufficient oxygen to the tissues of the body. Pulmonary fibrosis sets off a series of events in which the inflammation and immune activity in the lungs, and eventually the fibrosis processes, become uncontrollable.

Bronchodilator: An antispasmodic or other agent that dilates a bronchus or bronchiole. Bronchodilators relax the smooth muscles of the airways, allowing the airway to dilate. Bronchodilator medicines do not counteract inflammation.

Chronic Bronchitis: An inflammatory lung disease that results in a long-standing inflammation of the airways that produces a lot of mucus, causing wheezing and infections. It is considered chronic if a subject has coughing and mucus on a regular basis for at least three months a year and for two years in a row.

Chronic Obstructive Pulmonary Disease (COPD): A lung disease that encompasses two closely related respiratory disorders that cause gradual loss of pulmonary function: chronic bronchitis and emphysema. A subject with COPD sometimes has both chronic bronchitis and emphysema, or may just have one of these diseases. Emphysema is an inflammatory lung disease that destroys the alveolae and/or bronchae. Over time, the lungs lose elasticity. This causes the air sacs to become enlarged, thus making breathing difficult.

In the beginning stages of COPD, a subject may have only a mild shortness of breath and occasional coughing spells. Initial symptoms can include a general feeling of illness, increasing shortness of breath, coughing, and wheezing. But, as the disease progresses, symptoms become increasingly more severe.

The overwhelming cause of COPD is smoking. Approximately 90% of COPD subjects have a history of smoking. In addition, untreated or under-treated asthma may lead to irreversible lung damage. These subjects may have symptoms similar to COPD.

Cystic Fibrosis: An inflammatory lung disease that also affects the lungs and digestive systems, especially the pancreas. It causes the exocrine glands, which produce mucus and sweat, to produce abnormal secretions. Cystic fibrosis causes the cells in the lung tissue to produce an abnormal amount of thick, sticky mucus that clogs the airways of the lungs, resulting in pulmonary obstructions and life-threatening bacterial infections.

Cytotoxic antibiotic: A class of anti-cancer drugs that includes anthracycline family members (for example, daunorubicin, doxorubicin, epirubicin, idarubicin, mitoxantrone, and valrubicin), bleomycin, hydroxyurea, and mitomycin. The most serious complication of treatment with cytotoxic antibiotics is pulmonary fibrosis, which is an inflammatory disease that results in scarring, or fibrosis, of the lungs. In time, this fibrosis can build up to the point where the lungs are unable to provide oxygen to the tissues of the body. Pulmonary fibrosis sets off a series of events in which the inflammation and immune activity in the lungs, and eventually the fibrosis processes, become uncontrollable.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Thus, a reference to the nucleic acid molecule that encodes SCGB3A2 (for instance. UGRP1 type A mRNA: AF274959, type B mRNA: AF274960, type C mRNA: AF274961, mUGRP2: AF313456, EST AI391046, hUGRP1: AF313455, EST AI355612, EST AI355302, and hUGRP2: AF313458, EST AW974727), or a fragment thereof, encompasses both the sense strand and its reverse complement. Thus, for instance, it is appropriate to generate probes or primers from the reverse complement sequence of the disclosed nucleic acid molecules.

Expectorant: A drug or chemical substance that induces the ejection of mucus, phlegm, and other fluids from the lungs and air passages, for example by coughing.

Expiratory Flow Rate: The rate at which air is expelled from the lungs during exhalation. A subject's maximum expiratory flow is measured by a simple pulmonary test; in performing the test, a subject first takes as deep a breath as possible, then exhales as rapidly and as completely as possible into a machine known as a spirometer, which measures the rate of exhalation. Forced expiratory flow 25-75 (FEF 25-75) is a measurement of the forced expiratory flow determined over the midportion of a forced exhalation. An increase in the forced expiratory flow (FEF) or FEF 25-75 reflects a decrease in bronchoconstriction and an improvement in pulmonary function.

Forced Expiratory Volume (FEV; FEV1): The volume of air resulting from the forced expiratory flow test, in which a subject first inspires maximally to the total lung capacity, then exhales as rapidly and as completely as possible. The forced expired volume in one second (FEV1) represents the maximum expiratory air volume a subject can produce during a one-second interval. An increase in FEV or FEV1 reflects a decrease in bronchoconstriction and an improvement in pulmonary function.

Forced Vital Capacity (FVC): The volume of air resulting from the forced expiratory flow test, in which a subject first inspires maximally to the total lung capacity, then exhales as rapidly and as completely as possible. An increase in FVC reflects a decrease in bronchoconstriction and an improvement in pulmonary function.

Growth factor: A protein capable of stimulating cellular proliferation, differentiation, and/or commitment. The term growth factor is sometimes used interchangeably with the term cytokine. Historically, cytokines were associated with hematopoietic (blood forming) cells and immune system cells (for instance, lymphocytes and tissue cells from spleen, thymus, and lymph nodes). However, some of the same signaling proteins used by the hematopoietic and immune systems are used by other cells and tissues, both during development and in the mature organism.

Some specific, non-limiting examples of growth factors include Transforming growth factor beta (TGF-β). Granulocyte-colony stimulating factor (G-CSF), Granulocyte-macrophage colony stimulating factor (GM-CSF), nerve growth factor (NGF), Neurotrophins (for instance, NGF, BDNF, and NT3), Platelet-derived growth factor (PDGF), Erythropoietin (EPO), Thrombopoietin (TPO), Myostatin (GDF-8), Growth differentiation factor-9 (GDF9), Basic fibroblast growth factor (bFGF or FGF2), Epidermal growth factor (EGF), Hepatocyte growth factor (HGF), and, as described herein, SCGB3A2.

Glucocorticoid: A class of steroid hormones characterized by an ability to bind with the cortisol receptor and trigger similar effects. Glucocorticoids have potent anti-inflammatory and immunosuppressive properties. As a consequence, glucocorticoids are widely used as drugs to treat inflammatory conditions such as inflammatory lung diseases. In addition, glucocorticoids have multiple effects on fetal development, including promoting maturation of the lung and production of the surfactant necessary for extrauterine lung function. Thus, they are often administered to women in pre-term labor in order to attempt to speed lung maturation in a pre-term infant.

Specific, non-limiting examples of glucocorticoids include hydrocortisone, cortisone acetate, prednisone, prednisolone, methylprednisolone, dexamethasone, betamethasone, triamcinolone, beclometasone, fludrocortisone acetate, deoxycorticosterone acetate, and aldosterone.

Inflammatory lung disease: A disease of the lung that is associated with lung inflammation. In many inflammatory lung diseases, the inflammatory response that accompanies the underlying disease state is much more dangerous than the underlying infection or trauma. Inflammatory lung diseases can include, but are not limited to pneumonia, ARDS, chronic bronchitis, chronic obstructive pulmonary disease (COPD), cystic fibrosis, pulmonary fibrosis, and pulmonary sarcoidosis. For the purposes of this disclosure, the term inflammatory lung disease does not include neonatal respiratory distress syndrome, which is a condition involving lung immaturity and lack of surfactants.

Inspiratory Flow Rate: The rate at which air travels into the lungs during inspiration. Inspiratory flow is measured by a simple pulmonary test; in performing the test the subject takes as deep and rapid a breath as possible from a machine known as a spirometer, which measures the rate of inspiration. An increase in inspiratory flow rate reflects a decrease in bronchoconstriction and an improvement in pulmonary function.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lung damage: Damage or insult to the lungs or respiratory system. Lung damage includes direct airway or alveolar injury or direct injury via the pulmonary capillary bed, such as aspiration, diffuse infection, toxic inhalation, direct injury to the alveolar epithelium, or sepsis syndrome. Lung damage also includes lung-related drug effects, such as the pulmonary fibrosis that can result from exposure to certain anti-cancer agents, such as the cytotoxic antibiotic bleomycin.

Lung Volume: The maximum volume the lungs can hold.

Nanoparticles: Solid colloidial particles that range in size from about 10-1000 nm. They can be made from biodegradable and biocompatible biomaterials. Active components, such as drugs, can be adsorbed, encapsulated, or covalently attached to their surface or into their matrix.

Neonate: A human or animal infant less than about a month old. The term "neonate" includes premature infants and postmature infants, as well as full term newborns.

Neonatal Respiratory Distress: Also called respiratory distress of prematurity and respiratory distress syndrome (RDS), neonatal respiratory distress results from a lack of pulmonary surfactant, a molecular substance that helps the lung's alveoli (air sacs) do their job of extracting carbon dioxide from the blood and replacing it with oxygen. The surfactant prevents the lung's alveoli from collapsing and helps keep them properly inflated by reducing their surface tension. The absence of surfactant prevents the alveoli from functioning properly. RDS affects about 1% of newborn infants. The incidence decreases with advancing gestational age (length of pregnancy), from about 50% in babies born at 26-28 weeks, to about 25% at 30-31 weeks. The syndrome is more frequent in infants of diabetic mothers and in the second born of premature twins.

Respiratory distress syndrome begins shortly after birth, and is manifested by tachypnea and "sucking in" (retractions) of the chest wall during breathing efforts (respiratory distress). In addition grunting respirations, flaring of the nostrils and cyanosis (a blue discoloration of the skin due to low oxygen content in the blood) are frequent. As the disease progresses, the neonate may develop ventilatory failure (climbing carbon dioxide concentrations in the blood), and prolonged cessations of breathing ("apnea"). Whether treated or not, the clinical course for the acute disease lasts about two to three days. During the first, the patient worsens and requires more support. During the second the subject may be remarkably stable on adequate support and resolution is noted during the third day, heralded by a prompt diuresis. Despite huge advances in care, RDS remains the most common single cause of death in the first month of life. Complications include metabolic disorders (acidosis, low blood sugar), patent ductus arteriosus, low blood pressure, chronic lung changes, and intracranial hemorrhage.

The lungs of an infant with RDS are developmentally deficient in a material called surfactant, which allows the alveoli to remain open throughout the normal cycle of inhalation and exhalation. Surfactant is a complex system of lipids, proteins and glycoproteins which are produced in specialized lung cells called Type II cells or Type II pneumocytes. The surfactant is packaged by the cell in structures called lamellar bodies, and extruded into the alveoli. The lamellar bodies then unfold into a complex lining of the alveoli. This layer serves the purpose of reducing the surface tension which would tend to cause the alveoli to collapse in the presence of gas. Without adequate amounts of surfactant, the alveoli collapse and are very difficult to expand.

Structural immaturity, as manifested by low numbers of alveoli, also contributes to the disease process. Additionally, the oxygen and breathing treatments used, while life-saving, can also damage the lungs. The diagnosis of RDS is made by the clinical picture and the chest x-ray, which demonstrates decreased lung volumes (bell-shaped chest), absence of the thymus (after about six hours), a small (0.5-1 mm), discrete, uniform infiltrate involving all lobes of the lung and airbronchograms. In severe cases, this becomes exaggerated until the cardiac borders become inapparent ('white-out' or 'ground-glass').

Parenteral: Administered outside of the intestine, e.g., not via the alimentary tract. Generally, parenteral formulations are those that will be administered through any possible mode except ingestion. This term especially refers to injections, whether administered amniotically, transplacentally, intravenously, intrathecally, intramuscularly, intraperitoneally, intra-articularly, or subcutaneously, and various surface applications including intranasal, inhalational, intradermal, and topical application, for instance.

Pharmaceutically acceptable carriers: The pharmaceutically acceptable carriers useful in this disclosure are conventional. Martin, *Remington's Pharmaceutical Sciences*, published by Mack Publishing Co. Easton, Pa., 19th Edition, 1995, describes compositions and formulations suitable for pharmaceutical delivery of, for instance SCGB3A2.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pneumonia: An inflammatory lung disease characterized by inflammation and consolidation followed by resolution and caused by infection from viruses, fungi, or physical and chemical irritants or bacteria including: *Pneumonococcus, Streptococcus, Hemolyticus, Staphylococcus, Friedländer's bacillus*, and *influenza bacillus*. Symptoms include high fever, chest pain, difficulty breathing, coughing and sputum.

Preventing or treating a disease: "Preventing" a disease refers to inhibiting the full development of a disease, for example in a person who is at risk for a disease such as neonatal respiratory distress or bleomycin-induced pulmonary fibrosis. An example of a subject at risk for neonatal respiratory distress is a neonate born at less than forty weeks' gestation, a fetus at risk of premature birth, or a fetus or neonate born to a mother with a condition that may cause delayed lung development, such as diabetes. An example of a subject at risk for developing pulmonary fibrosis is someone who has begun or will begin treatment with an anti-cancer agent that can cause pulmonary fibrosis, such as bleomycin. "Treatment" refers to a therapeutic intervention that ameliorates a sign or symptom of a disease or pathological condition after it has begun to develop.

Pulmonary Fibrosis: An inflammatory lung disease that results in scarring, or fibrosis, of the lungs. In time, this fibrosis can build up to the point where the lungs are unable to provide oxygen to the tissues of the body. Pulmonary fibrosis can result from an autoimmune disorder, the after effects of an infection, such as a viral infection, or from exposure to certain anti-cancer agents, such as cytotoxic antibiotics. A specific example of an anti-cancer agent that can cause pulmonary fibrosis is bleomycin.

Pulmonary fibrosis sets off a series of events in which the inflammation and immune activity in the lungs, and eventually the fibrosis processes, become uncontrollable. The average survival rate for a subject with pulmonary fibrosis is about four to six years after diagnosis. Those who develop pulmonary fibrosis at a young age seem to have a longer survival than those who develop it later in life.

Pulmonary function: The function of the respiratory system, which can be measured through a variety of tests, including, but not limited to measurements of airflow (e.g. spirometry) or arterial blood gases. Measurements of airflow included airflow rate, peak expiratory flow rate (PEFR), forced expiratory volume in the first second ($FEV_1$), and maximal midexpiratory rate (MMEFR).

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Rad23b: One of the two *Mus musculus* homologs of the *Saccharomyces cerevisiae* DNA repair protein RAD23. Rad23b is tightly complexed with xeroderma pigmentosum group C(XPC), serving as a primary DNA damage sensor.

Respiratory Disorder: A large variety of abnormalities arising in all structures of the body involved with gas exchange. These structures include the lungs, nose, oropharynx, extra-pulmonary airways, thoracic cage, and respiratory muscles. Respiratory disorders encompass both acute and chronic diseases. Asthma is one specific, non-limiting example of a respiratory disorder. Other specific, non-limiting examples include coughs, pneumonia, bronchitis (for example, chronic obstructive bronchitis), neonatal respiratory distress, pulmonary fibrosis, emphysema, interstitial lung disease, cystic fibrosis, and lung tumors.

SCGB3A2: Also called uteroglobin-related protein 1 (UGRP1), LuLeu1, lu103, Pnsp1, and Hin-2, SCGB3A2 is a member of the uteroglobin/Clara cell secretory protein (UG/CCSP) gene superfamily of secretory proteins, and is predominantly expressed in the epithelial cells of trachea, bronchus, and bronchioles. SCGB3A2 has been shown to suppress lung inflammation using a mouse model for allergic airway inflammation (Chiba et al., (2006) *Am. J. Respir. Crit. Care Med May* 1; 173(9):958-64.). MARCO, a macrophage scavenger receptor that is expressed in lung alveolar macrophages and is involved in pulmonary inflammation, has been identified as the receptor for SCGB3A2 (Bin et al., (2003) *J. Immunol.* 171, 924-30).

As used herein, the term "SCGB3A2" is intended generally. Thus, in one embodiment, SCGB3A2 is a human protein. In another embodiment, SCGB3A2 is a non-human animal homolog/ortholog of the human molecule, such as a sheep, chimpanzee, goat, pig, mouse, rat, or hamster SCGB3A2-equivalent protein.

The human SCGB3A2 gene is about 2,900 base pairs in length and consists of three exons. The first intron of SCGB3A2 is about five to six-fold longer than the second intron, which resembles the structure of orthologous mouse SCGB3A2 gene. Specific, non-limiting examples of SCGB3A2 nucleotide sequences include the following GenBank accession numbers; UGRP1 type A mRNA: AF274959, type B mRNA: AF274960, type C mRNA: AF274961, mUGRP2: AF313456, EST AI391046, hUGRP1: AF313455, EST AI355612, EST AI355302, and hUGRP2: AF313458, EST AW974727. One of ordinary skill in the art will recognize that these are provided merely as examples; other proteins/nucleic acids that fall into the described class will be recognized.

Stem Cells: Primal cells found in all multi-cellular organisms. Stem cells retain the ability to renew themselves through mitotic cell division and can differentiate into a diverse range of specialized cell types. The three broad categories of mammalian stem cells are: embryonic stem cells, which are derived from blastocysts; adult stem cells, which are found in adult tissues; and cord blood stem cells, which are found in the umbilical cord. In a developing embryo, stem cells can differentiate into all of the specialized embryonic tissues. In adult organisms, stem cells and progenitor cells act as a repair system for the body, replenishing specialized cells.

By definition, stem cells possess two properties: self-renewal, the ability to go through numerous cycles of cell division while maintaining the undifferentiated state; and unlimited potency, the capacity to differentiate into any mature cell type. In a strict sense, this requires stem cells to be either totipotent or pluripotent, although some multipotent and/or unipotent progenitor cells are sometimes referred to as stem cells.

Potency specifies the differentiation potential (the potential to differentiate into different cell types) of the stem cell. Pluripotent, embryonic stem cells originate as inner mass cells within a blastocyst. These stem cells can become any tissue in the body, excluding a placenta. Only the morula's cells are totipotent, able to become all tissues and a placenta. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers.

Multipotent stem cells can produce only cells of a closely related family of cells (for instance, hematopoietic stem cells differentiate into red blood cells, white blood cells, platelets, etc.). Unipotent cells can produce only one cell type, but have the property of self-renewal, which distinguishes them from non-stem cells.

The term progenitor cell refers to immature or undifferentiated cells, typically found in postnatal animals. While progenitor cells share many common features with stem cells, the term is far less restrictive. Like stem cells, progenitor cells have a capacity for self-renewal and differentiation, although these properties may be limited. The majority of progenitor cells lie dormant or possess little activity in the tissue in which they reside. They exhibit slow growth and their main role is to replace cells lost by normal attrition. Upon tissue damage or injury, progenitor cells can be activated by growth factors or cytokines, leading to increased cell division important for the repair process.

Subject: Living multi-cellular vertebrate organisms, a category that includes both human and non-human mammals. The methods disclosed herein have equal applications in medical and veterinary settings. Therefore, the general term "subject" is understood to include all animals, including, but not limited to, humans or veterinary subjects, such as other primates, dogs, cats, horses, and cows.

Therapeutically effective amount: A quantity of a specified compound (such as SCGB3A2 or an equivalent thereof) required to achieve a desired effect in a subject being treated. For instance, this can be the amount necessary to treat or prevent neonatal respiratory distress or bleomycin-induced pulmonary fibrosis in a subject, or a dose sufficient to prevent advancement, or to cause regression of a disease, or which is capable of relieving symptoms caused by a disease, such as pain, lung inflammation, fluid accumulation, or shortness of breath.

Transplacental administration: Administration of an agent to a fetus via the placenta. The agent can be administered to the mother via any route of administration, including topical, oral, and parenteral routes of administration. An agent that is administered by transplacental administration crosses from the maternal bloodstream, across the placenta, and into the fetal bloodstream.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

SCGB3A2 and Lung Development

Lung tissue arises by budding from the ventral foregut at approximately embryonic day (E) 9.5 in mouse gestation (Kaufman & Bard (1999) *The Anatomical Basis of Mouse Development*, Academic Press, London). Mouse lung development is classified as four stages; pseudoglandular (E9.5-16.5), canalicular (E16.5-17.5), terminal saccular (E17.5-perinatal day (P) 5), and alveolar (P5-30) (Perl et al., (1999) *Clin. Genet.* 56, 14-27; Warburton et al., (2000) *Mech. Dev.* 92, 55-81). This classification is representative of the complexity of morphological and functional changes that occur during lung development.

Lung development is controlled temporally and spatially by various transcription factors and growth factors (Perl et al., (1999) *Clin. Genet.* 56, 14-27; Cardoso (2001) *Annu. Rev. Physiol.* 63, 471-94). Among them, TITF1, also called T/EBP, TTF1 or NKX2.1, is expressed in lung, thyroid and ventral forebrain during early embryogenesis (Lazzaro et al., (1991) *Development* 113, 1093-104; Kimura et al., (1996) *Genes Dev.* 10, 60-9). Titf1-null mice die at birth due to profoundly hypoplastic lungs (Kimura et al., (1996) *Genes Dev.* 10, 60-9) in addition to other defects, including agenesis of the thyroid and pituitary, and severe malformation of hypothalamus. TITF1 expression appears in the ventral wall of the anterior foregut, an emergence of the lung primordium at E9.5 (Minoo et al., (1999) *Dev. Biol.* 209, 60-71). TITF1 expression continues in the epithelial cells during lung development and throughout adulthood, at which time, expression is confined to epithelial type II cells (Yuan et al., (2000) *Dev. Dyn.* 217, 180-90). Titf1-null lungs exhibit only sac-like structures with rudimentary bronchi (Kimura et al., (1996) *Genes Dev.* 10, 60-9) and do not develop beyond the stage of main bronchi (Minoo et al., (1999) *Dev. Biol.* 209, 60-71; Yuan et al., (2000) *Dev. Dyn.* 217, 180-90). The downstream targets for TITF1 that cause this defect are not known.

SCGB3A2, which was originally named uteroglobin related protein 1 (UGRP1), is a member of the uteroglobin/Clara cell secretory protein (UG/CCSP) gene superfamily of secretory proteins, officially named secretoglobin (SCGB) (Klug et al., (2000) *Ann. N.Y. Acad. Sci.* 923, 348-54). The prototypical protein of this gene superfamily. SCGB1A1 was proposed as a novel cytokine (Mukherjee et al., (1999) *Cell Mol Life Sci* 55, 771-87). SCGB3A2 was identified as a downstream target for TITF1 in lung using suppressive subtractive library screening of mRNAs isolated from lungs of Titf1-null versus wild-type mice (Niimi et al., (2001) *Mol. Endocrinol.* 15, 2021-2036), and is predominantly expressed in the epithelial cells of trachea, bronchus, and bronchioles (Niimi et al., (2001) *Mol. Endocrinol.* 15, 2021-2036).

SCGB3A2 expression is directly regulated by binding of TITF1 to sites located in the promoter of the SCGB3A2 gene (Niimi et al., (2001) *Mol. Endocrinol.* 15, 2021-2036). Recently, SCGB3A2 was demonstrated to suppress allergen-induced lung inflammation using a mouse model for allergic airway inflammation (Chiba et al., (2006) *Am. J. Respir. Crit. Care Med;* 173(9):958-64). MARCO, a macrophage scavenger receptor with collagenous structure that is expressed in lung alveolar macrophages and is involved in pulmonary inflammation, was identified as a receptor for SCGB3A2 (Bin et al., (2003) *J. Immunol.* 171, 924-30). Low SCGB3A2 expression was detected in E12.5 mouse lungs, which markedly increased by E16.5 as determined by RT-PCR (Niimi et al., (2001) *Mol. Endocrinol.* 15, 2021-2036).

Prior to the present disclosure, the function of SCGB3A2 in lung development had not been determined. As disclosed herein, the arrest of branching and development found in Titf1-null lungs is due to the deficiency of SCGB3A2 expression in these lungs. Indeed, SCGB3A2 exhibits growth factor activity, promoting branching and/or proliferation of Titf1-null lungs ex vivo and in vivo. Rad23b, a downstream target of SCGB3A2 and a component of the DNA damage sensor, mediates this growth factor activity in response to SCGB3A2.

SCGB3A2 to Treat and/or Prevent Neonatal Respiratory Distress

Disclosed herein is the surprising discovery that the secretory protein SCGB3A2 has both growth factor and anti-apoptotic activities, in addition to its previously-known anti-inflammatory activities. In one embodiment of the disclosure, the growth factor activity of SCGB3A2 is exploited for treating and/or inhibiting the development of neonatal respiratory distress syndrome. The efficacy of this method was surprising at least because the MARCO receptor previously was believed to mediate SCGB3A2's effects, and MARCO is expressed only at very low levels in fetal lung. (See, for instance, Elomaa et al., (1995) *Cell* 80(4):603-609). Thus, prior to the present disclosure that SCGB3A2 also has growth factor activity that is mediated by a receptor other than MARCO, SCGB3A2 would have been expected to have little if any effect on fetal lung tissue.

Neonatal respiratory distress (also called respiratory distress of prematurity and respiratory distress syndrome (RDS)), results from a lack of pulmonary surfactant, a substance that helps the lung's alveoli extract carbon dioxide from the blood and replace it with oxygen. The surfactant prevents the lung's alveoli from collapsing and helps keep them properly inflated by reducing their surface tension. The absence of surfactant prevents the alveoli from functioning properly. RDS primarily affects premature infants, but also is more frequent in infants of diabetic mothers and in the second-born of premature twins.

A human delivery is considered premature when it occurs before 37 weeks of gestation. Although respiratory distress syndrome occurs even in a full-term infant, infants born at about 32 weeks or less gestation are at a greatly increased risk of developing respiratory distress syndrome. The risk of neonatal respiratory distress increases with increasing prematurity, and nearly all fetuses at 24 weeks' gestation or less will suffer from the condition. Most fetuses at 24 weeks or less have not yet developed alveoli, so approximately half of fetuses born at this stage will die, even if treated with surfactant therapy and ventilation. Similar gestational dates can be extrapolated for other species, for example, a mouse gestation generally is approximately 19 to 20 days long, and mice born at E17.5 generally exhibit respiratory distress.

Neonatal respiratory distress syndrome is ameliorated or even prevented entirely if mothers at risk for premature delivery receive SCGB3A2. For example, in some embodiments, SCGB3A2 is administered to the mother if delivery is expected within about two weeks, about one week, or even less than a week, for instance within about three days, about two days, about one day, or even if delivery is expected within a matter of hours. Administration of SCGB3A2 to a gestational mother speeds the development of the fetal lungs and hastens their production of surfactant.

Preterm delivery can be predicted when a mother is exhibiting signs of labor, for instance contractions, cervical dilation and/or thinning, or rupture of the amniotic membrane. In addition, the fetal fibronectin test can help predict whether a woman is likely to give birth within the next 7-14 days. A negative result on the fetal fibronectin test means it is highly unlikely that birth will occur within that time frame. A positive result indicates that premature birth is more likely.

If preterm labor is suspected or anticipated, lung maturity of the fetus can be assessed with various tests carried out on the amniotic fluid. For very premature deliveries, or when there is not sufficient time to carry out a test, SCGB3A2 is administered to the mother without first testing the fetal lung maturity. In pregnancies of greater than about 30 weeks, or in a fetus of any gestational age wherein the lung maturity is uncertain, the fetal lung maturity may be tested by sampling the amount of surfactant in the amniotic fluid, obtained by inserting a needle through the mother's abdomen and uterus. Some maternal conditions, such as diabetes, can impact fetal lung maturity such that surfactant production is insufficient, even at 40 weeks' gestation. The 'maturity level' of fetal lungs is expressed as the lecithin-sphingomyelin (or "L/S") ratio. If this ratio is less than two, the fetal lungs may be surfactant deficient, and SCGB3A2 is administered. In some cases, SCGB3A2 is administered together with a glucocorticoid, which also aids in surfactant production.

Administration to subjects in utero is normally accomplished by transplacental administration or amniotic administration. For transplacental administration, the SCGB3A2 is administered to the mother parenterally, for instance by intravenous, intraperitoneal, intramuscular, intra-arterial, or subcutaneous injection or infusion, or by topical administration. In some instances, maternal administration is by inhalation. Generally, however, intravenous administration is appropriate.

An effective amount of SCGB3A2 is administered in a single dose, or in multiple doses, for example weekly, daily, or multiple times daily, during a course of treatment. In one embodiment, a therapeutically effective amount of a SCGB3A2 is administered as a single pulse dose, as a bolus dose, or as pulse doses administered over time. In pulse doses, a bolus administration of a SCGB3A2 is provided, followed by a time period wherein no SCGB3A2 is administered to the subject, followed by a second (and optionally subsequent) bolus administration. In specific, non-limiting examples, pulse doses of SCGB3A2 are administered during the course of a day, or during the course of a week or more, for instance, from the onset of signs of premature labor until delivery.

In other embodiments, SCGB3A2 is used to treat neonatal respiratory distress postnatally. SCGB3A2 is administered to a neonate parenterally (for example, intravenously, intramuscularly, intraperitoneally, intra-arterially, or subcutaneously), or directly to the lungs by inhalation or by endotracheal tube. By way of example, one method of administration to the lungs is by inhalation through the use of a nebulizer or inhaler. For example, the SCGB3A2 is formulated in an aerosol or particulate and drawn into the lungs using a standard nebulizer well known to those skilled in the art. In addition to SCGB3A2, oxygen is given with a small amount of continuous positive airway pressure ("CPAP") in some embodiments, and intravenous fluids are administered to stabilize the blood sugar, blood salts, and blood pressure.

Alternatively, or if the infant's condition worsens, an endotracheal tube (breathing tube) is inserted into the trachea and intermittent breaths are given by a mechanical device. SCGB3A2 is administered via the endotracheal tube, and in some embodiments, an exogenous preparation of surfactant, either synthetic or extracted from animal lungs, is also delivered into the lungs in conjunction with the SCGB3A2. Response to treatment is measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, lung volume, and oxygen saturation. An increase in one or more of these parameters indicates efficacy of the SCGB3A2 treatment.

For both prenatal and postnatal administration of SCGB3A2, an effective dose ranges from about 0.1 mg/kg to about 100 mg/kg of body weight. In one specific, non-limiting example, an effective dose is from about 1 mg/kg to about 20 mg/kg, or in even more particular examples, from about 5 mg/kg to about 10 mg/kg of body weight.

SCGB3A2 to Promote Lung Development

Also disclosed herein is the surprising discovery that the secretory protein SCGB3A2 promotes lung development. In one embodiment of the disclosure, the growth factory activity of SCGB3A2 is exploited for the promotion of lung development in a subject in need thereof. A subject may be in need of lung development, for instance, because they have or are at risk for developing neonatal respiratory distress. Alternatively, a non-neonatal or adult subject may be in need of lung development because they have suffered lung damage or because they have lost all or part of a lung, or have lost all or part of a lung's capacity or function due to disease, accident or surgery.

Administration to the subject is normally accomplished by either parenteral administration, for instance by intravenous, intraperitoneal, intramuscular, intra-arterial, or subcutaneous injection or infusion, or by inhalation or by endotracheal tube. By way of example, one method of administration to the lungs of an individual is by inhalation through the use of a nebulizer or inhaler. For example, the SCGB3A2 is formulated in an aerosol or particulate and drawn into the lungs using a standard nebulizer well known to those skilled in the art.

In some embodiments, a nanoparticle-based drug delivery system is used for direct pulmonary delivery. (For instance, see Pandey et al., (2003) *J. Antimicrobial Chemotherapy* 52, 981-986). The small size of the nanoparticles is advantageous for delivery deep into the lungs (see for instance, Jacobs & Muller (2002) *Pharmaceutical Research* 19, 189-94; Dailey et al., (2003) *J. Controlled Release* 86, 131-44). In some embodiments, poly(DL-lactide-co-glycolide) (PLG) polymers are chosen as the drug carrier because of their biodegradability and biocompatibility (see, for instance, Anderson & Shive (1997) *Advanced Drug Delivery Reviews* 28, 5-24). In other embodiments, gelatin-based or polybutylcyanoacrylate-based nanoparticles are used. Such nanoparticles are delivered using a nebulizer, in some embodiments. Nanoparticle-based drug delivery systems are discussed at greater length below, in Example 16.

An effective amount of SCGB3A2 is administered in a single dose, or in multiple doses, for example daily, during a course of treatment. In one embodiment, a therapeutically effective amount of a SCGB3A2 is administered as a single pulse dose, as a bolus dose, or as pulse doses administered over time. Thus, in pulse doses, a bolus administration of a SCGB3A2 is provided, followed by a time period wherein no SCGB3A2 is administered to the subject, followed by a second bolus administration. In specific, non-limiting examples, pulse doses of SCGB3A2 are administered during the course of a day, during the course of a week, or during the course of a month.

Response to treatment is measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, lung volume, and oxygen saturation. An increase in one or more of these parameters indicates efficacy of the SCGB3A2 treatment.

The methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second (FEV1), allows bronchoconstriction to be quantitatively evaluated. An increase in FVC or FEV1 reflects a decrease in bronchoconstriction, and indicates that SCGB3A2 therapy is effective.

A concern with forced vital capacity determination is that the forced vital capacity maneuver (for instance, forced exhalation from maximum inspiration to maximum expiration) is largely technique-dependent. In other words, a given subject may produce different FVC values during a sequence of consecutive FVC maneuvers. The FEF 25-75 or forced expiratory flow determined over the midportion of a forced exhalation maneuver tends to be less technique dependent than the FVC. Similarly, the FEV1 tends to be less technique-dependent than FVC. Thus, an increase in the FEF 25-75 or FEV1 reflects a decrease in bronchoconstriction, and indicates that SCGB3A2 therapy is effective.

In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest airflow rate in liters per minute during a forced maximal exhalation, is well correlated with overall pulmonary function in a patient with pulmonary fibrosis and other respiratory diseases. Thus, an increase in the peak expiratory flow following administration of SCGB3A2 indicates that the therapy is effective.

An effective dose ranges from about 0.1 mg/kg to about 100 mg/kg of body weight. In one specific, non-limiting example, an effective dose is from about 1 mg/kg to about 20 mg/kg, or in even more particular examples, from about 5 mg/kg to about 10 mg/kg of body weight. In some embodiments, the SCGB3A2 is administered to the subject in com-

SCGB3A2 to Inhibit Lung Damage Caused by Anti-Cancer Agents

The effect of SCGB3A2 on bleomycin-induced DNA damage was examined using primary murine fetal lung mesenchymal cells in vitro and a mouse model for bleomycin-induced fibrosis in vivo. In both cases, SCGB3A2 repaired or suppressed bleomycin-induced DNA damage/fibrosis when given together with or prior to bleomycin treatment, respectively. In addition, SCGB3A2 repaired or suppressed bleomycin-induced fibrosis when administered up to two, three, or even four weeks after the commencement of bleomycin treatment. Thus, SCGB3A2 is useful for treating, reducing, and preventing the lung damage caused by bleomycin and other cytotoxic antibiotic antineoplastic agents.

Thus, in yet another embodiment of the disclosure, the anti-apoptotic activity of SCGB3A2 is exploited for the prevention or reduction or reversal (repair) of lung damage in a subject treated with an anti-cancer agent such as a cytotoxic antibiotic. Administration to such a subject is normally accomplished by parenteral administration, for instance by intravenous, intraperitoneal, intramuscular, intra-arterial, or subcutaneous injection or infusion, or by inhalation or by endotracheal tube. By way of example, one method of administration to the lungs of an individual is by inhalation through the use of a nebulizer or inhaler. For example, the SCGB3A2 is formulated in an aerosol or particulate and drawn into the lungs using a standard nebulizer well known to those skilled in the art.

In some embodiments, a nanoparticle-based drug delivery system is used for direct pulmonary delivery. Such nanoparticles are, in some embodiments, poly(DL-lactide-co-glycolide)-based, gelatin-based, or polybutylacrylate-based nanoparticles. Nanoparticle delivery systems are described in greater detail below in Example 16.

As described above, an effective amount of SCGB3A2 is administered in a single dose, or in multiple doses, for example daily, during a course of treatment, or as a single pulse dose, as a bolus dose, or as pulse doses administered over time.

Response to treatment is measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, lung volume, and oxygen saturation. An increase in one or more of these parameters indicates efficacy of the SCGB3A2 treatment. These methods and their relative advantages and disadvantages are described elsewhere in greater detail.

An effective dose ranges from about 0.1 mg/kg to about 100 mg/kg of body weight. In one specific, non-limiting example, an effective dose is from about 1 mg/kg to about 20 mg/kg, or in even more particular examples, from about 5 mg/kg to about 10 mg/kg of body weight, based on efficacy. In some embodiments, the SCGB3A2 is administered to the subject in combination with one or more other drugs, such as one or more anti-cancer agents, bronchodilators, expectorants, or steroids.

In Vitro Use of SCGB3A2

In some embodiments, SCGB3A2 is used in vitro as a growth factor and/or anti-apoptotic agent, as well as in the study of lung development and the mechanisms of drug-induced DNA damage. For example, recombinant SCGB3A2 is useful for the study of the mechanisms of lung branching morphogenesis, as well as SCGB3A2's anti-apoptotic function against DNA damage caused by bleomycin.

Lung development is regulated by many transcription factors including the zinc finger transcription factors Gli1, 2 and 3. TITF1/NKX2.1, FOXA2/HNF-3β and GATA-6 (see, for instance, Hui et al. (1998) *Dev. Biol.* 162: 402-413; Motoyama et al. (1998) *Nat. Genet.* 20: 54-57; Ang & Rossant, (1994) *Cell* 78: 561-574; Kimura et al. (1996) *Genes Dev.* 10: 60-69; Perl & Whitsett (1999) *Clin. Genet.* 56: 14-27; Liu et al. (2002) *Am. J. Physiol. Lung Cell. Mol. Physiol.* 283: L468-475). Further, several growth factors and morphogens such as fibroblast growth factor (FGF) 10, sonic hedge hog (SHH) and bone morphologic protein (BMP) 4 have been shown to play a role in lung development (Bellusci et al. (1996) *Development* 122: 1693-170; Litingtung et al. (1998) *Nat. Genet.* 20: 58-61; Perl & Whitsett (1999) *Clin. Genet.* 56: 14-27; Sekine et al. (1999) *Nat. Genet.* 21: 138-141; Cardoso (2001) *Annu. Rev. Physiol.* 63: 471-494). However, the mechanisms how the activities of these factors relate to each other in promoting branching morphogenesis are not fully understood.

Since SCGB3A2 also influences lung branching morphogenesis (as described herein), understanding how SCGB3A2 affects expression of other factors and participates branching morphogenesis provides a clearer view of the mechanisms of lung branching morphogenesis. For instance, in embryonic lung organ cultures, addition of SCGB3A2 into the media increased mesenchymal cells and the expression levels of FGFs, when examined by RT-PCR.

In order to elucidate the exact location of increased expression and the effects of SCGB3A2 on the expression levels and patterns of other growth factors such as SHH and BMP, for example, various amount of recombinant SCGB3A2 is added to the media of cultures of embryonic lung organ, lung primary cells or cell lines. The levels and/or locations of expression of other growth factors are examined and compared in the presence and absence of SCGB3A2 by quantitative PCR, in situ hybridization, and/or immunohistochemistry. Further, in some embodiments, recombinant SCGB3A2 is bound to beads and placed onto a portion of lung tissue in organ culture. This is particularly useful for elucidating and clarifying the effects of SCGB3A2 on lung branching because the technique restricts the effect of SCGB3A2 to a very small area, compared to the addition of SCGB3A2 to culture media, which affects the entire organ culture.

The influence of SCGB3A2 on the expression levels and patterns of other factors, and how these factors participate in lung branching morphogenesis, is then demonstrated by morphological observation, whole mount hybridization, in situ hybridization, and/or immunohistochemistry. The use of growth factor-bound beads in the study of lung development has been described for BMP4 and FGF10 (Lebeche et al. (1999) *Mech. Dev.* 86: 125-136; Weaver et al. (2000) *Development* 127: 2695-2704).

Similarly, recombinant SCGB3A2 is used to elucidate the anti-apoptotic activity of SCGB3A2 by its addition to culture media of embryonic lung organ, lung primary cells or cell lines together, before or after addition of bleomycin. Tissues and/or cells are subjected to microarray and/or protein array analysis, quantitative PCR, northern and/or Western analysis to determine which anti-apoptotic pathway interacts with bleomycin-induced DNA damage pathway.

In other embodiments, SCGB3A2 is used to treat lung cells or lung tissue in vitro, for instance for transplantation into immature, damaged, or diseased lungs. Once transplanted, these cells and/or tissues are used to rebuild or repair the lung damage in vivo. In one embodiment, the lung cell is a stem cell or progenitor cell. The subject of lung epithelial stem cells has been reviewed comprehensively (see, for instance, Rawlins & Hogan (2006) *Development* 133, 2455-2465; Neuringer & Randall (2004) *Respir. Res.* 5,6; Neuringer & Randall (2006) *Monaldi Arch. Chest Dis.* 65, 47-51). Both basal and columnar cells have been shown to reconstitute a complete lung epithelium in an in vivo model of denuded tracheas (see, for instance, Liu et al. (1994) *Am. J. Physiol.* 266, L296-L307; Avril-Delplanque et al. (2005) *Stem Cells* 23, 992-1001), and in some species, basal tracheal cells have the ability to form large differentiated epithelial colonies (see, for instance. Hong et al. (2004) *Am. J. Physiol.* 164, L631-L649). Additionally, Clara cells may be considered stem or progenitor cells because they proliferate to restore the bronchiolar epithelium following injury by oxidant gases (see, for instance, Evans et al. (1986) *Am. J. Pathol.* 123, 126-133). In general, the lung cells are isolated from a donor airway epithelium, and are dissociated and seeded onto membranes and cultured at the air-liquid interface (see, for instance, Schoch et al. (2004) *Am. J. Physiol. Lung Cell Mol. Physiol.* 286, L631-L642) in the presence of about 10 ng-10 mg/ml SCGB3A2.

In other embodiments, lung tissue explants are grown in the presence of about 10 ng-10 mg/ml SCGB3A2 in order to prepare the lung tissue for transplantation into an area of diseased or damaged lung tissue. Briefly, in one embodiment, lung tissue is isolated from a donor and cultured in DMEM/F12 containing 10% FBS on a 0.4 µm pore membrane (for instance, Millipore Corporation, Billerica, Mass.), which is placed on the top of steel wire mesh in an organ culture dish (for instance, Becton Dickinson, Franklin Lake, N.J.). Lung explants are then incubated with SCGB3A2 and cultured for two to four days or more at 37° C. in a 5% humidified 95% $CO_2$ air incubator. Every day or every two days, media and the additives (SCGB3A2) are replaced. Once the lung explants have reached the desired size and/or maturity, they are transplanted into an area of diseased or damaged lung.

In other embodiments, lung cells are grown on poly-DL-lactic acid scaffolds in order to engineer lung tissue for transplant (see, for instance, Lin et al. (2006) *J. Biomaterials Applications* 21, 109-118). Poly-DL-lactic acid (PDLLA) is a well-known super-high molecular-weight acid that has good biocompatibility and degrades following in vivo implantation (see, for instance, Lee & Gardella (2002) *Analytical and Bioanalytical Chem.*, 373(7): 526-537). It has been previously shown that PDLLA, alone or as a composite, supports the growth of osteoblasts, chondrocytes, and lung carcinoma cells (see, for instance, Roether et al. (2002) *Biomaterials*, 23(18): 387-392; Blaker et al., (2003) *J. Biomed. Mater. Res.*, 67A(4): 1401-1406; Verrier et al. (2004) *Biomaterials*, 25(15): 3013-3017; Maquet et al., (2004) *Biomaterials*, 25(18): 4185-4189). These features, plus the intrinsic adequate elastic properties and flexibility of PDLLA, make this biodegradable polymer suitable for lung tissue engineering (see, for instance, Lin et al. (2006) *J. Biomaterials Applications* 21, 109-118). Methods of culturing lung cells on PDDLA membranes are discussed at greater length in Example 17, below.

Pharmaceutical Compositions that Include SCGB3A2

SCGB3A2 may be formulated in a variety of ways, depending in part on the type of disease or condition to be treated. Pharmaceutical compositions are provided for both inhalational use and for systemic use, by way of example. The disclosure includes within its scope pharmaceutical compositions comprising SCGB3A2 formulated (or an equivalent thereof) for use in human or veterinary medicine. While SCGB3A2 will typically be used to treat human subjects, it also may be used to treat similar or identical diseases in other vertebrates, such other primates, sheep, chimpanzees, mice, dogs, cats, horses, and cows.

Pharmaceutical compositions that include SCGB3A2 as an active ingredient, or that include both SCGB3A2 and an additional respiratory agent as active ingredients, may be formulated with an appropriate solid or liquid carrier, depending upon the particular mode of administration chosen. Additional active ingredients include, for example, anti-infective agents, anti-inflammatory agents, bronchodilators, enzymes, expectorants, steroids, and anti-cancer agents. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988.

The dosage form of the pharmaceutical composition will be determined by the mode of administration chosen. For instance, in addition to injectable fluids, inhalational formulations are employed in some embodiments. Inhalational preparations include aerosols, particulates, and the like. In general, the goal for particle size for inhalation is about 1 µm or less in order that the pharmaceutical reach the alveolar region of the lung for absorption. Actual methods of preparing such dosage forms are known, or will be apparent, to those of ordinary skill in the art.

The compositions or pharmaceutical compositions can be administered by any route, including parenteral administration, for example, subcutaneous, intravenous, intra-arterial, intraperitoneal, intramuscular, intraperitoneal, or intramuscular injection or infusion, or by pulmonary inhalation. When SCGB3A2 is provided as parenteral compositions, for instance for injection or infusion, it is generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

For administration by inhalation, the compounds for use according to the present disclosure are conveniently delivered in the form of an aerosol spray presentation from pressurized packs or a nebulizer, with the use of a suitable propellant, for instance, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

In some embodiments, a nanoparticle-based drug delivery system is used for direct pulmonary delivery. For instance, poly(DL-lactide-co-glycolide) (PLG) polymers are chosen as the drug carrier because of their biodegradability and biocompatibility (see, for instance, Anderson & Shive (1997)

*Advanced Drug Delivery Reviews* 28, 5-24). In some examples, PLG nanoparticles are prepared using a multiple emulsion technique described by Lamprecht et al. ((1999) *International Journal of Pharmaceutics* 184, 97-105). The PLG nanoparticles encapsulate the SCGB3A2, and the nanoparticles are administered using a nebulizer.

In other embodiments, the nanoparticles are made from mannitol, lactose, gelatin, or polybutylcyanoacrylate (see, for instance, Sham et al. (2004) *International Journal of Pharmaceutics* 269, 457-467). To prepare inhalable nanoparticle powders, spray-drying is a commonly practiced method (see, for instance, Bosquillon et al. (2001) *J. Control. Release* 70, 329-339; Mackin et al. (1997) *Pharm. Sci.* 3, 583-586; Vanbever et al. (1999) *Pharm. Res.* 16, 1735-1742). Exemplary methods for the preparation of gelatin nanoparticles can be found in Sham et al. (2004) *Int. J. Pharma.* 269, 457-467 and Coester et al. (2000) *J. Microencapsul.* 17, 187-193, and are described below in Example 16.

Without further elaboration, it is believed that one skilled in the art can, using this description, utilize the present discoveries to their fullest extent. The following examples are illustrative only, and not limiting of the disclosure in any way whatsoever.

Example 1

Materials and Methods Used for SCGB3A2 Protein and Animal Studies

This Example illustrates specific methods used to carry out the experiments described in Examples 2-14, below.

SCGB3A2 Protein

Two kinds of recombinant mouse SCGB3A2 protein were used that were obtained using a bacterial expression plasmid pET32a-Trx (thioredoxin)-His (histidine)-SCGB3A2 (pET32a from Novagen, San Diego, Calif.) and pDest-544-His6-NusA (N utilization substance protein A)-TEV (Tobacco Etch Virus)-SCGB3A2. In these expression plasmids, a mouse SCGB3A2 cDNA sequence excluding the region encoding the signal peptide (from +155 to +443) was used. Trx-His-tagged recombinant SCGB3A2 protein was produced in BL21 by inducing with isopropyl-β-D-thiogalactopyranosid (IPTG) and was purified by a Ni-NTA Spin Columns (Qiagen, Valencia, Calif.) or TALON Superflow Metal Affinity Resin (BD Biosciences, Palo Alto, Calif.). His6-NusA-TEV-SCGB3A2 protein was produced in Rosetta (DE3) cells (Novagen), which was then subjected to extensive purification steps including TEV protease digestion. The Trx-His-recombinant SCGB32 was used for all ex vivo and cell culture studies whereas highly purified tag-free, endotoxin-free (endotoxin level 0.2 EU/mg) SCGB3A2 was used for all animal studies. Mice received intravenous injection of up to total of 200 μg of SCGB3A2 via the tail vein (less than 5 EU/kg of the maximum endotoxin allowed). All animal studies were carried out in accordance with the Using Animals in Intramural Research Guidelines (NIH Animal Research Advisory Committee, NIH, Bethesda, Md.) after approval by the NCI Animal Care and Use Committee.

Organ Culture

Fetal lungs were isolated from pregnant female mice at E11.5-12.0 or E16.5. Lungs were cultured in DMEM/F12 containing 10% FBS on a 0.4 μm pore membrane (Millipore Corporation, Billerica, Mass.), which was placed on the top of steel wire mesh in an organ culture dish (Becton Dickinson, Franklin Lake, N.J.). Lungs were incubated with various additives as indicated, or transfected with Rad23b or negative siRNA probe using HiPerFect Transfection Reagent (Qiagen, Valencia. Calif.), and cultured for two to four days at 37° C. in a 5% humidified 95% $CO_2$ air incubator. Every two days, media and the additives were changed. Experiments were performed using more than three lungs per condition per a given occasion, and were repeated 3-10 times.

Rad23b siRNA Probes:

Rad23b siRNA probes1 and 2 have the following sequences: Probe 1,5'-GUA GCA GGU CAG AAG UUA A-3' (sense; SEQ ID NO: 1) and 5'-UUA ACU UCU GAC CUG CUA C-3' (antisense; SEQ ID NO: 2); Probe 2,5'-GCU UCA CAU UAG UAU GAG A-3' (sense; SEQ ID NO: 3) and 5'-UCU CAU ACU AAU GUG AAG C-3' (antisense; SEQ ID NO: 4); negative siRNA, 5'-UUC UCC GAA CGU GUC ACG U-3' (sense; SEQ ID NO: 5) and 5'-ACG UGA CAC GUU CGG AGA A-3' (antisense; SEQ ID NO: 6).

Histological Analysis

Lungs were fixed in 4% paraformaldehyde (PFA) overnight at 4° C. and embedded in paraffin or O.C.T. Compound (SAKURA, Torrance, Calif.). Immunohistochemistry and in situ hybridization were carried out as previously described (Chiba et al., (2006) *Am. J. Respir. Crit. Care Med May* 1; 173(9):958-64; Srisodsai et al., (2004) *J. Biol. Chem.* 279, 54358-54368) using 4 μm sections. Antibodies used for immunocytochemistry and immunohistochemistry are as follows: anti-histidine (Penta-His antibody, QIAGEN, Valencia, Calif.), anti-thioredoxin (Invitrogen, Carlsbad, Calif.), anti-MARCO (Serotec, Raleigh, N.C.), anti-TITF1 (DAKO, Carpinteria, Calif.), anti-phospho-histone H3 (Upstate, Lake Placid, N.Y.), and anti-Ki-67 (GeneTex, San Antonio, Tex.). Anti-SCGB3A2 antibody was as previously described (Niimi et al., (2001)*Mol. Endocrinol.* 15, 2021-2036). Cells for positive immunostaining were counted using five areas each (×400 magnification) randomly chosen, from three sections of in vivo tissues and five sections of ex vivo tissues. The number obtained was expressed as a percentage of the total cells.

Breathing Scores

The E17.5 pups from PBS, 100 μg SCGB3A2, or 200 μg SCGB3A2-treated groups were subjected to measurement of breathing scores. The pups removed from the mothers were placed on moistened filter paper at 37° C. Each pup's breathing motion was observed for two minutes by two independent investigators. Scoring assignment was carried out according to the criteria described by Ozdemir et al. (*Pediatr. Res.* 53, 98-103 (2003)) as follows: respiratory pattern 0=no breathing; 1=gasping; 2=gasping/labored breathing; 3=labored breathing; 4=labored breathing/unlabored breathing; 5=unlabored breathing. Gasping was characterized as isolated breathing with the mouth opened and the neck extended. Labored breathing involved abdominal and extremity movement, whereas unlabored breathing required chest motion only (Ozdemir et al. (2003) *Pediatr. Res.* 53, 98-103).

RT-PCR and Quantitative PCR Analysis

Quantitative RT-PCR was performed by SYBR Green master mixture and analyzed with ABI Prism 7900 Sequence Detection System (Applied Biosystems, Foster City, Calif.). The following primers were used for both RT-PCR and quantitative PCR: Rad23b, (forward) 5'-GGA GGA GAC GGT AAA GGC ATT G-3' (SEQ ID NO: 7), (reverse) 5'-TGG GGA AGA ACT GAC TGT AGT GGG-3' (SEQ ID NO: 8); FGF2, (forward) 5'-ATG AAG GAA GAT GGA CGG CTG-3' (SEQ ID NO: 9), (reverse) 5-CCA GTT CGT TTC AGT GCC ACA-3' (SEQ ID NO: 10); FGF7, (forward) 5'-AAG ACT GTT CTG TCG CAC CCA-3' (SEQ ID NO: 11), (reverse) 5'-GCC ACA ATT CCA ACT GCC A-3' (SEQ ID NO: 12); FGF9, (forward) 5'-CTA CCT CGG CAT GAA CGA GAA-3' (SEQ ID NO: 13), (reverse) 5'-ATC TCC TTC CGG TGT CCA CAT-3' (SEQ ID NO: 14); FGF10, (forward) 5'-TTT GGT GTC TTC GTT CCC TGT-3' (SEQ ID NO: 15), (reverse) 5'-AGG TGA TTG TAG CTC CGC ACA-3' (SEQ ID NO: 16); 18S, (forward) 5'-CGG CTA CCA CAT CCA AGG AA-3' (SEQ ID NO: 17), (reverse) 5'-ATTGGAGCTG-GAATTACCGC-3' (SEQ ID NO: 18); SP-A, (forward) 5'-TAA GAA GCC AGA GAA CCA GGT AGG-3' (SEQ ID NO: 23), (reverse) 5'-CTC AGT GAT GTA AAG TGG ACG AAG G-3' (SEQ ID NO: 24); SP-D, (forward) 5'-TTT GAG GAT GCC CAG GAG ATG TGC-3' (SEQ ID NO: 25), (reverse) 5'-AGG AAA GCA GCC TTG TTG TGG-3' (SEQ ID NO: 26); AQP1, (forward) 5'-GCT CAC CCG CAA CTT CTC AAA C-3' (SEQ ID NO: 27), (reverse) 5'-TCA GCA TCC AGG TCA TAC TCC TCC-3' (SEQ ID NO: 28); OB-R, (forward) 5'-AGG AAT CGT TCT GCA AAT CCA-3' (SEQ ID NO: 29), (reverse) 5'-TAT GCC AGG TTA AGT GCA GCT ATC-3' (SEQ ID NO: 30).

Unless otherwise specifically noted in particular Examples below, the conditions used for RT-PCR were 94° C., 5 minutes, followed by 94° C. for 15 seconds, 60° C. or 62° C. (for Rad23b) for 15 seconds, 72° C. for 30 seconds, 72° C. for five minutes for 25-28 cycles depending on gene, and for quantitative PCR, 50° C. for 2 minutes, 95° C. for 10 minutes, followed by 95° C. for 15 seconds, 60 or 62° C. (for Rad23b) for 40 seconds for 45 cycles. The standard curve method was used and all data were normalized to 18S rRNA.

Construction of pDest-544-His6-NusA-TEV-SCGB3A2 pDonr223 is a Gateway Donor vector modified from pDonr201 (Invitrogen). In pDonr223, the kanamycin resistance gene is replaced with a gene encoding spectinomycin resistance, and several sequencing primer sites have been added to aid in sequence verification of Entry clones. pDest-544 is a Gateway Destination vector generated by modification of pET-43b (Novagen, Inc), which contains a T7 promoter and an amino-terminal His6-NusA fusion tag. The following oligonucleotides (Operon, Inc) were used in this study: L2575, 5'-GGC GAA AAC CTG TAC TTC CAA GGC ATG CTT CTC ATC AAC CGT CTC CCT GTT GTT GAC-3' (SEQ ID NO: 19); L2576, 5'-GGG GAC AAC TTT GTA CAA GAA AGT TGG CTA TAC CAG GTG TGA AAG AGC CTC C-3' (SEQ ID NO: 20); L907, 5'-GGG GAC AAC TTT GTA CAA AAA AGT TGG CGA AAA CCT GTA CTT CCA AGG C-3' (SEQ ID NO: 21).

A SCGB3A2 cDNA fragment used to construct pDest-544-His6-NusA-TEV-SCGB3A2 was first amplified using 95° C. for two minutes, followed by five cycles of 95° C. for 30 seconds, 55° C. for 45 seconds, and 72° C. for 60 seconds with 200 nM each of primers L2575 (SEQ ID NO: 19) and L2576 (SEQ ID NO: 20), and the original SCGB3A2 cDNA clone (Niimi et al. (2001) *Mol. Endocrinol.* 15, 2021-2036; clone #12). Following this, 200 nM of adapter primer L907 (SEQ ID NO: 21) was added, and 15 more cycles of amplification were carried out using the same cycling parameters with Platinum Taq HiFidelity (Invitrogen). All cycling was done on an Applied Biosystems 9700 cycler. After cycling, a 72° C., five minute incubation was carried out to extend PCR products, followed by cooling to 4° C. The final PCR product contains the mature form of the SCGB3A2 gene (starting at amino acid 22 of the full-length protein sequence) flanked on the 5' side with a Gateway attB1 site and Tobacco Etch Virus (TEV) protease cleavage site. The 3' side contains a Gateway attB2 recombination site. The PCR products were cleaned with the QiaQuick PCR purification kit (Qiagen), and recombined into pDonr223 by Gateway BP recombination (Invitrogen) using the manufacturer's protocols. The subsequent Entry clone was sequence verified, and subcloned by Gateway LR recombination into pDest-544. The final expression clone (3152-X1-544) encodes a protein of the form His6-NusA-TEV-SCGB3A2 mature. The linker between the fusion tag and the SCGB3A2 gene consists of the amino acid sequence ENLYFQG (SEQ ID NO: 22), which is cleaved by Tev protease between the Q and G residues to leave only a single glycine at the aminoterminus of the mature SCGB3A2 gene.

Expression of His6-NusA-TEV-SCGB3A2

The expression clone was transformed into *E. coli* Rosetta (DE3) cells (Novagen). Five ml of an overnight culture grown at 37° C. in CircleGrow medium (Qbiogene) containing 100 μg/ml ampicillin and 15 μg/ml chloramphenicol were used to innoculate a four-liter baffled shake flask containing one liter of LB medium with the same antibiotics. After incubation at 37° C. at 200 rpm for seven hours, 450 ml of this seed culture ($OD_{600}$=2.10) were added to a 20 liter New Brunswick Scientific BioFlo IV fermenter containing 15 liters of modified Studier ZYM5052 medium, whose final composition was 1% N-Z-amine AS, 0.5% yeast extract, 25 mM $Na_2HPO_4$, 25 mM $KH_2PO_4$, 50 mM $NH_4Cl$, 5 mM $Na_2SO_4$, 2 mM $MgSO_4$, 1 mM trisodium citrate, 0.2× trace metals, 2% glycerol, 0.05% glucose, 0.2% α-lactose, 25 mM succinic acid, 100 μg/mL ampicillin, and 15 μg/mL chloramphenicol. This medium corresponds to ZYP5052 with the following adjustments: salts were at half concentration, glycerol was increased from 0.5 to 2% to increase cell yield, and succinic acid was added to stabilize pH. Cells were grown at 37° C. with monitoring (but without control) of pH but without supplemental feeding, and dissolved oxygen was maintained at 40%. After five hours ($A_{600}$=5.19), the temperature was reduced to 20° C. and growth continued until harvest at 18 hours (stationary phase was reached at 16 hours, final $A_{600}$=24.0, final pH 5.42). Cells ($3.6 \times 10^5$ $A_{600}$ units, 626 grams wet weight) were harvested and stored at −80° until use.

Non-Denaturing Purification by Immobilized Metal Ion Affinity Chromatography (IMAC)

*E. coli* cell pastes were resuspended with four volumes of extraction buffer (for a final concentration of 20 mM HEPES, pH 7.3, 100 mM NaCl, 5 mM $MgCl_2$, 5% glycerol, 45 mM imidazole, and Complete protease inhibitor as per the manufacturer's instructions, Roche) per gram wet weight, digested with lysozyme (0.5 mg/ml, Sigma) for 30 minutes on ice and treated with 10 U Benzonase (Novagen)/ml for an additional 20 minutes. The sample was sonicated to lyse the cells using a Branson Digital Sonifier 450 (100% power, 33% duty cycle, for 3×20 sec with a 1 cm tip) and lysis was verified by microscopic examination. The lysate was adjusted to 500 mM NaCl, clarified by centrifugation at 111,000×g for 30 minutes, filtered (0.45 PES membrane) and applied to HisTrap columns (GE Healthcare) equilibrated with extraction buffer in 500 mM NaCl and 45 mM imidazole (binding buffer). The columns were washed with binding buffer to baseline, proteins eluted over 20 column volume (CV) gradients to 400 mM imidazole.

TEV Protease Digestion and Subsequent Purification

The pool created from the IMAC was dialyzed against binding buffer without additional imidazole and treated with TEV protease (3% v/v with a 5 mg/ml lab stock) at room temperature for four hours and then shifted to 16° C. overnight and analyzed by SDS-PAGE. An additional IMAC step similar to the initial IMAC was used to purify the target protein away from the contaminants of the protease digest.

Ion-Exchange Chromatography

A protein sample was dialyzed against 20 mM HEPES, pH 7.3, 100 mM NaCl and 5% glycerol and applied to Q Sepharose resin in pre-poured columns (GE Healthcare) using a chromatography workstation (AKTA-Purifier, GE Healthcare) made endotoxin free by cleaning with 0.01% Triton X-114 (Sigma). Proteins were eluted with a 0.1 to 1M NaCl gradient over 20 CV. At each purification step, fractions were analyzed by SDS-PAGE, and tested for endotoxin levels. The final endotoxin levels were determined by Cambrex Bio Science (Walkersville, Md.).

Samples were then dialyzed twice for at least four hours at 4° C. against at least 20 sample volumes of final buffer using 3.5K MWCO Snakeskin (Pierce) dialysis membrane. When necessary, samples were concentrated using 5K MWCO Amicon Ultra filtration devices (Millipore).

5-Bromo-2'-deoxyuridine Incorporation

5-Bromo-2'-deoxyuridine (BrdU) was directly added to the culture medium of fetal lung primary cells to achieve a final concentration of 10 µM, and cells were incubated for one hour at 37 C.°. Cells were then trypsinized and fixed in 75% ethanol for 24 hours. Fixed cells were treated with 1 ml of 2N HCl containing 0.5% triton X-100 at room temperature for 30 minutes and neutralized with 1 ml of 0.1 M $Na_2B_4O_7 \cdot 10H_2O$, PH 8.5. The cells were centrifuged and suspended in 1 ml of PBS containing 0.5% Tween 20 and 1% BSA, and incubated for 30 minutes at room temperature with 20 µl of Anti-BrdU FITC (Becton Dickinson, San Jose, Calif.), followed by centrifugation and resuspension in 1 ml of PBS containing 5 µg/ml pf propidium iodide (BD Biosciences Pharmingen, San Diego, Calif.). Measurement of red (DNA content) and green (BrdU) fluorescence was determined by flow cytometry.

Flow Cytometric Analysis

Cells were analyzed using a single laser FACS Calibur cytometer (Becton Dickinson, San Jose, Calif.) with excitation at 488 nm. The data were collected and analyzed employing CellQuest Software. The red fluorescent signals (DNA content) were analyzed on a linear scale and the green signals (BrdU) were analyzed on a logarithmic scale. The data are presented as a percentage of the total population exhibiting the fluorescence signal of interest. For each sample, 10,000 cells were analyzed.

DNA Microarray

Titf1-null lungs at E16.5 were cultured in an organ culture system with or without 250 ng/ml SCGB3A2 protein for four days. Total RNAs from these lungs were isolated by TRIzol (Invitrogen, Carlsbad, Calif.) and then incubated with DNase I (Ambion, Austin, Tex.) for 20 minutes at 37° C. RNAs were amplified using MessageAmp aRNA Kit (Ambion, Austin, Tex.), and amplified RNAs were reverse-transcribed to label with Cy3 and Cy5 (GE Healthcare Life Sciences, Piscataway, N.J.) using FairPlay Microarray Labeling Kit (Stratagene, La Jolla, Calif.). Ten mouse arrays (42.2 K) obtained from the NCI Microarray Facility were used for this experiment. Experiments and analysis were performed according to the manufacturer's instructions and the protocol of the Center for Cancer Research, NCI.

Example 2

Effect of SCGB3A2 on Branching Morphogenesis in Fetal Lung

This Example demonstrates that SCGB3A2 increases branching morphogenesis in fetal lung explant cultures.

SCGB3A2 expression was detected by immunohistochemistry, albeit at low levels in the epithelial cells of E11.5 and 13.5 normal fetal lungs (FIG. 1A), where TITF1 that regulates SCGB3A2 is expressed (FIG. 1B). In the E 13.5 lungs, the expression was particularly evident in the growing tips of the bronchi. To determine a possible role for SCGB3A2 in the early embryonic stages of lung development, lungs from E11.5-12.0 embryos were subjected to ex vivo organ culture with and without recombinant SCGB3A2 protein. The recombinant SCGB3A2 contained thioredoxin and histidine tags as a fusion protein at the N-terminus of SCGB3A2. This fusion recombinant protein was immunoreactive with anti-SCGB3A2 antibody, and was used for all ex vivo and cell culture studies. For in vivo studies, SCGB3A2 used was highly purified, tag-free, and endotoxin-free.

After four days of culture, normal fetal lung harvested at E11.5 (FIG. 1C) exhibited some degree of branching morphogenesis (FIG. 1D). Branching was facilitated by the addition of 50 (FIG. 1E) or 250 ng/ml (FIG. 1F) SCGB3A2, which induced 1-2 and 2-3 additional branchings, respectively in comparison to control. Addition of 2% SCGB3A2-specific antiserum in the culture media together with SCGB3A2 protein inhibited the effect of SCGB3A2 (FIGS. 1G and 1H). Lung treated with pre-immune serum proceeded with a similar degree of branching to control, indicating that serum itself does not influence branching (FIG. 1I). Further, anti-SCGB3A2 antiserum delayed branching, likely due to its absorption of endogenously produced SCGB3A2 that was secreted into the culture media (FIG. 1J).

Example 3

SCGB3A2 Promotes Branching Morphogenesis in Titf1-Null Lung

This Example demonstrates that SCGB3A2 promotes branching in lungs from Titf1-null mice and produces a recovery of the epithelial characteristics of Titf1-null mouse trachea and lung similar to those found in wild-type mice.

Figure 2:
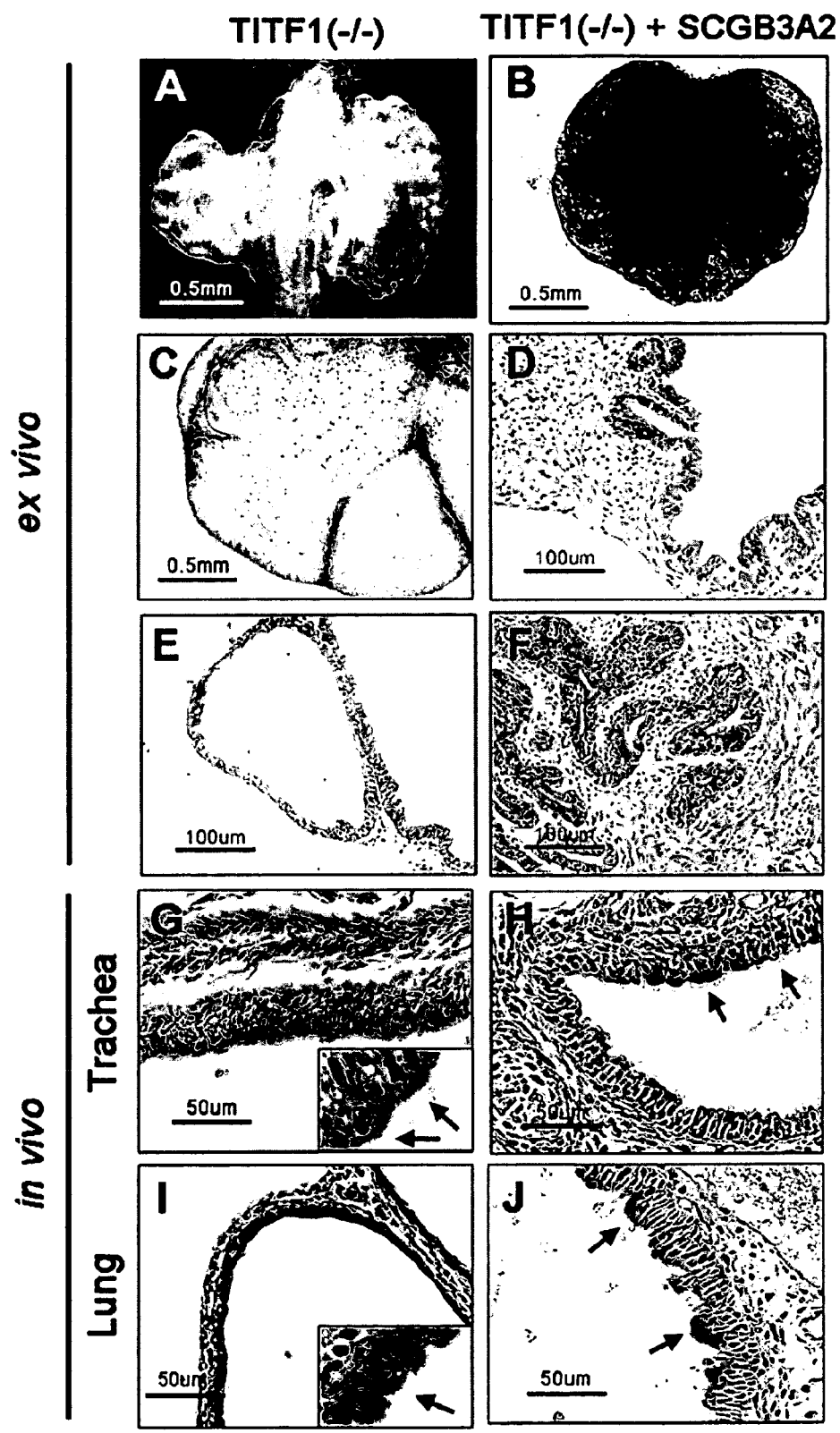
FIG. 2 is a series of digital images showing morphological changes of E16.5 Titf1-null fetal lungs in the presence of SCGB3A2.

Titf1-null lungs exhibit vacuolar lobes consisting of rudimentary bronchi with lean mesenchymal layers (FIG. 2A). Based on the hypothesis that the arrest of branching and development in Titf1-null lungs is at least partly due to a deficiency of SCGB3A2, the effect of SCGB3A2 on Titf1-null lung development was investigated ex vivo and in vivo. After culturing for four days ex vivo, E16.5 Titf1-null lung displayed distended morphology (FIG. 2C), consisting of one layer of epithelia and one layer of mesenchyme (FIG. 2E). Upon the addition of SCGB3A2, however, a drastic morphological change took place. Many pleated structures were observed in SCGB3A2-stimulated Titf1-null lungs (FIG. 2B), consisting of pleated and/or dentate epithelia and duct-like structures with increased layers of mesenchyme (FIGS. 2D and 2F). These data indicate that SCGB3A2 induced branching in Titf1-null lung ex vivo.

The epithelia of trachea and lung in Titf1-null mice were comprised of one to two layers of columnar epithelial cells covered with flattened epithelial and few ciliated cells (FIGS. 2G and 2I). When SCGB3A2 was administered to Titf1-heterozygous females carrying null fetuses, stratified columnar cells with cilia appeared throughout the epithelia of the trachea and lung of Titf1-null fetuses (FIGS. 2H and 2J). These data indicate that SCGB3A2 promotes fetal lung development.

Example 4

SCGB3A2 Induces Proliferation in Titf1-Null Trachea and Lung

This Example demonstrates that the phenotypes produced by SCGB3A2-treatment of trachea and lungs from Titf1-null mice are caused by increased cell proliferation.

Figure 7:
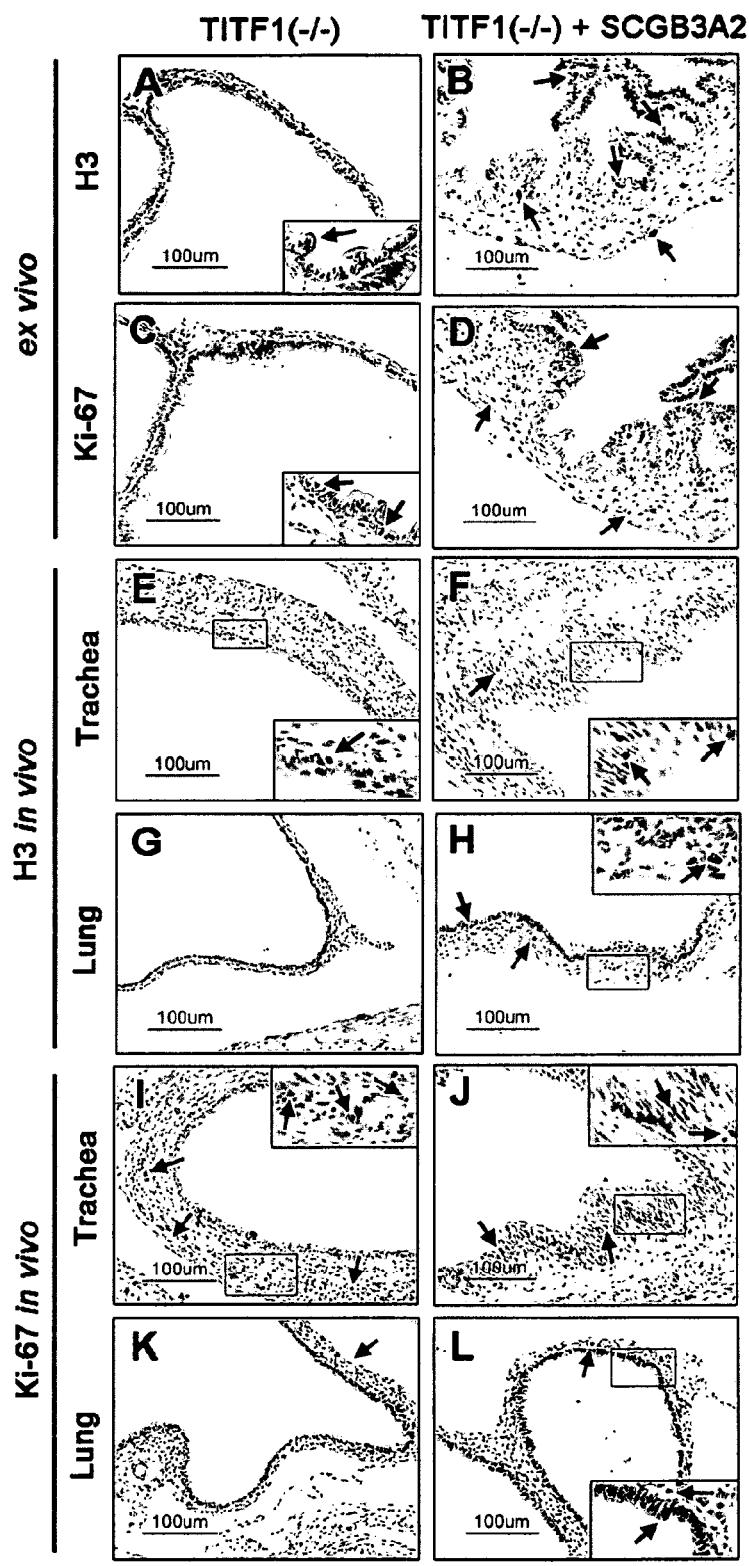
FIG. 7 is a series of digital images showing immunohistochemistry for phosphorylated histone H3 and Ki-67.

To examine whether increased proliferation is responsible for the phenotypes observed in the Titf1-null lungs and trachea by SCGB3A2 treatment, the expression of phosphorylated histone H3 as a mitosis marker and Ki-67 as a proliferation marker, was examined by immunohistochemistry using Titf1-null mice with and without SCGB3A2. In ex vivo cultured Titf1-null lungs as well as lung and trachea of Titf1-null mice, both phosphorylated histone H3 and Ki-67 were very weakly expressed without SCGB3A2 in both epithelial and mesenchymal cells (see, e.g., FIG. 7). Upon administration of SCGB3A2, the expression of phosphorylated histone H3 and Ki-67 were markedly enhanced, in most cases with statistically significant differences as determined by positive cell numbers (FIGS. 3A-C). In particular, Ki-67 expression was markedly increased by SCGB3A2 treatment in the trachea and lung of Titf1-null mice (FIG. 3C).

Figure 3D:
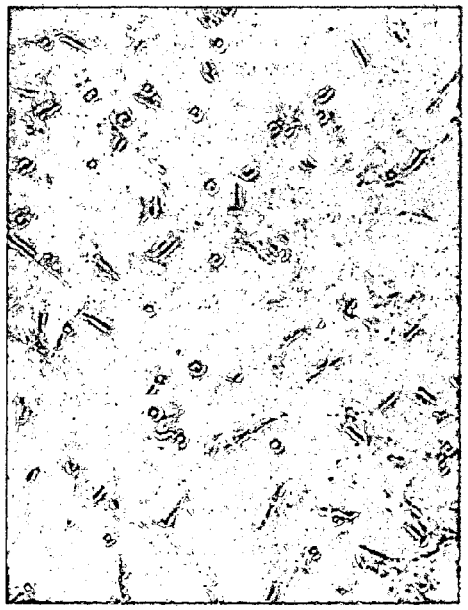
FIG. 3D is a pair of digital images showing primary fetal lung mesenchymal cells that were treated with and without 10 µg/ml SCGB3A2, and were labeled with 10 µM bromodeoxyuridine (BrdU) for 1 hour and subjected to fluorescent activated cell sorting (FACS) analysis. Representative results from three separate experiments for the distribution of BrdU incorporation with and without SCGB3A2 treatment are shown. For each sample, 10,000 cells were analyzed. Values are the mean±SD. Note that upon treatment with SCGB3A2, more cells with incorporated BrdU were found (Gate 5, P<0.05).
Figure 3D:
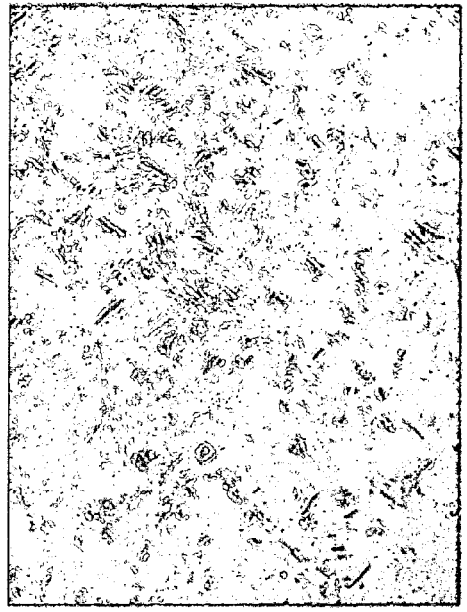
Figure 3D:
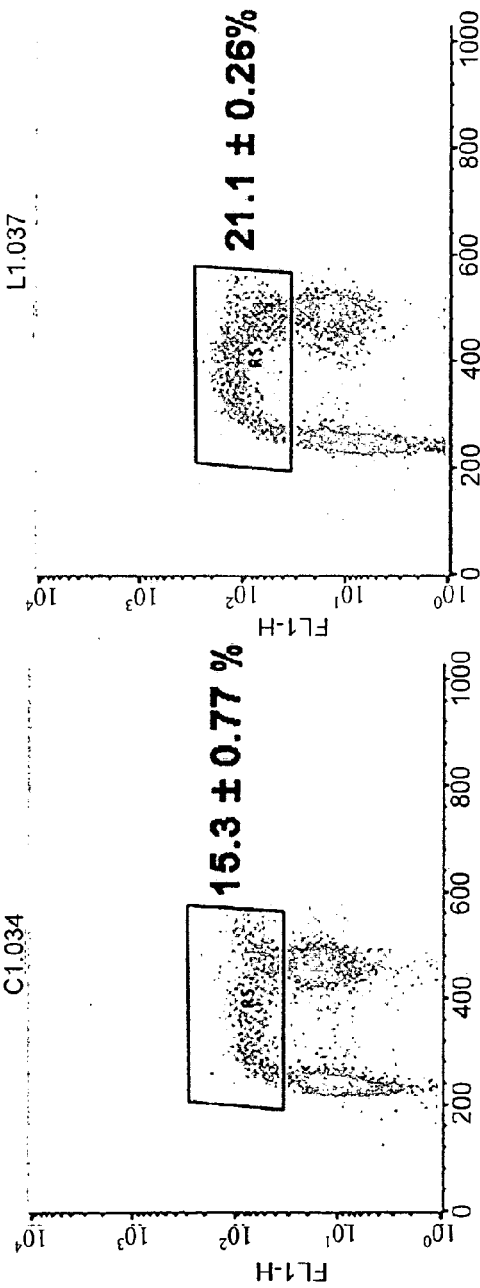

Further, the effect of SCGB3A2 on cell proliferation was accurately determined by BrdU incorporation into primary mesenchymal cells prepared from wild-type mouse fetal lung. A statistically significant increase was obtained, indicating that SCGB3A2 enhanced cell proliferation (FIG. 3D). Cells with sub-G1 content of DNA, consistent with cell death, were not apparent in cells exposed to various concentrations of SCGB3A2 for more than 48 hrs. These results demonstrate that SCGB3A2 enhanced lung mesenchymal cell proliferation.

Figure 3E:
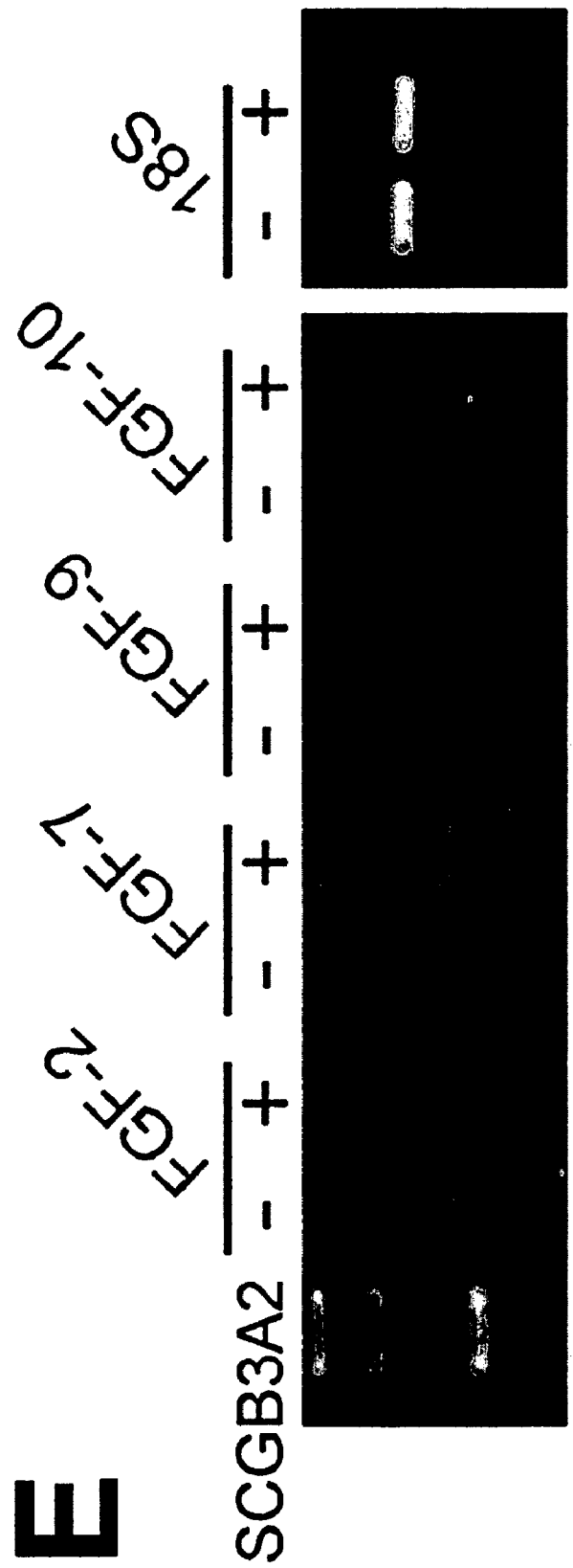
FIG. 3E is a series of digital images showing the RT-PCR analysis of ex vivo cultured Titf1-null lungs for the expression of FGFs with and without SCGB3A2 treatment.

Since SCGB3A2 treatment increased mesenchymal cells in fetal lungs, it was interesting to determine the expression levels of several FGFs, the growth factor mainly expressed in mesenchymes and known to be involved in lung development. Among FGFs analyzed by RT-PCR using RNAs isolated from ex vivo cultured Titf1-null fetal lungs, FGF7 expression was dramatically increased, while FGF2 and FGF9 were minimally increased upon SCGB3A2 treatment (FIG. 3E). Taken together, these results demonstrate that SCGB3A2 induced cell proliferation in Titf1-null trachea and lung.

Example 5

Localization of a SCGB3A2-Specific Receptor in Fetal Lung

This Example demonstrates that the known receptor for SCGB3A2. MARCO, is not responsible for the effects of SCGB3A2 on fetal lungs, and that an independent SCGB3A2-specific receptor likely exists in fetal lungs, especially in mesenchyme.

Figure 4:
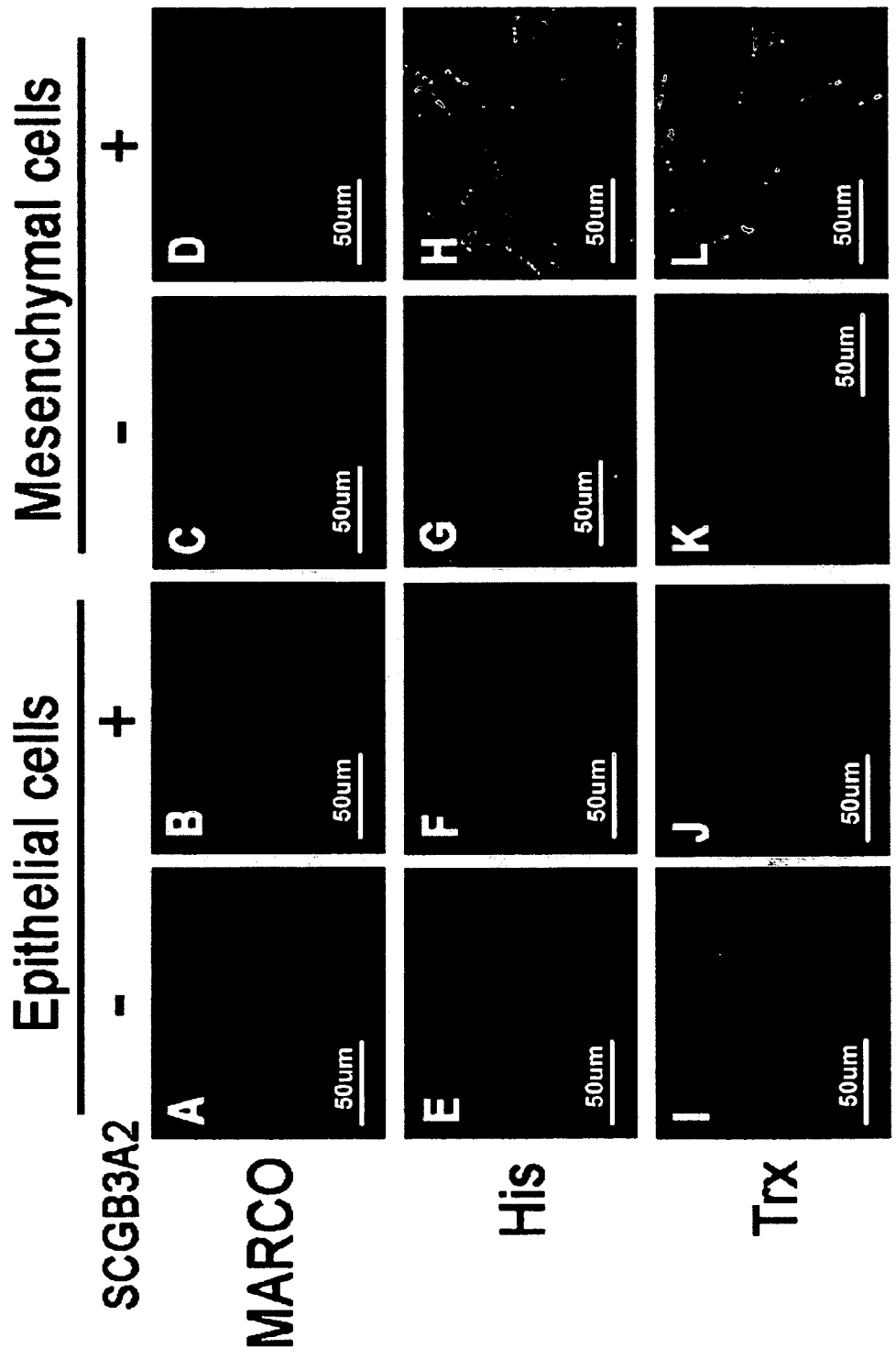
FIG. 4 is a series of digital images showing immunocytochemistry for the possible presence of a SCGB3A2 receptor. Primary fetal lung epithelial and mesenchymal cells were treated with and without 10 μg/ml SCGB3A2 and were subjected to immunocytochemistry for MARCO (FIGS. 4A-D), anti-histidine (His) (FIGS. 4E-H) and anti-thioredoxin (Trx) antibodies (FIGS. 4I-L). Positive signals (green fluorescence) are seen only on the surface of SCGB3A2-treated mesenchymal cells in FIGS. 4H and 4L. Scale bar: 50 μm.

MARCO is the known receptor for SCGB3A2 (Budinger et al., (2006) *Proc. Natl. Acad. Sci. U.S.A.* 103:4604-4609). In order to determine whether a receptor for SCGB3A2 other than MARCO is present in fetal lung, and where it might be localized, wild-type fetal lung primary epithelial and mesenchymal cells were treated with histidine and thioredoxin tag-containing SCGB3A2, and were then subjected to immunocytochemistry using anti-histidine and anti-thioredoxin antibodies (FIG. 4). Immunocytochemistry results revealed that no MARCO immunoreactivity was detected in either epithelial or mesenchymal cells of fetal lung primary culture (FIGS. 4A-D). In contrast, strong signals were detected on the surface of mesenchymal cell membranes, after addition of tagged SCGB3A2, by specific antibodies for histidine and thioredoxin (FIGS. 4H and 4L). Epithelial cells demonstrated no immunoreactivity regardless of SCGB3A2 treatment (FIGS. 4E, 4F, 4I, and 4J). These data indicate that a SCGB3A2-specific receptor, distinct from MARCO, exists in the mesenchymal cells of fetal lung.

Example 6

Identification of a SCGB3A2 Target Gene

This Example illustrates the fact that Rad23b is a downstream target of SCGB3A2 that is involved in SCGB3A2's proliferative effects.

In order to identify genes that are controlled by SCGB3A2 and are responsible for branching, mouse DNA microarray analysis was carried out using Titf1-null lungs with and without SCGB3A2 treatment. Over eighty SCGB3A2-up-regulated genes were selected for further examination for the level and localization of expression by quantitative PCR and in situ hybridization. The focus was on genes localized to the mesenchyme, in which a SCGB3A2-specific receptor is likely to be present.

Expression of one gene, Rad23b, was always up-regulated by SCGB3A2 in all microarray analyses carried out (n=5), and the representative score was 2.4892±0.242048. Rad23b expression was increased 4.73-fold in the ex vivo Titf1-null lungs after SCGB3A2 stimulation as determined by quantitative PCR.

Figure 5:
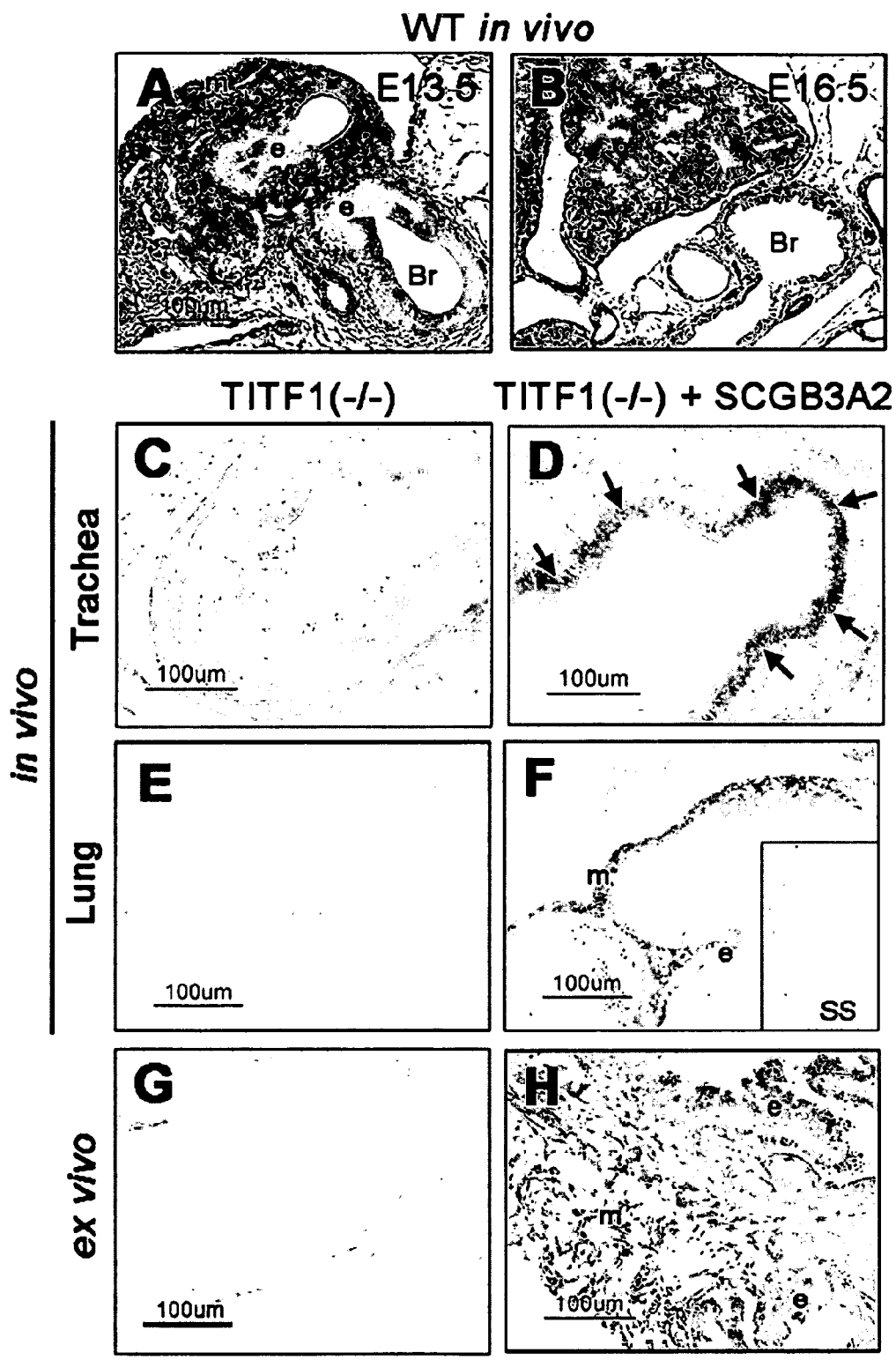
FIG. 5 is a series of digital images showing expression of a candidate SCGB3A2 downstream target gene, Rad23b. Rad23b in situ hybridization was carried out using normal fetal lungs at E13.5 (FIG. 5A) and E16.5 (FIG. 5B), in Titf1-null trachea (FIGS. 5C and 5D) and lung (FIGS. 5E and 5F), and in organ cultured Titf1-null lungs (FIGS. 5G and 5H) with and without SCGB3A2 in the media.

Rad23b is one of the two *Mus musculus* homologs of the *Saccharomyces cerevisiae* DNA repair protein RAD23, and is tightly complexed with xeroderma pigmentosum group C(XPC), serving as a primary DNA damage sensor (Nord et al., 2000 *Ann N Y Acad Sci* 923:154-165). In E13.5 normal fetal lung, in situ hybridization demonstrated that Rad23b mRNA was mainly detected in mesenchymal cells (FIG. 5A). At E16.5, the signal was found both in mesenchymal and bronchial epithelial cells (FIG. 5B). In Titf1-null mouse, the Rad23b expression was weakly detected in the epithelial layer of the trachea (FIG. 5C), but not in the lung (FIG. 5E). SCGB3A2 treatment markedly induced the expression in the basal layer of the trachea (FIG. 5D) and mesenchymal cells of the lung (FIG. 5F). Similarly, no Rad23b mRNA signal was detected in the ex vivo cultured Titf1-null lung (FIG. 5G), which upon stimulation by SCGB3A2 was highly induced in mesenchymal cells and weakly detected in epithelial cells (FIG. 5H). These results indicate that Rad23b likely is a SCGB3A2 downstream target that is responsible for proliferation of Titf1-null lungs.

Example 7

Effect of Decreased Expression of Rad23b on Ex Vivo Lung Development

This Example demonstrates phenotypic effects of knocking down Rad23b expression.

Figure 6:
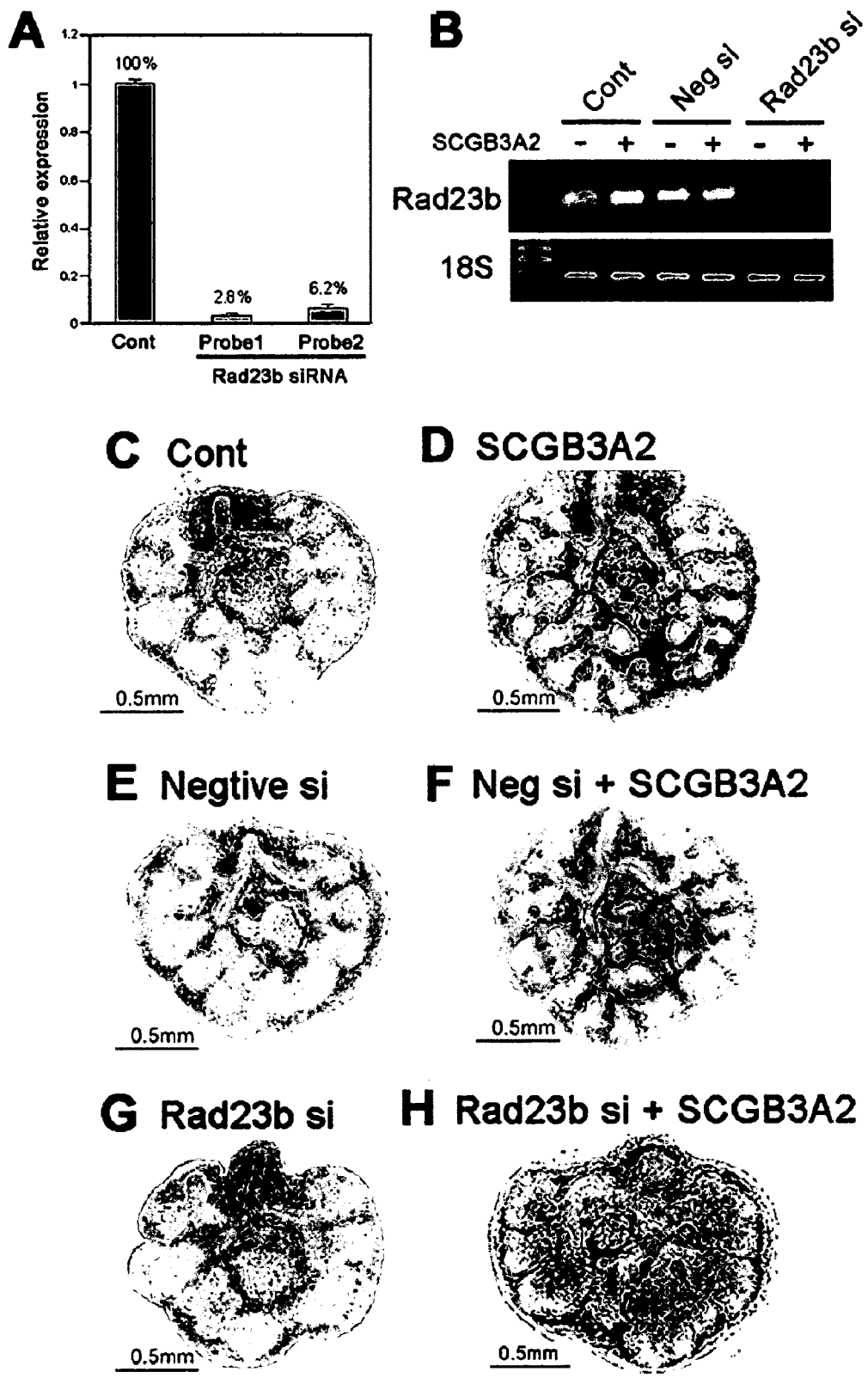
FIG. 6 is a series of graphs and digital images showing the effect of Rad23b siRNA on branching of lung tissue.

In order to confirm that Rad23b is a SCGB3A2 downstream target responsible for lung development, the effect of knocking down Rad23b mRNA using specific siRNA on lung branching morphogenesis was examined in ex vivo lung culture studies. First, Rad23b specific siRNA probes were transfected into primary mesenchymal cells prepared from wild-type fetal lungs. Among four probes examined, two (designated 1 and 2) markedly decreased Rad23b mRNA levels to 2.8% and 6.2%, respectively relative to control non-siRNA transfected cells (FIG. 6A). RT-PCR (reverse transcriptase PCR) analysis demonstrated that Rad23b expression was dramatically suppressed by probe 1, which was slightly recovered by the addition of SCGB3A2 (FIG. 6B).

Negative siRNA did not have any effect on Rad23b expression, and the level was enhanced by treatment with SCGB3A2.

Next, Rad23b siRNA probe1 was used for ex vivo culture studies of fetal lungs (FIGS. 6C-H). Fetal lungs harvested at E11.5 and cultured for two days with negative siRNA (e.g., random sequence siRNA that is not related to Rad23b) presented a similar degree of branching morphogenesis respective to control lungs with and without SCGB3A2 (FIGS. 6E and 6F vs. FIGS. 6C and 6D). In contrast, lungs treated with Rad23b siRNA probe 1 were small and presented delayed branching morphogenesis as compared with lungs of control or treated with negative siRNA (FIG. 6G). Addition of SCGB3A2 to Rad23b siRNA-treated lungs demonstrated small effects, but led to clear advancement of branching as compared with Rad23b siRNA only (FIG. 6H vs FIG. 6G). This small recovery from the Rad23b siRNA-induced delayed branching is in good agreement with the small increase by RT-PCR of Rad23b expression when cells were treated with Rad23b siRNA and SCGB3A2 together. These results demonstrate that SCGB3A2 induced proliferation in fetal lungs, which is mediated through the Rad23b signal.

Example 8

SCGB3A2 Promotes Branching and Proliferation and Functions as a Growth Factor

This Example describes SCGB3A2's growth factor activities and effects on lung development.

As described herein, SCGB3A2 promotes branching and proliferation of fetal lung, mediated through the downstream target Rad23b. This is the first report describing SCGB3A2 as a growth factor in addition to an anti-inflammatory agent, as was demonstrated using a mouse model for allergic airway inflammation (Chiba et al., (2006) *Am. J. Respir. Crit. Care Med* May 1; 173(9):958-64). This growth factor activity of SCGB3A2 seems to be in accordance with the fact that expression of SCGB3A2 is found at E11.5 and greatly increases by E16.5, during the period when lung undergoes dramatic morphological changes.

SCGB3A2 was originally identified as a downstream target for TITF1 in lung using suppressive subtractive hybridization between wild-type and Titf1-null lungs (Niimi et al., (2001) *Mol. Endocrinol.* 15, 2021-2036). SCGB3A2 expression was directly regulated by TITF1 through its binding to specific elements located in the promoter of SCGB3A2 gene (Niimi et al., (2001) *Mol. Endocrinol.* 15, 2021-2036). SCGB3A2 belongs to the secretoglobin (SCG) gene superfamily of small secretory proteins. The prototypical protein of the SCGB gene superfamily, SCGB1A1, was proposed as a novel cytokine (Mukherjee et al., (1999) *Cell Mol Life Sci* 55, 771-87). SCGB1A1 is highly expressed in the airways after E16.5 throughout adulthood (Peri et al., (1995) *J Clin Invest* 96:343-353; Singh & Katyal (2000) *Ann N Y Acad Sci* 923: 43-58) and is known to exhibit an anti-inflammatory function (Ye et al., (2004) *Respiration* 71:505-510; Zhang et al., (1997) *Science* 276:1408-1412). In this context, it is interesting to note that Scgb1a1-knockout mice exhibit no abnormalities in their lungs (Warburton et al., (2000)*Mech Dev* 92:55-81).

Assuming that SCGB3A2 plays a role in lung development, it was interesting to examine whether SCGB3A2 is capable of recovering the development of Titf1-null lungs. As demonstrated herein, the arrest of branching and morphogenesis found in Titf1-null lungs is indeed partly attributed to the deficiency of SCGB3A2. Thus, Titf1-null lung ex vivo cultures exhibited dramatic morphological changes by the addition of SCGB3A2 in the culture medium, presenting pleated and dentate epithelial layers with increased mesenchymes. These morphological changes indicate that SCGB3A2 induced proliferation and invagination, characteristic processes for branching (Minoo et al., (1999) *Dev Biol* 209:60-71; Kaplan (2000) *Mol Genet Metab* 71:321-341).

In in vivo experiments, no invagination was observed, which might be due to low concentrations of SCGB3A2 protein that can reach the lung and/or due to space constraint in the thorax. Nevertheless, the morphological changes observed in SCGB3A2-stimulated Titf1-null lungs somewhat resemble those of tracheal development in *Drosophila* (Minoo et al., (1999) *Dev Biol* 209:60-71; Kaplan (2000) *Mol Genet Metab* 71:321-341) in that the epithelia in Titf1-null trachea and lung were almost barren, and after SCGB3A2 treatment, they became composed of ciliated columnar cells including goblet cells in the entire epithelia. Increased expression of proliferation markers, Ki-67 and phosphorylated histone H3, demonstrated that SCGB3A2 induced proliferation in Titf1-null lung. The effect of SCGB3A2 on cell proliferation was further confirmed in wild-type fetal lung primary mesenchymal cells by BrdU incorporation experiments. In support of this, increased expression of FGFs, particularly FGF7, was found in SCGB3A2-treated ex vivo Titf1-null fetal lungs. This further indicates that epithelial cells proliferate in the presence of SCG3A2 through FGF7 by epithelial-mesenchymal interaction (Wallach-Dayan et al., (2006) *Am J Physiol Lung Cell Mol Physiol* 290:L790-L796; Ng et al., (2002) *Mol Cell Biol* 22:1233-1245).

MARCO (macrophage scavenger receptor with collagenous structure) was reported as a SCGB3A2 receptor in human (Bin et al. (2003) *J. Immunol.* 171, 924-30). MARCO is also known as a receptor for lipopolysaccharide and plays a role in inflammation (Budinger et al., (2006) *Proc. Natl. Acad. Sci. U.S.A.* 103:4604-4609). While the expression of MARCO was found in alveolar macrophages of adult mouse lung by in situ hybridization as expected, the expression was not observed in E13.5 fetal lungs as determined by either in situ hybridization or immunohistochemistry. Further, treatment of wild-type primary fetal lung culture cells with excess SCGB3A2 protein gave positive signals predominantly in the mesenchymal fraction of cells only with anti-histidine and anti-thioredoxin antibodies, but not anti-MARCO antibody, indicating that an unknown SCGB3A2-specific receptor likely exists in fetal lungs, especially in mesenchyme.

DNA microarray analysis was carried out to understand what molecules function through SCGB3A2 signaling in order to promote proliferation and branching in fetal lungs. Among genes up-regulated. Rad23b was selected for further study as a candidate downstream target for SCGB3A2 because Rad23b was mainly expressed in mesenchyme at early embryonic days. Mice lacking the Rad23b gene, its homologue Rad23a, or both genes have been established (Ng et al., (2003) *Genes Dev* 17:1630-1645; Katiyar et al., (2005) *Biochem Biophys Res Commun* 337:1296-1300). Interestingly, Rad23b-null mice exhibit impaired embryonic development (Ng et al., (2003) *Genes Dev* 17:1630-1645). Expression of the human RAD23B gene was found both in cytoplasm and nuclei during G1 phase and mainly in cytoplasm during S phase (Lebeche et al., (1999) *Mech Dev* 86:125-136).

In the present disclosure, Rad23b expression was observed at E13.5 of normal fetal lungs, which increased by E16.5, coinciding with the stage of SCGB3A2 increase. SCGB3A2 also up-regulated Rad23b expression in Titf1-null lung ex vivo and in vivo. Further, Rad23b siRNA delayed branching morphogenesis when examined by ex vivo organ culture studies; this delay was counteracted by the addition of SCGB3A2. This counteraction, however, was not as effective as those of control or negative siRNA in the presence of SCGB3A2. This could be due to a competition between Rad23b siRNA and SCGB3A2 at the concentrations used.

In conclusion, disclosed herein is the discovery that SCGB3A2 is a growth factor, playing a critical role in branching morphogenesis in fetal lungs, whose activity is mediated through the DNA damage sensor gene Rad23b. SCGB3A2 is one of the major genes responsible for the phenotypes observed in the Titf1-null lungs. This growth factor activity of SCGB3A2 indicates that SCGB3A2 can be used to treat many lung diseases such as asthma, chronic obstructive pulmonary disease, cancer, and neonatal respiratory distress.

Example 9

Effect of SCGB3A2 on Bleomycin-Damaged DNA-Materials and Methods

This Example provides specific methods used for carrying out studies using SCGB3A2 to prevent or reverse lung damage caused by anti-cancer agents such as bleomycin.

Animal Studies

For the bleomycin study, 7-8-week-old C57BL/6 female mice or SCGB3A2 transgenic mice that over-express SCGB3A2 in lung, were intratracheally intubated with bleomycin (8 U/kg of body weight; Sigma-Aldrich, St. Louis, Mo.) or PBS as control, or sham intubated at day 0, and euthanized after 3 weeks. Some mice received SCGB3A2 intravenously for a week starting day 1. All animal studies were carried out in accordance with the Using Animals in Intramural Research Guidelines (NIH Animal Research Advisory Committee, NIH, Bethesda, Md.) after approval by the NCI Animal Care and Use Committee.

Cell Culture

Fetal lungs at E16.5 were incubated in DMEM/F12 containing 10% FBS, 1 U/ml Dispase I (Roche Applied Science, Indianapolis, Ind.) and 1,000 U/ml collagenase (Sigma-Aldrich) at 37° C. for 30 minutes with shaking. After incubation, cells were washed three times in DMEM/F12 containing 10% fetal bovine serum (FBS). Cells were then plated onto a 10 cm-plate and incubated for 20 min at 37° C. to separate epithelial cells from mesenchymal cells (Lebeche et al., (1999) *Mech Dev* 86:125-136). While mesenchymal cells attached to the plates, epithelial cells that remain in the media were transferred to a new plate. Embryonic lung primary culture cells were seeded on a 24-well plate at 3×10$^5$ cells/ml for transfection of siRNA or BrdU incorporation. Transfection was carried out using HiPerFect Transfection Reagent (QIAGEN, Valencia, Calif.) according to the manufacturer's protocol.

For TUNEL assay (Promega, San Luis Obispo, Calif. USA) for bleomycin-damaged DNAs, primary fetal lung mesenchymal cells were cultured in LAB-TEK 8-chamber slides (Nalge Nunc International, Rochester, N.Y.) for 44 hours before the addition of bleomycin and harvested 20 hours later. SCGB3A2 was either added together with, or 20 hours earlier than bleomycin addition.

Histological Analysis

Lungs were fixed in 4% paraformaldehyde (PFA) overnight at 4° C. and embedded in paraffin or O.C.T. Compound (SAKURA, Torrance, Calif.). TUNEL assay was performed to detect apoptotic cells in tissue sections using commercially available kit (Promega, Madison, Wis.). Tissue sections were processed according to the manufacturer's instruction, through which a biotinylated nucleotide was incorporated at the 3'-OH end of fragmented DNAs. Biotin incorporation was detected with HRP conjugated streptavidin using DAB as a chromogen.

Example 10

Effect of SCGB3A2 on Bleomycin-Damaged DNA

Bleomycin is well known for causing DNA damage and apoptosis (Povirk (1996) *Mutat Res* 355:71-89; Lee et al., (2005) *Am J Physiol Lung Cell Mol Physiol* 289:L521-528; Wang et al., (2000) *Am. J. Physiol Lung Cell Mol Physiol* 279:L143-151; Budinger et al., (2006) *Proc. Natl. Acad. Sci. U.S.A.* 103:4604-4609; Wallach-Dayan et al., (2006) *Am J Physiol Lung Cell Mol Physiol* 290:L790-L796). Since Rad23b was identified as a component of DNA damage sensor (Sugasawa et al., (1998) *Mol Cell* 2:223-232), and as described herein SCGB3A2 exerts its proliferation activity through Rad23b, it was proposed to determine if SCGB3A2 may affect the extent of bleomycin-induced DNA damage/apoptosis.

Figure 8:
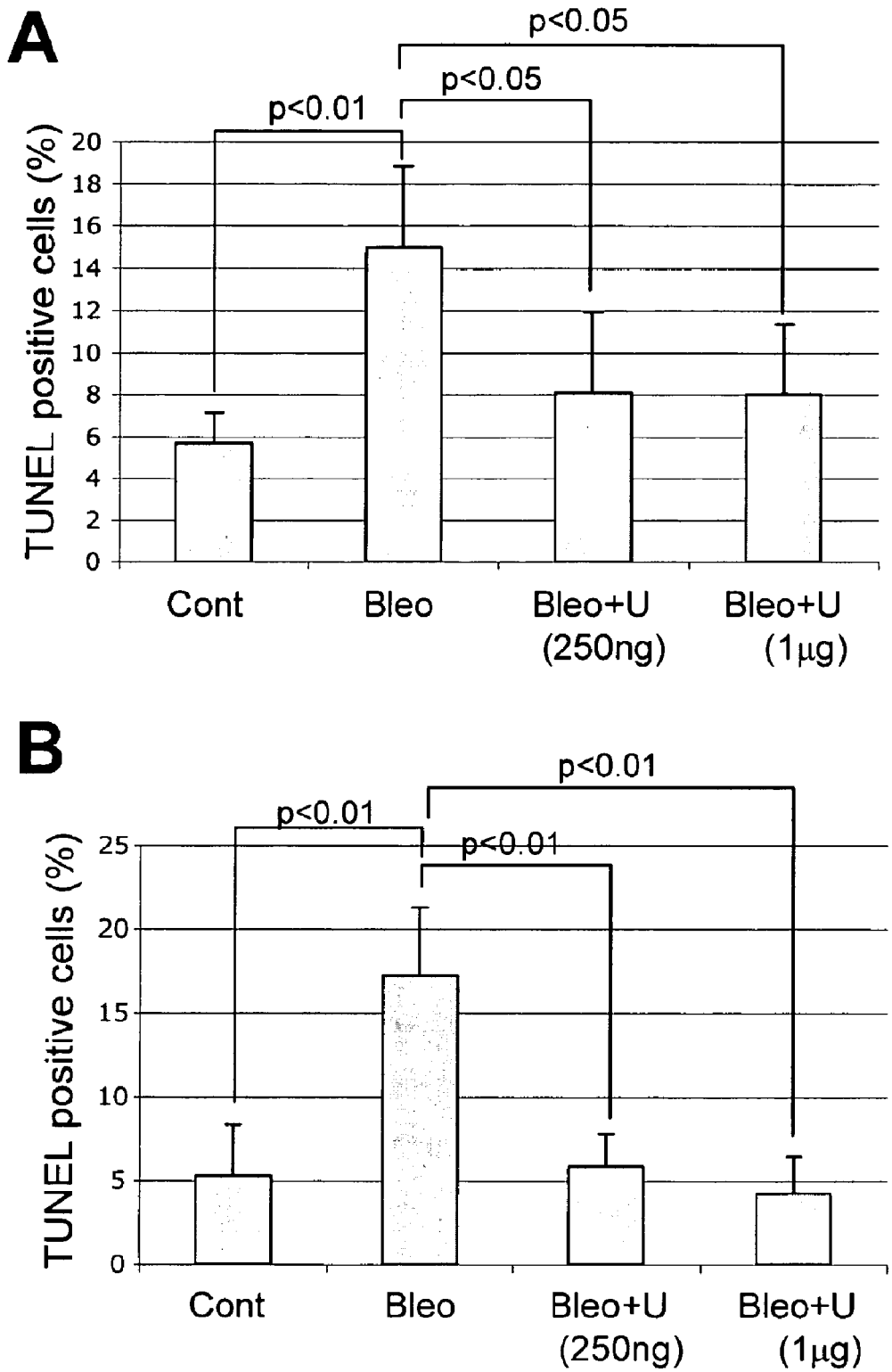
FIG. 8 is a pair of graphs showing terminal deoxynucleotidyl transferase mediated dUTP Nick End Labeling (TUNEL) analysis of bleomycin-treated primary fetal lung mesenchymal cells. SCGB3A2 (250 ng or 1 μg) was added to the culture media together with (FIG. 8A) or 20 hours earlier (FIG. 8B) than bleomycin (25 mU). TUNEL-positive cells are presented as a percentage of total cells.

To this end, fetal lung primary mesenchymal cells were treated with bleomycin with and without SCGB3A2 (FIG. 8) and were subjected to TUNEL assay. When SCGB3A2 was added to the culture media together with bleomycin, the number of TUNEL-positive cells clearly decreased to a level one third above the control level (FIG. 8A), while pre-treating cells with SCGB3A2 before addition of bleomycin completely suppressed bleomycin-induced DNA damage (FIG. 8B). In both cases, 250 ng of HIS-SCGB3A2 was sufficient to repair and/or suppress DNA damage. These results demonstrate that SCGB3A2 functions as (or mediates the function of) a DNA repair anti-apoptotic agent.

Example 11

SCGB3A2 Inhibits or Reduces Bleomycin-Induced Pulmonary Fibrosis

This Example demonstrates that SCGB3A2 can be used to inhibit or reduce lung damage caused by anti-cancer agents such as bleomycin.

Bleomycin, when given to mice by intratracheal intubation, produces interstitial pneumonia and pulmonary fibrosis, which is used as a model for studying human interstitial pneumonia and pulmonary fibrosis (Polosukhin et al., (2005) *Ultrastruct Pathol* 29:53-64; Grande et al., (1998) *Scanning Microscopy* 12:487-494). In order to examine the effect of SCGB3A2 on bleomycin-induced pulmonary fibrosis, wild-type mice as well as SCGB3A2 transgenic mice over-expressing SCGB3A2 in lung under the promoter of human surfactant protein C gene, were subjected to an experimental model mouse for bleomycin-induced pulmonary fibrosis.

Figure 9A:
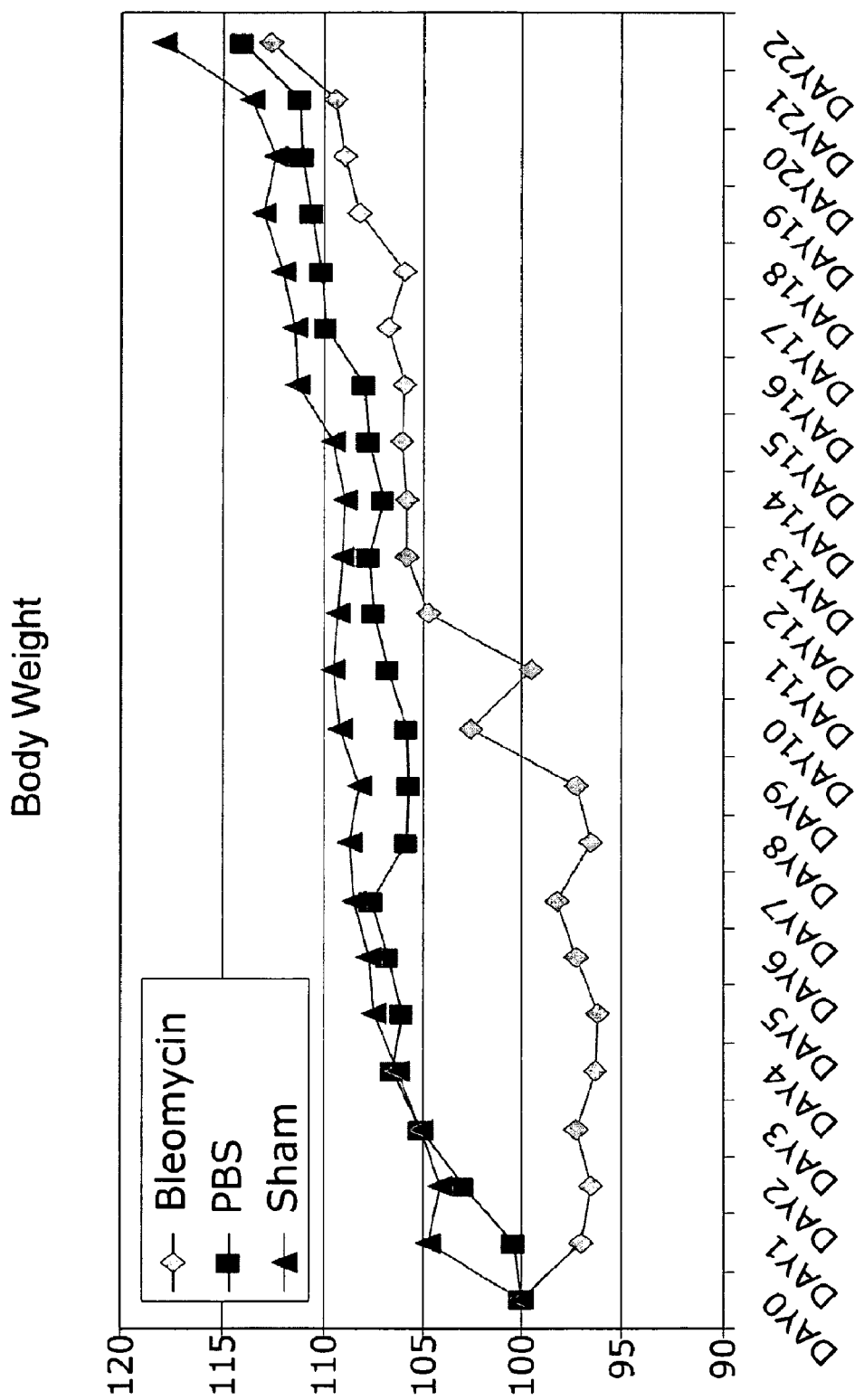
FIG. 9A shows a graph of body weight changes over time. Bleomycin treatment caused a halt of body weight increase as compared with sham or phosphate buffered saline (PBS) treated mice.

After bleomycin intubation, wild-type mice did not gain weight for several days, and although they gradually recovered, never reached the weights of control group of mice (FIG. 9A). After 3 weeks of bleomycin administration, focal interstitial pneumonia with fibrosis and inflammation were observed in lungs of all bleomycin-treated mice (n=6) as determined by H & E staining, and Masson staining which detects collagen fibers (FIGS. 9C, 9D), in contrast to PBS intubated controls (FIG. 9B). When mice were treated with SCGB3A2 for a week starting one day after bleomycin treatment, most of mice presented normal looking lungs with minor lesions of interstitial pneumonia with fibrosis (FIG.

9E) and the presence of large macrophages (FIG. 9F), indicating that the lung had healed from the injury caused by bleomycin.

Figure 10A:
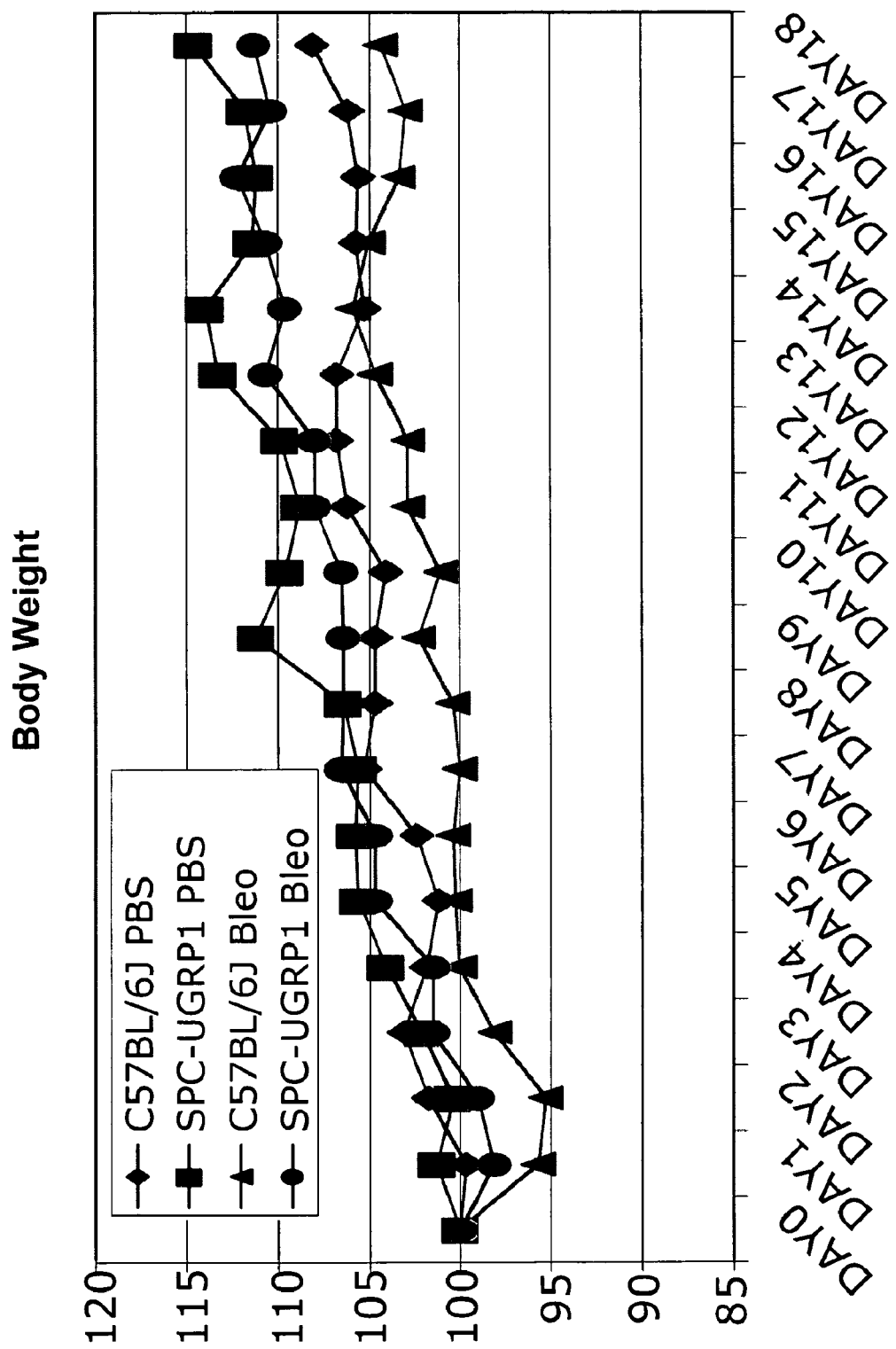
FIG. 10A is a graph of body weight changes over time. SCGB3A2 transgenic mice did not lose weight.

Next, SCGB3A2 transgenic mice were given bleomycin, and the changes in body weight and tissue histology were compared with those of SCGB3A2 transgenic and wild-type mice intubated with PBS, and wild-type mice intubated with bleomycin (FIG. 10). SCGB3A2 transgenic mice expressed much higher levels of SCGB3A2 in many alveolar Type II cells as compared with wild-type mice (FIGS. 10C vs. 10B). SCGB3A2 transgenic mice did not lose any weight after bleomycin intubation, suggestive of no serious damage caused by bleomycin (FIG. 10A). In fact, all lungs of bleomycin-intubated SCGB3A2 transgenic mice presented normal histology (n=5), similar to that seen in wild-type or SCGB3A2 transgenic mice treated with PBS (FIGS. 10G, 10I vs. 10D, 10E). This is in sharp contrast to the lung histology of bleomycin-treated wild-type mice that drastically changed after 3 weeks of treatment as seen in FIG. 9 (FIGS. 10F, 10H vs. 10D). These results clearly demonstrate that SCGB3A2 repairs bleomycin-induced DNA damage. Alternatively, the damage can be completely suppressed by SCGB3A2 if present at high levels prior to bleomycin treatment.

Bleomycin is one of many anti-neoplastic agents that are known to induce DNA damage and apoptosis in lung, resulting in pulmonary fibrosis (Povirk (1996) *Mutat Res* 355:71-89; Lee et al.; (2005) *Am J Physiol Lung Cell Mol Physiol* 289:L521-528; Wang et al., (2000) *Am J Physiol Lung Cell Mol Physiol* 279:L143-151; Budinger et al., (2006) *Proc. Natl. Acad. Sci. U.S.A.* 103:4604-4609; Wallach-Dayan et al., (2006) *Am J Physiol Lung Cell Mol Physiol* 290:L790-L796). Although the involvement of JUNK-dependent mitochondrial death pathway (Povirk (1996) *Mutat Res* 355:71-89), caspase-8 and -9 (Wallach-Dayan et al., (2006) *Am J Physiol Lung Cell Mol Physiol* 290:L790-L796), and Bcl-2 family member Bid (Budinger et al., (2006) *Proc. Natl. Acad. Sci. U.S.A.* 103:4604-4609) has been suggested, the molecular mechanism for bleomycin-induced apoptosis is poorly understood. As disclosed herein, SCGB3A2 functions as an anti bleomycin-induced apoptosis reagent in vitro, and in a mouse model for pulmonary fibrosis it can repair bleomycin-induced interstitial pneumonia and fibrosis. When SCGB3A2 was given prior to bleomycin or by high levels of SCGB3A2 expression such as found in SCGB3A2 transgenic mice, DNA damage by bleomycin did not occur, indicating that the SCGB3A2 signaling pathway may interact with bleomycin-induced apoptosis pathway. Thus, SCGB3A2 can intervene and/or suppress pulmonary interstitial pneumonia and fibrosis.

Example 12

Materials and Methods for Additional Bleomycin Experiments

This Example provides methods that were used to demonstrate that SCGB3A2 inhibits or repairs existing lung damage caused by bleomycin.

Bronchoalveolar Lavage (BAL) Fluid and Cell Count

BAL fluid was obtained after mice were euthanized, by intratracheal instillation of 1 ml PBS in the lung while it was kept located within the thoracic cavity. The lavage was reinfused in the lung two times before final collection. BAL cells were isolated by centrifugation at 3,000 rpm for 10 minutes, and resuspended in 20 µl PBS. Smear preparation of BAL cells were stained with Diff-Quik Stain Set (Dade Behring Inc. Deerfield, Ill.). Cells in 2.25-6.5 $cm^2$ areas of smear preparation (using 3-5 mice) were counted.

Histology

Masson trichrome staining to detect collagen fibers was carried out using Accustain Trichrome Stains (Masson) (Sigma-Aldrich, St. Louis, Mo.) with slight modification.

Example 13

SCGB3A2 Repairs Existing Bleomycin-Induced Lung Fibrosis

Figure 11:
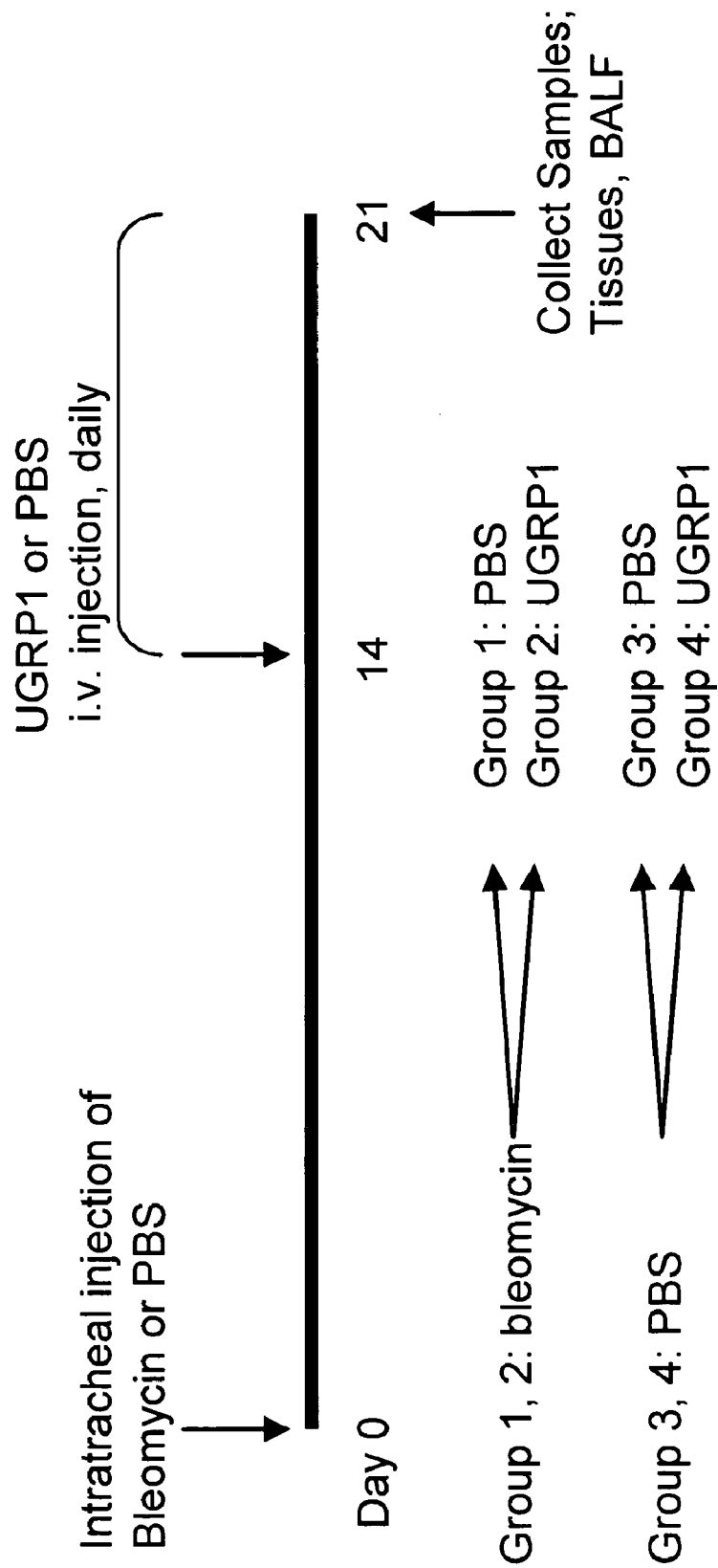
FIG. 11 is a schematic diagram showing the design of the bleomycin experiments described in Examples 11-14. Mice were intratracheally administered bleomycin or PBS at day 0, and SCGB3A2 or PBS was injected intravenously daily for a week starting on day 14. All mice were euthanized on day 21. There are four groups: group 1—bleomycin administration+PBS injection; group 2-bleomycin administration+SCGB3A2 injection; group 3–PBS administration+PBS injection; and group 4—PBS administration+SCGB3A2 injection.

The effect of SCGB3A2 on bleomycin-induced DNA damage was examined using primary fetal lung mesenchymal cells in vitro and a mouse model for bleomycin-induced fibrosis in vivo. In both cases, SCGB3A2 repaired or suppressed bleomycin-induced DNA damage/fibrosis when given together or prior to bleomycin treatment, respectively. Mice were intratracheally administered PBS or bleomycin; each group was further sub-grouped into those that received intravenous injection of PBS or SCGB3A2 daily for a week, starting at the 14th day of the experiment (total of 4 groups) (FIG. 11). All mice were subjected to euthanasia at the 21st day. Bronchoalveolar lavage fluid was collected for inflammatory cell counts and lung tissues were subjected to histological analysis including Masson Trichrome staining that specifically stains for collagen fiber.

Figure 12:
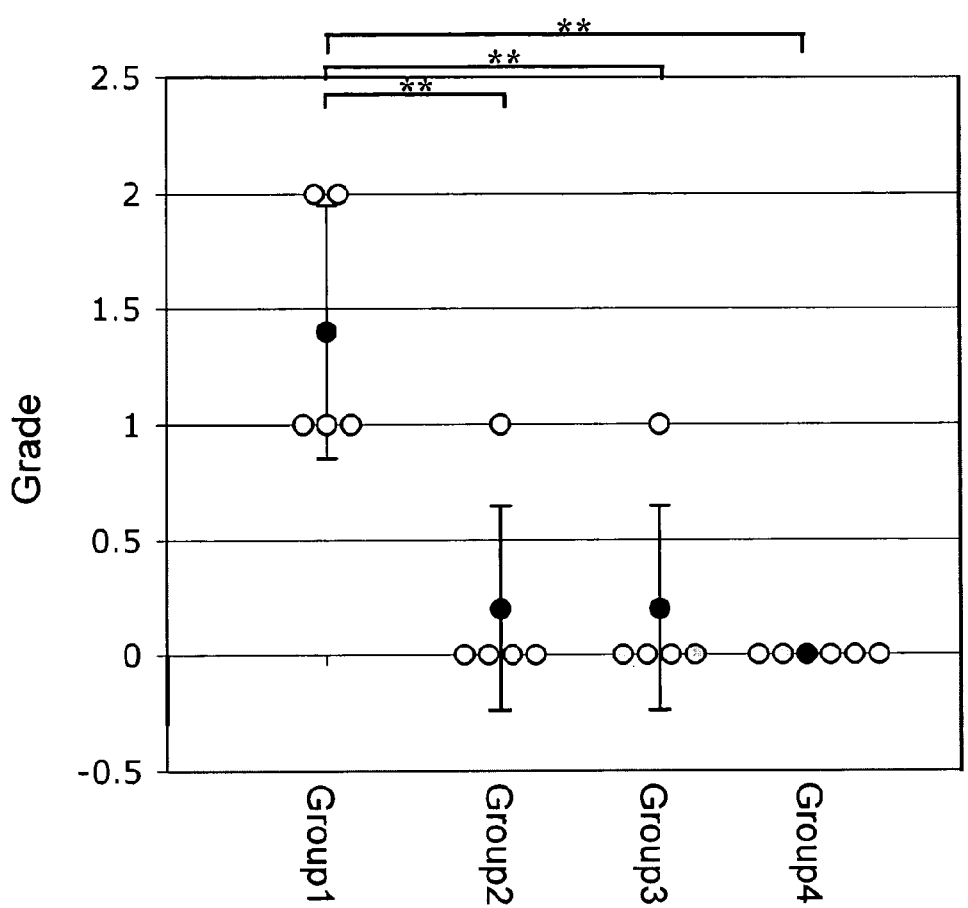
FIG. 12 is a graph showing the grading of bleomycin-induced fibrosis using H&E stained whole lung. Grading was carried out according to the criteria as follows: grade 1—0-25% of fibrous area per whole lung; grade 2—26-50% of fibrous area per whole lung; grade 3—51-75% of fibrous area per whole lung; grade 4; 76-100% of fibrous area per whole lung; and grade±—no fibrosis but a few infiltration foci of lymphocytes or a very small granuloma (shown by gray circle). n=5. Open circle represents each lung. Black circle, average±SD. **P<0.005.
Figure 13:
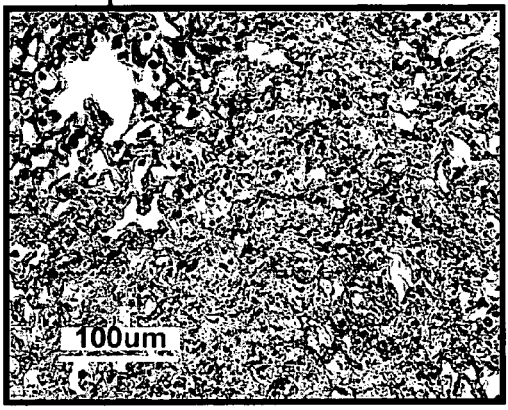
FIG. 13 is a series of digital images showing Masson trichrome staining in whole lung. Representative staining from each group is shown. Collagen fiber was stained with blue color (representative shown by an arrow in groups 2-4). Scale bar: 100 μm.
Figure 13:
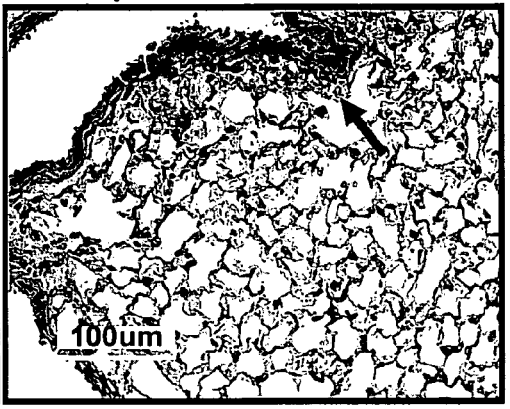
Figure 13:
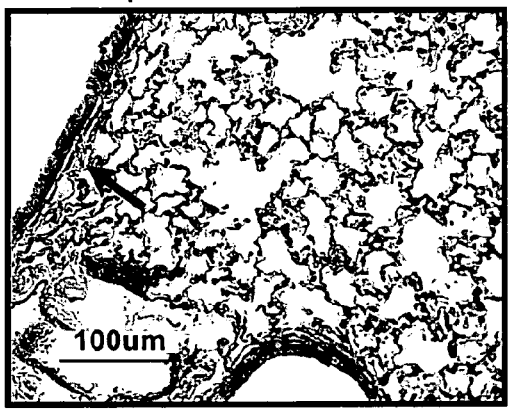
Figure 13:
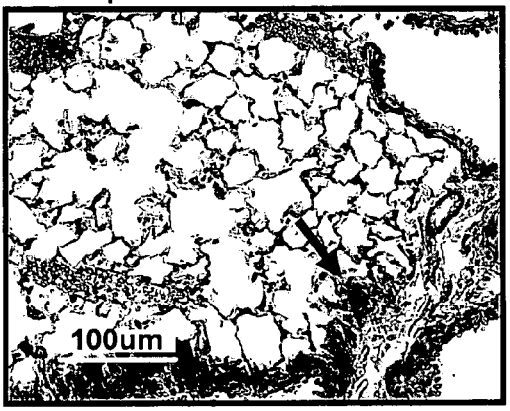

H&E stained whole lung tissues (n=5 in each group) were graded based on the percentage of fibrous area (FIG. 12). Bleomycin-administered and PBS injected group of mice (group 1) demonstrated up to 50% of fibrous areas which drastically diminished with statistical significance to almost none in the bleomycin-administered and SCGB3A2 treated group (group 2), similar to those observed in PBS administered and PBS treated (group 3), and the PBS administered and SCGB3A2-injected group (group 4). Masson Trichrome staining of representative lungs from each group demonstrated highly fibrous areas in group 1 lungs, whereas other groups of lungs (group 2-4) showed clean normal looking histology without traces of fibrosis (FIG. 13). Bleomycin-treated mouse lungs already begin to develop fibrosis after two weeks of treatment, which indicates that SCGB3A2 has repaired fibrosis in group 2 mouse lungs.

Figure 14:
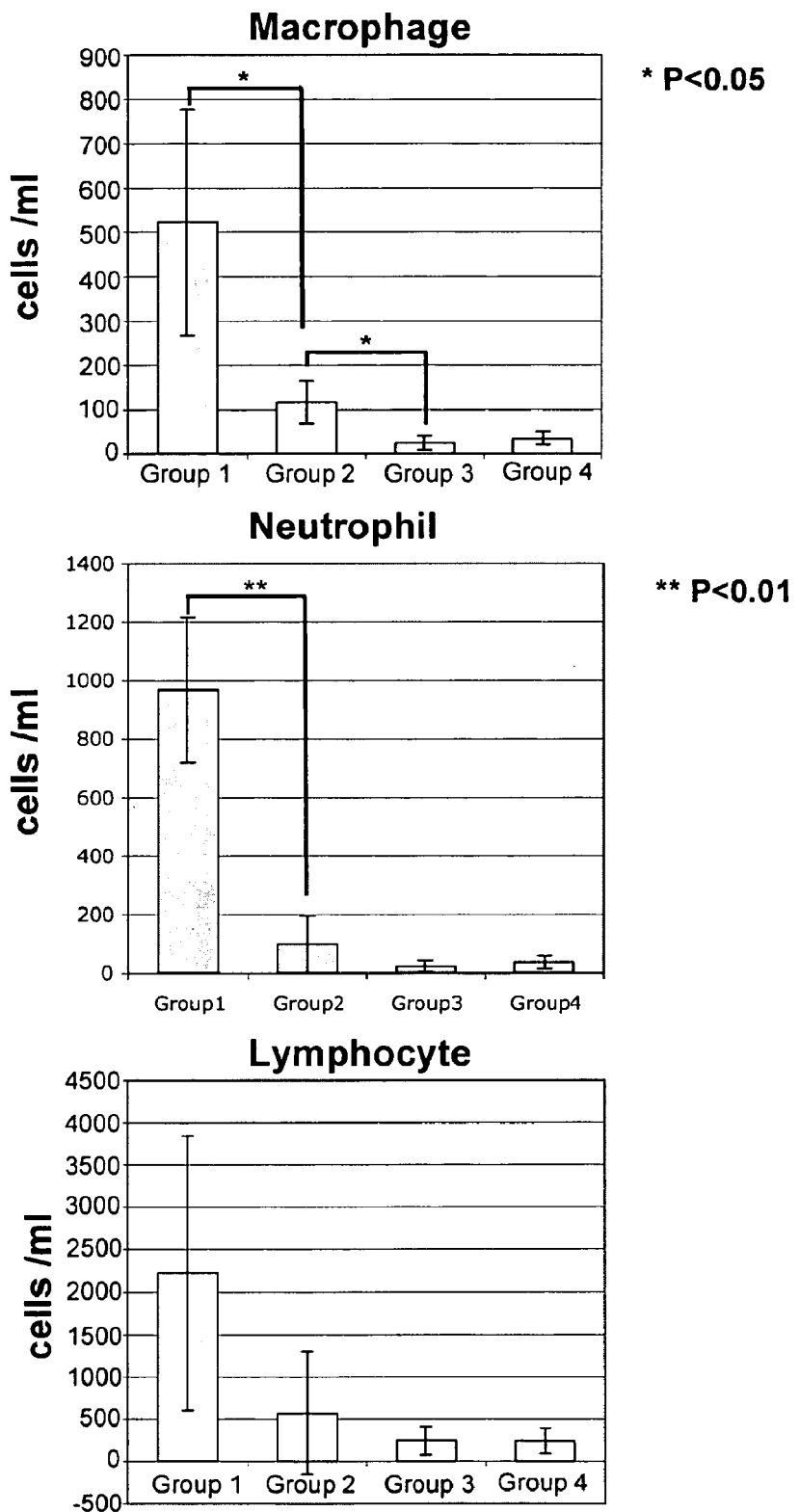
FIG. 14 is a series of graphs showing inflammatory cell counts in bronchoalveolar lavage fluids; groups are as defined in the legend to FIG. 11. Results from 3-5 mice are shown with SD. *P<0.05, **P<0.01.

Next, inflammatory cells in BAL fluid, which were increased as a result of fibrosis and tissue damage, were counted in all groups of mice (FIG. 14). Numbers of macrophages and neutrophils were dramatically decreased in bleomycin-SCGB3A2-treated mice (group 2) as compared with bleomycin-PBS treated mice (group 1). Lymphocyte numbers were also lower in the bleomycin-SCGB3A2-treated group of mice (group 2) as compared with the bleomycin-PBS treated mice (group 1). Group 3 and 4 mice had low levels of inflammatory cells in BAL fluid as expected. The results are in good agreement with the histology of bleomycin-SCGB3A2-treated lungs that presented almost no fibrosis.

The present results demonstrate the striking effect of SCGB3A2 on restoring normal histology of lungs that once had fibrosis. Previously, mice treated with SCGB3A2 daily for a week starting one day after bleomycin administration or SCGB3A2 transgenic mice that over-express SCGB3A2 in their airways, did not develop fibrosis after 3 weeks of bleomycin administration. This is likely due to the fact that SCGB3A2 suppresses apoptosis caused by bleomycin. This early phase effect of SCGB3A2, however, appears to be different from the currently observed effect where SCGB3A2 repaired bleomycin-induced lung fibrosis after it has already begun.

The mechanisms for pulmonary fibrosis are not known. It is currently believed that pulmonary fibrosis cannot be reversed once it has begun. However, as disclosed herein, SCGB3A2 can be used to treat pulmonary fibrosis, particularly at the early stages of the disease. Thus, SCGB3A2 may be given to cancer patients who undergo bleomycin chemotherapy in order to reduce side effects and/or block bleomycin-induced fibrosis.

Example 14

SCGB3A2 Promotes Lung Development In Vivo

This Example demonstrates that SCGB3A2, when administered to the mother, promotes lung development in pre-term mouse pups. The effect of SCGB3A2 was examined on the late gestational stages of fetal lung development in vivo by injecting highly purified tag-free, endotoxin-free SCGB3A2 daily from E13.5 through E16.5 through the tail vein of pregnant female mice, followed by removal of pups from the mother at E17.5. Pups are usually born at E19.0-20.0.

Figure 15A:
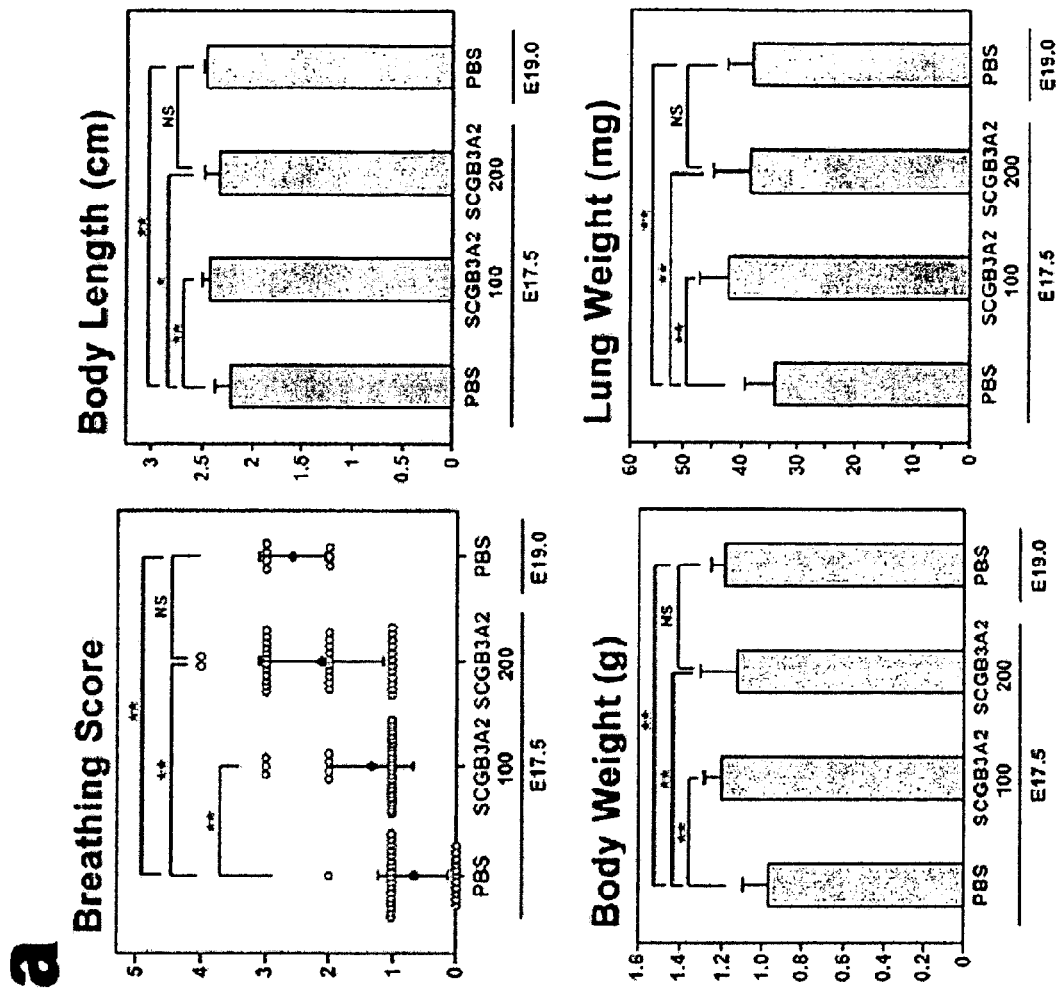
FIG. 15A is a series of graphs showing the lung maturity assessment of treated and untreated mouse pups. E17.5 and 19.5 pups were removed from mothers who had received PBS, 100 μg SCGB3A2, or 200 μg SCGB3A2, and were subjected to breathing score assessment, body length, and body and lung weight measurements. The number of each cohort is as follows: 30 pups from four mothers for PBS-treated E17.5; 32 pups from four mothers for 100 μg SCGB3A2-treated E17.5; 37 pups from five mothers for 200 μg SCGB3A2-treated E17.5; and seven pups from one mother for PBS-treated E19.0. The results are the mean±SD. *$P<0.05$, $P<0.01$, *$P<0.005$ by Student's t-test. NS: not significant.

Pups removed at E17.5 from mothers receiving a total of 100 and 200 µg SCGB3A2 displayed similar body length (to each other), and body and lung weights, which were larger than PBS-treated control pups (FIG. 15A). Breathing scores (Ozdemir et al. (2003) *Pediatr. Res.* 53, 98-103) were also statistically significantly higher among SCGB3A2-treated pups than PBS controls. All lung function parameters obtained from the SCGB3A2-200 treatment group were comparable to those from PBS-treated E19.0 pups. In agreement with breathing scores, SCGB3A2-200-treated E17.5 lungs were well air-inflated and had a similar appearance to that seen with PBS-treated Day 0 lungs, whereas PBS-treated E17.5 lungs did not appear to contain air (FIG. 15B). Further, histological examination revealed that red blood cells were found inside immature alveolar walls of PBS-treated E17.5 lungs, an observation normally obtained with this gestational age of fetal lungs. In contrast, in SCGB3A2-treated lungs, red blood cells were already in contact with airways, indicative of the lung's ability to exchange air (FIG. 15C). In particular, the alveolar walls of SCGB3A2-200-treated lungs were much thinner than PBS-treated lungs, and some of alveolar space was fully extended, a phenotype typically found in E19.0 normal fetal lungs.

Figure 15D:
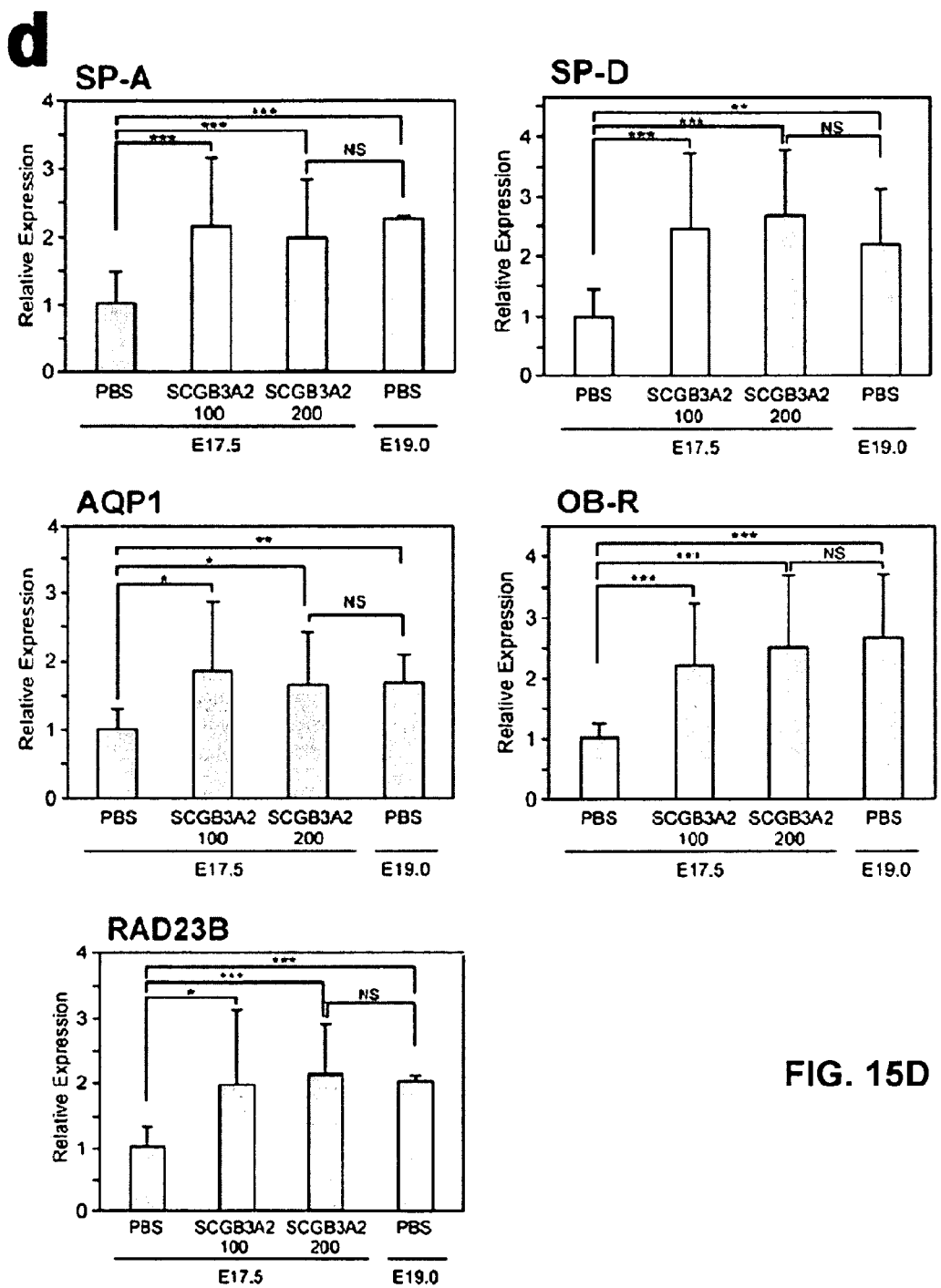
FIG. 15D is a series of five graphs showing quantitative PCR (qPCR) analysis for the expression of surfactant protein (SP)-A, SP-D, aquaporin 1 (AQP1), leptin receptor (OB-R), and Rad23b genes expressed in lungs from PBS (n=9), 100 (n=14) and 200 μg (n=16) SCGB3A2-treated E17.5, and PBS-treated E19.0 (n=4) pups. The results are shown as the means±SD. *$P<0.05$, $P<0.01$, *$P<0.005$ by Student's t-test. NS: not significant.

The expression of several genes known to have markedly increased expression towards the end of gestation was examined by qPCR (FIG. 15D). Expression of surfactant protein (SP)-A and D (Ogasawara et al. (1991) *Biochim. Biophys. Acta* 1083, 252-6), aquaporin 1 (Horster (2000) *Am. J. Physiol. Renal Physiol.* 279, F982-96), and leptin receptor (Henson et al. (2004) *Reproduction* 127, 87-94; Cohen et al. (2005) *J. Biol. Chem.* 280, 10034-9) genes were all significantly enhanced in E17.5 lungs upon SCGB3A2 treatment as compared with PBS, and the levels were similar to E19.0 control pups. Rad23b, which is likely to be a downstream target for SCGB3A2, also exhibited a similar expression pattern.

Figure 15E:
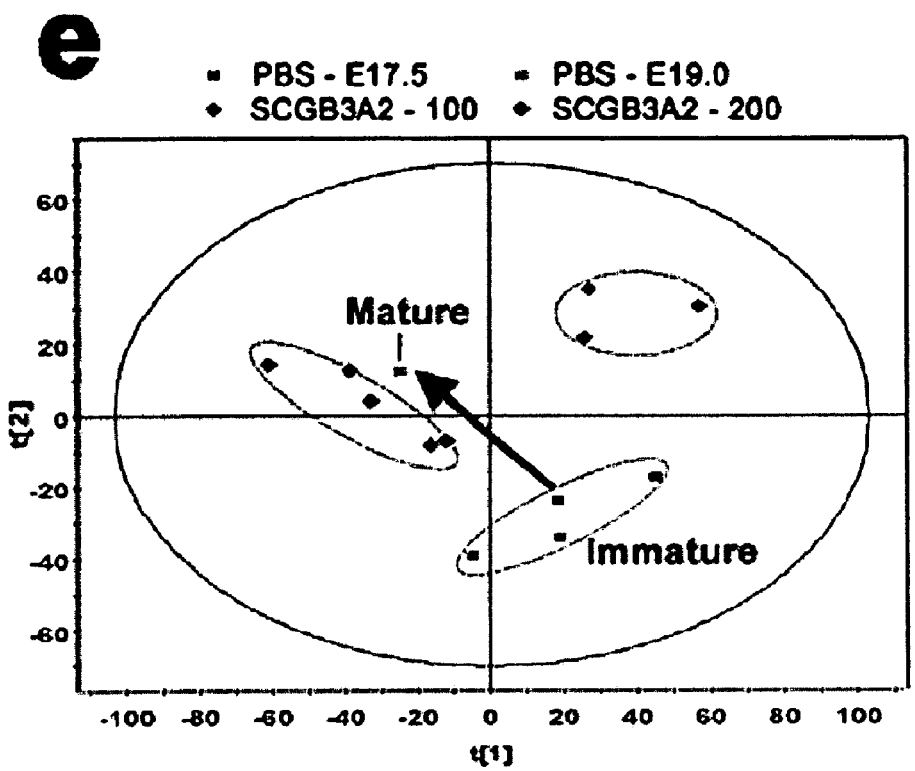
FIG. 15E is a scatter plot of the principal components analysis (PCA) model on the lipidomes of amniotic fluid samples from PBS-treated control (E17.5 and E19.0), and SCGB3A2-treated mice (E17.5 from 100 and 200 μg). Each principal component summarizes an independent latent variable detected by PCA. The t[1] and t[2] values represent the scores of each sample in principal component 1 and 2, respectively. Fitness ($R^2$ value) of the model to the acquired dataset is 0.553, and the prediction power ($Q^2$ value) of the model is 0.242. Each point represents the average of combined amniotic fluids from 7-9 fetuses from a mother, due to volume availability.

Finally, amniotic fluid lipidomes of the SCGB3A2-treated mice were compared with those of immature E17.5 and mature E19.0 controls through a LC-MS-based metabolomic analysis (FIG. 15E). Examining the lipid composition of amniotic lipids has been widely used to predict fetal lung maturity (Brown & Duck-Chong (1982) *Crit. Rev. Clin. Lab. Sci.* 16, 85-159). A two-component model from unsupervised principal component analysis (PCA) showed that SCGB3A2-200 treatment led to the generation of lipid species similar to the mature control, whereas the lipidome after SCGB3A2-100 treatment was different from both immature E17.5 and mature E19.0 controls. Together, these results demonstrate that SCGB3A2 promotes lung development in vivo.

Thus, administration of SCGB3A2 to a pregnant female mouse promoted lung development of preterm pups, which exhibited equivalent lung phenotypes to those of matured term pups. No obvious abnormality was noted with any other organs/tissues of preterm pups, or in mothers treated with SCGB3A2. However, body length and weight were slightly increased in SCGB3A2-treated pups, in accordance with the increase of lung weight. Thus, without intending to be bound by theory, SCGB3A2 may be involved in general pathways of growth promotion. Alternatively, there might be a factor(s) that sets a size of the body in order to accommodate developing lung.

Because the limited volume of mouse amniotic fluid available prevented the use of traditional thin-layer chromatography (Grenache & Gronowski, (2006) *Clin. Biochem.* 39, 1-10), a metabolomic approach that has been adopted in other lipid-related research fields (Griffin & Nicholls (2006) *Pharmacogenomics* 7, 1095-107) was used to examine and compare the lipid profiles of amniotic fluid from control and SCGB3A2-treated samples. Distinctive grouping of immature and mature amniotic fluid samples as well as the samples from SCGB3A2 treatments demonstrated the phenotyping capability of metabolomics on the fetal lung development based on the lipid species in the amniotic fluid. In conclusion, these results demonstrate that SCGB3A2 is a powerful treatment for and preventative of neonatal respiratory distress syndrome.

Example 15

Treatment of Neonatal Respiratory Distress in Humans

This Example provides an exemplary protocol for the treatment of neonatal respiratory distress in humans.

In particular, non-limiting examples, fetal administration is accomplished by transplacental administration, for example by administering the SCGB3A2 to the mother intravenously. Depending on the physical condition of the mother and fetus, and on the length of time available before the anticipated delivery, SCGB3A2 is administered in a dose of from about 0.1 mg/kg to about 100 mg/kg of maternal weight. In one specific, non-limiting example, an effective dose is from about 1 mg/kg to about 20 mg/kg, or in even more particular examples, from about 5 mg/kg to about 10 mg/kg of maternal weight.

The SCGB3A2 can be administered in a single dose, or in multiple doses, for example daily, during a course of treatment. In one embodiment, SCGB3A2 is administered as a single dose of from about 5 mg/kg to about 10 mg/kg of maternal weight. In some instances, this single dose of SCGB3A2 is sufficient to promote lung development such that, following delivery, the infant will have sufficiently mature lungs to breathe independently.

In another embodiment, SCGB3A2 is administered as a series of pulse doses during the course of treatment for as long as delivery can be delayed. For instance, in some embodiments, SCGB3A2 is administered once daily until the time of delivery, or more frequently, for instance twice daily or every 4 or 6 hours, for example.

In some embodiments, SCGB3A2 therapy is combined with glucocorticoid treatment, which also speeds surfactant production. During the course of treatment, lung maturity can continue to be monitored, until such time as the lungs have matured and/or delivery can no longer be delayed. If needed, in some embodiments, the newborn receives ex-utero SCGB3A2 treatment and/or artificial surfactant to further promote lung maturation and function. In many cases, however, in utero treatment with SCB3A2 is sufficient to promote lung maturity, even in very premature births (for instance at 24 weeks or less), such that no further treatment is required.

Example 16

Formulation of SCGB3A2 in a Nanoparticle-Based Delivery System

This Example provides exemplary protocols for producing a nanoparticle-based drug delivery system for direct pulmonary delivery of SCGB3A2. By way of example, the nanoparticles are made from gelatin, or polybutylcyanoacrylate.
Production of Gelatin-Based Nanoparticles Briefly, in one exemplary protocol, 1.25 g of gelatin B is dissolved in 25 ml of distilled water and stirred at 600 rpm under constant heating of 40° C. Twenty-five milliliters of acetone is added to the gelatin solution. The high molecular weight gelatin is then precipitated from the solution. The supernatant containing low molecular size gelatin which is still soluble in the aqueous/organic solvent mixture is then discarded. The high molecular weight gelatin is then redissolved in 25 ml of distilled water and stirred at 600 rpm under constant heating of 40° C.; the pH of the solution is adjusted to 2.5 by adding 1N HCl; 75 ml of acetone is added to the acidic gelatin solution drop-wise, and the nanoparticles are precipitated from the solution.

One hundred and twenty-five microliters of 1 mg/ml of solution of Texas Red in acetonitrile is added and stirred for 1 hour. The particles are stabilized using 400 µl of 25% glutaraldehyde as a cross-linking agent, and the suspension is left stirring for 12 hours without heating. The remaining solvent is evaporated using a Rotavapor (for instance, IKA, Model RV 05, Staufen, Germany). The nanoparticles are purified by centrifugation at 100,000×g (for instance, in a Beckman Model J2-21) for 30 minutes, and are washed three times with distilled water. The resulting particles are re-dispersed in 25 ml of distilled water. The fluorescently-labeled nanoparticles are then stored at 4° C. and protected from light.
Production of Polybutylcyanoacrylate-Based Nanoparticles Briefly, in one exemplary protocol, polybutylcyanoacrylate nanoparticles are prepared by an emulsion polymerization process described by Scherer et al. (1993) *J. Drug Target* 1, 21-27. Fifty milligrams of FITC-Dextran is added to 10 ml of 0.01N HCl. The solution is stirred at 600 rpm; 100 µl of the monomers are slowly added by pipette to the solution. The solution is then stirred for 4 hours and is protected from light; the pH is subsequently adjusted using 1N NaOH to pH 5.0. The particles are then purified from unbound dye and polymerization residuals as described for the gelatin particles, above.

Nanoparticles are then suspended in 25 ml of distilled water after centrifugation, yielding 2 mg/ml of poly-cyanoacrylate nanoparticles.
Spray-Drying To prepare inhalable nanoparticle powders, spray-drying is a commonly practiced method (see, for instance, Bosquillon et al. (2001) *J. Control. Release* 70, 329-339; Mackin et al. (1997) *Pharm. Sci.* 3, 583-586; Vanbever et al. (1999) *Pharm. Res.* 16, 1735-1742). For spray-drying the nanoparticles (gelatin or polybutylcyanoacrylate), a Mini-Spray Dryer produced by Büchi Laboratoriums-Technik (Flawil, Switzerland) or the equivalent is used. The Mini-Spray Dryer operates on the principle of a nozzle spraying in a parallel-flow (the sprayed product and the drying air flow are in the same direction). The adjustable parameters include inlet and outlet temperature, solution pump flow rate, and the aspirator partial vacuum. In one exemplary protocol, the inlet air temperatures range from about 170 to 180° C., the pump flow rate is about 2 ml/minute, the aspirator is set to 40 $m^3$/hour, and the atomizing air flow rate is about 700 l/hour (80 psi). The solution is pumped into the feeding system of the spray-dryer. The resultant powder is then blown through the cyclone separator and collected in a container. Exhaust air is extracted out of the cyclone by a vacuum pump and filtered using a fiber filter.

Five grams of SCGB3A2 are then dissolved in 75 ml of distilled water and heated up to 40° C. to increase the SCGB3A2 solubility. Then, the solution is mixed with 25 ml of either gelatin nanoparticles or polybutylcyanoacrylate nanoparticles. The glass chambers of the spray dryer are shielded from light. The powders are removed from the collector vessel and stored at room temperature under light protection.

Example 17

Growth of Lung Cells on Poly-DL-Lactic Acid Scaffolds

This Example describes an exemplary method of growing lung cells on poly-DL-lactic acid scaffolds in order to engineer lung tissue for transplant (see, for instance, Lin et al. (2006) *J. Biomaterials Applications* 21, 109-118). Poly-DL-lactic acid (PDLLA) is a well-known super-high molecular-weight acid that has good biocompatibility and degrades following in vivo implantation (see, for instance, Lee & Gardella (2002) *Analytical and Bioanalytical Chem.*, 373(7): 526-537). In one exemplary protocol, either dense (non-porous) 2-D films and 3-D foam scaffolds of high porosity are used. Poly-DL-lactic acid films are prepared by dissolving 0.15 g of the polymer homogeneously in 3 mL of dimethyl carbonate (DMC) at 50° C. This polymer-solvent mixture is applied to circular glass coverslips (16 mm in diameter to fit into 24-well cell culture plates) previously cleaned with acetone and alcohol. The coverslips are left at room temperature in a fume hood for 48 hours to remove the solvent and then are immersed in distilled water for 24 hours. The PDLLA films are then peeled intact from the coverslips and stuck to the base of the cell culture wells (24-well plates; for instance, Triple Red, UK) using a small amount of DMC. The PDLLA foams are prepared by thermal induced phase separation (TIPS) processing. Briefly, PDLLA with an inherent viscosity of 1.62 dL/g is used (for instance, Purasorb, Purac Biochem, Goerinchem, The Netherlands). The polymer is dissolved in DMC to give a polymer weight to solvent volume ratio of 5%. The mixture is then stirred overnight to obtain a homogeneous polymer solution. The solution is then transferred to a lypholization flask, immersed in liquid nitrogen, and maintained at −196° C. for 2 hours. The frozen solution is then transferred into an ethylene glycol bath at −10° C. and connected to a vacuum pump ($10^{-2}$ Torr). The solvent is sublimed at −10° C. for 48 hours and then at 0° C. for 48 hours. The foam samples are subsequently completely dried at room temperature in a vacuum oven until reaching a constant weight, for instance, as determined using an electronic balance.

The multiwell plates containing films or foams are sterilized prior to use by exposure to UV light for 1 hour. The discs and foams are preconditioned for 9 days in basal HUES medium (Invitrogen, Paisley, UK), which includes 50% Kaighn's modification of F-12 (F-12K), 50% Dulbecco's modified Eagle's medium (DMEM; LGC, UK) with an added 10% antibiotic/antimycotic (A/A) solution (Invitrogen, UK). The medium is changed each day with a decreasing A/A concentration. Lung epithelium cells, either from primary cultures or cell lines, are seeded at a density of 2000 cells/cm$^2$ (a total of 4000 cells per well) on to the PDLLA films in 24-well plates and grown for 1-8 days or more in the presence of 10 ng-10 mg/ml SCGB3A2, with the medium being changed each day. The PDLLA foams are seeded with lung epithelial cells and cultured for 1-8 days or more in the presence of 10 ng-10 mg/ml SCGB3A2, and the medium is changed each day. After the lung cells have grown to the desired density/maturity, the foams are washed and transplanted into an area of diseased or damaged lung tissue in a subject.

In view of the many possible embodiments to which the principles can be applied, it should be recognized that the illustrated embodiments are only examples and should not be taken as a limitation on the scope of the disclosure. Rather, the scope is in accord with the following claims. We therefore claim all that comes within the scope and spirit of these claims.

We claim:

1. A method of promoting lung development in a fetus, comprising:
administering a therapeutically effective amount of murine or human SCGB3A2 to a pregnant mouse or human subject, wherein administration of the SCGB3A2 to the subject results in administration of the SCGB3A2 to the fetus in the pregnant subject, and wherein the administration of the SCGB3A2 to the fetus increases lung branching morphogenesis in the fetus, thereby promoting lung development in the fetus.

2. The method of claim 1, wherein administration to the fetus in the pregnant subject is transplacental administration or amniotic administration.

3. The method of claim 1, wherein the subject is at risk for premature delivery.

4. The method of claim 1, wherein about 0.1 mg/kg to about 100 mg/kg of SCGB3A2 is administered to the pregnant subject.

5. A method of promoting lung development ex vivo, comprising, culturing a murine or human lung explant with an effective amount of murine or human SCGB3A2, wherein culturing the lung explant increases lung branching morphogenesis in the lung explant, thereby promoting lung development ex vivo.

6. The method of claim 5, further comprising transplanting the lung explant into a murine or human subject after the lung explant is cultured with SCGB3A2.

7. The method of claim 6, wherein the lung explant is cultured in about 10 ng/ml to 10 mg/ml SCGB3A2 prior to transplantation.

* * * * *